United States Patent
Shimamoto et al.

(10) Patent No.: US 6,331,548 B1
(45) Date of Patent: Dec. 18, 2001

(54) 1-CYCLOALKYL-1,8-NAPHTHYRIDIN-4-ONE DERIVATIVE AS TYPE IV PHOSPHODIESTERASE INHIBITOR

(75) Inventors: Tetsuo Shimamoto, Suita; Hidekazu Inoue; Yasuhiro Hayashi, both of Osaka, all of (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/402,142
(22) PCT Filed: Jan. 29, 1999
(86) PCT No.: PCT/JP99/00404
  § 371 Date: Sep. 29, 1999
  § 102(e) Date: Sep. 29, 1999
(87) PCT Pub. No.: WO99/38867
  PCT Pub. Date: Aug. 5, 1999

(30) Foreign Application Priority Data

Jan. 29, 1998 (JP) .................................. 10-017009

(51) Int. Cl.[7] ...................... A61K 31/435; C07D 471/04
(52) U.S. Cl. ............................... 514/300; 546/123
(58) Field of Search ............................ 546/123; 514/300

(56) References Cited

U.S. PATENT DOCUMENTS

| | | | |
|---|---|---|---|
| 4,284,629 | * 8/1981 | Grohe et al. | 544/58.6 |
| 4,840,954 | * 6/1989 | Petersen et al. | 514/254 |
| 5,245,037 | * 9/1993 | Kuramoto et al. | 546/156 |

FOREIGN PATENT DOCUMENTS

| | | |
|---|---|---|
| 61-148179 | * 7/1986 | (JP) . |
| 62-0333176 | * 2/1987 | (JP) . |
| 08151377 | 11/1996 | (JP) . |
| WO/9412499 | 6/1994 | (WO) . |
| WO/9606843 | 3/1996 | (WO) . |
| WO/9704775 | 2/1997 | (WO) . |
| 99/07704 | 2/1999 | (WO) . |

OTHER PUBLICATIONS

A. Matsuura et al., "Substituted 1,8–Naphthyridin–2(1H)–ones as Selective Phosphdiesterase IV Inhibitors", Biol. Pharm. Bull., vol. 17, No. 4, 1994, pp. 498–503.

Tapiero C. et al., "Nucléosides de synthé. VII. Snr l'obtention de ribofuranosides de phénothiazine et de naphtyridine–1,8" J. Heterocycl. Chem. 12(2):439–440 (Apr. 1975).

* cited by examiner

Primary Examiner—Bernard Dentz
(74) Attorney, Agent, or Firm—Burns, Doane, Swecker & Mathis, L.L.P.

(57) ABSTRACT

A 1-cycloalkyl-1,8-naphthylidin-4-one derivative having the formula (I):

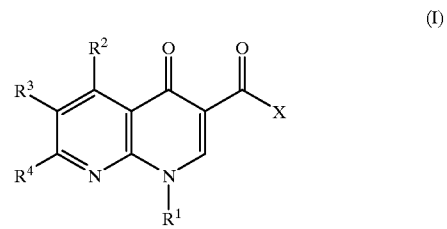

wherein $R^1$ indicates a substituted or unsubstituted cycloalkyl group or a substituted or unsubstituted heterocycloalkyl group, $R^2$, $R^3$, and $R^4$ independently indicate a hydrogen atom, a substituted or unsubstituted lower alkyl group, or a halogen atom, X indicates a group $NR^5R^6$ or a group $OR^7$, wherein $R^5$ and $R^6$ independently indicate a hydrogen atom, a substituted or unsubstituted lower alkyl group, a substituted or unsubstituted cycloalkyl group, a substituted or unsubstituted aryl group, or a substituted or unsubstituted heteroaryl group, and $R^7$ indicates a hydrogen atom, a substituted or unsubstituted lower alkyl group, or a substituted or unsubstituted cycloalkyl group or a pharmaceutically acceptable salt or solvate thereof and a type IV phosphodiesterase inhibitor containing the same as an effective component.

35 Claims, No Drawings

1-CYCLOALKYL-1,8-NAPHTHYRIDIN-4-ONE DERIVATIVE AS TYPE IV PHOSPHODIESTERASE INHIBITOR

This application is a 371 of PCT/JP99/00404, filed Jan. 29, 1999.

TECHNICAL FIELD

The present invention relates to a 1-cycloalkyl-1,8-naphthyridin-4-one derivative having a selective type IV phosphodiesterase inhibiting action and a salt, and solvate thereof as well as a type IV phosphodiesterase inhibitor and a pharmaceutical composition for preventing or treating of cytokine related diseases containing the same as an effective component.

BACKGROUND ART

The intracellular second messenger cAMP or cGMP is broken down and deactivated by phosphodiesterase (PDE), which is classified into at least types I to VII. PDE is widely distributed in the tissue and organs of the body. Among these, type IV phosphodiesterase selectively breaks down cAMP and is found in the central tissue and in the heart, lungs, kidneys, and other organs and in the various hemocyte components etc. Further, it is known to be involved in the derivation of IL-1 and IL-6, TNF-α, and other various cytokines.

Catechol type derivatives such as rolipram, known to be a selective inhibitor of type IV phosphodiesterase, quinazoline type derivatives such as nitraquazone, xanthine type derivatives such as theophylline and denbufylline, etc. are being used or developed as antidepressants, antiasthmatics, antiinflamatorics, etc. No drug has however yet been developed which solves the problems such as the selectivity with other isoenzymes and various side effects. There is no satisfactory medicine which has this enzyme inhibiting action as the main mechanism for achieving the medicinal effect.

On the other hand, as a compound having a naphthyridinone skeleton, for example, as a compound having a carbonyl group at the 2-position in the 1,8-naphthylidine skeleton, there are known those described in JP-A-55-164682, and as a compound having a carbonyl group at the 2-position and a PDE IV inhibiting action, there are known those described in WO-A-94-12499, WO-A-96-06843, etc.

Further, as a compound having a PDE IV inhibiting action and a carbonyl group at the 4-position in a 1,8-naphthyridine skeleton, WO-A-97-04775 describes one where the 1-position substituent group is an ethyl group. Further, as the method of synthesis described in this publication, the method shown in the following formula was used, based on the method of Kaminsky et al. (J. Med. Chem. 1968, 11, 160). However, the 1-position substituent group disclosed in this method is only an alkyl group.

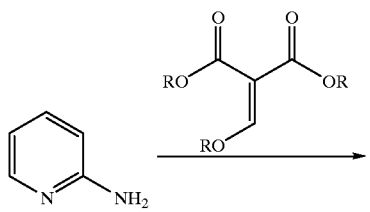

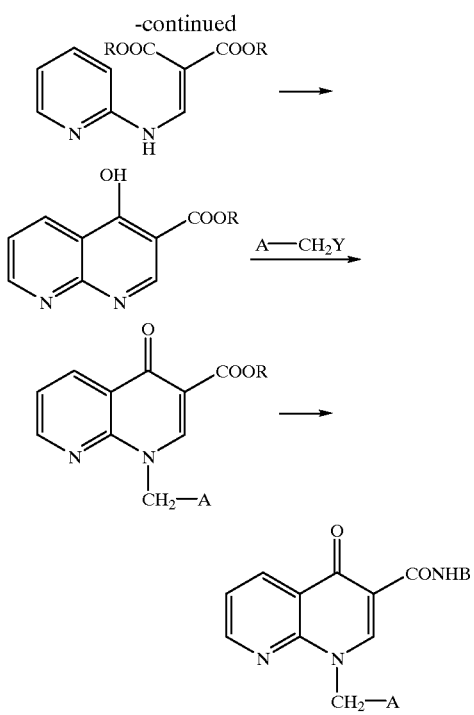

In the above reaction process, it is only possible to use a substitution reaction using a highly reactive alkyl halide (A—CH$_2$—Y), and therefore, the substituent groups which can be introduced to the 1-position are limited.

DISCLOSURE OF INVENTION

The inventors engaged in intensive research to develop a compound having a superior type IV phosphodiesterase inhibiting action and a process for producing the same and, as a result, found that a compound having the formula (I) or (I') with a carbonyl group at the 4-position in the 1,8-naphthyridine skeleton and a cycloalkyl group or a heterocycloalkyl group as the 1-position substituent group has a superior type IV phosphodiesterase inhibiting action, whereby the present invention was completed.

The objects of the present invention are to provide a compound or a salt or solvate thereof, useful as a medicine for the prevention or treatment of bronchial asthma, chronic bronchitis, and other respiratory diseases, diseases relating to abnormality of nervous system such as impaired learning, memory, and recognition relating to Alzheimer's disease, Parkinson's disease, and the like, diseases relating to mental abnormality such as maniac depression and schizophrenia, atopic dermitis, conjunctivitis, acquired immunity disorder syndrome and other inflammatory diseases, osteoarthritis, rheumatoid arthritis, and other general or local joint diseases, rheumatoid arthritis, sepsis, Crohn disease and other diseases which are related to various cytokines such as tumor necrosis factor (TNF-α), and the like by selectively inhibiting the type IV phosphodiesterase and further inhibiting the production of TNF-α.

In accordance with the present invention, there are provided a pharmaceutical composition as well as a type IV phosphodiesterase inhibitor and an agent for prevention or treatment of cytokine related diseases comprising, as an effective component, a 1-cycloalkyl-1,8-naphthylidin-4-one derivative having the formula (I):

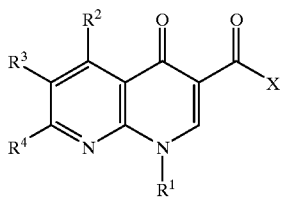

(I)

wherein R¹ indicates a substituted or unsubstituted cycloalkyl group or a substituted or unsubstituted heterocycloalkyl group, R², R³, and R⁴ independently indicate a hydrogen atom, a substituted or unsubstituted lower alkyl group, or a halogen atom, X indicates a group NR⁵R⁶ or a group OR⁷, wherein R⁵ and R⁶ independently indicate a hydrogen atom, a substituted or unsubstituted lower alkyl group, a substituted or unsubstituted cycloalkyl group, a substituted or unsubstituted aryl group, or a substituted or unsubstituted heteroaryl group, and R⁷ indicates a hydrogen atom, a substituted or unsubstituted lower alkyl group, or a substituted or unsubstituted cycloalkyl group or a pharmaceutically acceptable salt or solvate thereof.

In accordance with the present invention, there is also provided a 1-cycloalkyl-1,8-naphthyridin-4-one derivative having the formula (I'):

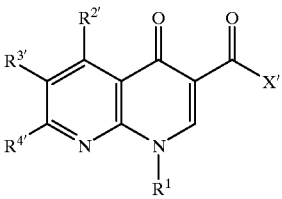

(I')

wherein R¹ indicates a substituted or unsubstituted cycloalkyl group or a substituted or unsubstituted heterocycloalkyl group, R²', R³', and R⁴' independently indicate a hydrogen atom, or a substituted or unsubstituted lower alkyl group, X' indicates a group NR⁵R⁶, wherein R⁵ and R⁶ independently indicate a hydrogen atom, a substituted or unsubstituted lower alkyl group, a substituted or unsubstituted cycloalkyl group, a substituted or unsubstituted aryl group, or a substituted or unsubstituted heteroaryl group or a salt or solvate thereof, which is useful as a type IV phosphodiesterase inhibitor.

BEST MODE FOR CARRYING OUT THE INVENTION

The preferable examples of the cycloalkyl group of the substituted or unsubstituted cycloalkyl group indicated by R¹ in the formulae (I) and (I') according to the present invention are a cycloalkyl group having 3 to 8 carbon atoms such as a cyclopropyl group, a cyclobutyl group, a cyclopentyl group, a cyclohexyl group, a cycloheptyl group, etc. More preferable examples are a cyclopropyl group, a cyclopentyl group, a cyclohexyl group. The cycloalkyl group may be substituted with one or more substituents. The Examples of such substituents are a $C_1$–$C_6$ linear, branched or cyclic lower alkyl group such as a methyl group, an ethyl group, an n-propyl group, an isopropyl group, an isobutyl group, a t-butyl group, a cyclohexyl group, etc.; an aralkyl group such as a benzyl group, a phenethyl group, etc.; an aryl group such as a phenyl group, a methoxyphenyl group, a pyridyl group, etc.; a heterocyclic group such as a morpholinyl group, a piperazinyl group, etc.; a halogen atom such as fluorine, chlorine, bromine, iodine, etc.; an oxygen atom; a sulfur atom; a hydroxyl group; a $C_1$–$C_6$ linear or branched lower alkoxy group such as a methoxy group, an ethoxy group, an n-propoxy group, an isobutyloxy group, a t-butyloxy group, etc.; a cyano group; a nitro group; an amino group; a $C_1$–$C_6$ linear or branched lower alkylamino group such as a methylamino group, an ethylamino group, an n-propylamino group, an isopropylamino group, an isobutylamino group, a t-butylamino group; an acylamide group such as a formamide group, an acetamide group, a benzamide group, etc.; an acylthioamide group such as a formthioamide group, an acetothioamide group, a benzthioamide group, etc.; a lower alkoxycarbonyl amino group such as a methoxycarbonyl amino group, a t-butoxycarbonyl amino group, etc.; an aralkyloxycarbonyl amino group such as benzyloxycarbonyl amino group, a phenetyloxycarbonyl amino group, etc.; a lower alkylaminocarbonyl amino group such as a methylaminocarbonyl amino group, a dimethylaminocarbonyl amino group, etc.; a lower alkylaminothiocarbonyl amino group such as a thiocarbamoyl amino group, a methylaminothiocarbonyl amino group, a dimethylaminothiocarbonyl amino group, etc.; an arylaminocarbonyl amino group such as a phenylaminocarbonyl amino group, a pyridylaminocarbonyl amino group, etc.; an arylaminothiocarbonyl amino group such as a phenylaminothiocarbonyl amino group, a pyridylaminothiocarbonyl amino group, etc.; an aralkylaminocarbonyl amino group such as a benzylaminocarbonyl amino group, a phenetylaminocarbonyl amino group, etc.; an aralkylaminothiocarbonyl amino group such as a benzylaminothiocarbonyl amino group, a phenetylaminothiocarbonyl amino group, etc., a $C_1$–$C_6$ acyl group such as a formyl group, an acetyl group, a propionyl group, an isobutyryl group, a pivaloyl group, a benzoyl group, etc.; an acyloxy group such as a formyloxy group, an acetoxy group, a propionyloxy group, a pivaloyloxy group, a benzoyloxy group, etc.; a carboxyl group; a $C_1$–$C_6$ linear or branched lower alkoxycarbonyl group such as a methoxycarbonyl group, an ethoxycarbonyl group, an n-propoxycarbonyl group, an isobutyloxycarbonyl group, a t-butyloxycarbonyl group, etc.; an aralkyloxycarbonyl group such as a benzyloxy carbonyl group, a phenetyloxycarbonyl group, etc.; a carbamoyl group; a lower alkylaminocarbonyl group such as a methylaminocarbonyl group, a dimethylaminocarbonyl group, etc.; a thiocarbamoyl group; a lower alkylaminothiocarbonyl group such as a methylaminothiocarbonyl group, a dimethylaminothiocarbonyl group, etc.; an arylaminocarbonyl group such as a phenylaminocarbonyl group, a pyridylaminocarbonyl group, etc.; an arylaminothiocarbonyl group such as a phenylaminothiocarbonyl group, a pyridylaminothiocarbonyl group, etc.; an aralkylaminocarbonyl group such as a benzylaminocarbonyl group, a phenetylaminocarbonyl group, etc.; an aralkylaminothiocarbonyl group such as a benzylaminothiocarbonyl group, a phenetylaminothiocarbonyl group; etc.; a thiol group; a $C_1$–$C_6$ linear or branched lower alkylthio group such as a methylthio group, an ethylthio group, an n-propylthio group, an isopropylthio group, an isobutylthio group, a t-butylthio group, etc.; a lower alkylsulfonyl group such as a methanesulfonyl group, an ethanesulfonyl group, etc.; a sulfonylamide group such as a methanesulfonyl amide group, a benzenesulfonylamide group, etc.; a trialkylsilyloxy group such as a trimethylsilyloxy group, a t-butyldimethylsilyloxy group, a t-butyldiphenylsilyloxy group, etc.; and so on.

In the specification, "lower", unless otherwise alluded to, means 1 to 8 carbon atoms, preferably 1 to 6 carbon atoms.

Preferable examples of the cycloheteroalkyl group of the substituted or unsubstituted cycloheteroalkyl group indicated by $R^1$ in the formula (I) or (I') of the present invention are a cycloheteroalkyl group containing 2 to 8 carbon atoms and one or more hetero atoms comprising an oxygen atom, a nitrogen atom or a sulfur atom, such as an aziridinyl group, an azetidinyl group, a pyrrolidinyl group, a piperidyl group, a piperazinyl group, a tetrahydrofuryl group, a tetrahydropyranyl group, a morpholyl group, a thiomorpholyl group. More preferable examples are an azetidinyl group, a pyrrolidinyl group, a piperidinyl group, a tetrahydrofuryl group. The cycloheteroalkyl groups may be substituted with one or more groups. The Examples of such substituents are a $C_1$–$C_6$ linear, branched or cyclic lower alkyl group such as a methyl group, an ethyl group, an n-propyl group, an isopropyl group, an isobutyl group, a t-butyl group, a cyclohexyl group, etc.; an aralkyl group such as a benzyl group, a phenethyl group, etc.; an aryl group such as a phenyl group, a methoxyphenyl group, a pyridyl group, etc.; a heterocyclic group such as a morpholinyl group, a piperazinyl group, etc.; a halogen atom such as fluorine, chlorine, bromine, iodine, etc.; an oxygen atom; a sulfur atom; a hydroxyl group; a $C_1$–$C_6$ linear or branched lower alkoxy group such as a methoxy group, an ethoxy group, an n-propoxy group, an isobutyloxy group, a t-butyloxy group, etc.; a cyano group; a nitro group; an amino group; a $C_1$–$C_6$ linear or branched lower alkylamino group such as a methylamino group, an ethylamino group, an n-propylamino group, an isopropylamino group, an isobutylamino group, a t-butylamino group; an acylamide group such as a formamide group, an acetamide group, a benzamide group, etc.; an acylthioamide group such as a formthioamide group, an acetothioamide group, a benzthioamide group, etc.; a lower alkoxycarbonyl amino group such as a methoxycarbonyl amino group, t-butoxycarbonyl amino group, etc.; an aralkyloxycarbonyl amino group such as benzyloxycarbonyl amino group, a phenetyloxycarbonyl amino group, etc.; a lower alkylaminocarbonyl amino group such as a methylaminocarbonyl amino group, a dimethylaminocarbonyl amino group, etc,; a lower alkylaminothiocarbonyl amino group such as a thiocarbamoyl amino group, a methylaminothiocarbonyl amino group, a dimethylaminothiocarbonyl amino group, etc.; an arylaminocarbonyl amino group such as a phenylaminocarbonyl amino group, a pyridylaminocarbonyl amino group, etc.; an arylaminothiocarbonyl amino group such as a phenylaminothiocarbonyl amino group, a pyridylaminothiocarbonyl amino group, etc.; an aralkylaminocarbonyl amino group such as benzylaminocarbonyl amino group, phenetylaminocarbonyl amino group, etc.; an aralkylaminothiocarbonyl amino group such as benzylaminothiocarbonyl amino group, phenetylaminothiocarbonyl amino group, etc., a $C_1$–$C_6$ acyl group such as a formyl group, an acetyl group, a propionyl group, an isobutyryl group, a pivaloyl group, a benzoyl group, etc.; an acyloxy group such as a formyloxy group, an acetoxy group, a propionyloxy group, a pivaloyloxy group, a benzoyloxy group, etc.; a carboxyl group; a $C_1$–$C_6$ linear or branched lower alkoxycarbonyl group such as a methoxycarbonyl group, an ethoxycarbonyl group, an n-propoxycarbonyl group, an isobutyloxycarbonyl group, a t-butyloxycarbonyl group, etc.; an aralkyloxycarbonyl group such as a benzyloxy carbonyl group, a phenetyloxycarbonyl group, etc.; a carbamoyl group; a lower alkylaminocarbonyl group such as a methylaminocarbonyl group, a dimethylaminocarbonyl group, etc.; a thiocarbamoyl group; a lower alkylaminothiocarbonyl group such as a methylaminothiocarbonyl group, a dimethylaminothiocarbonyl group, etc.; an arylaminocarbonyl group such as a phenylaminocarbonyl group, a pyridylaminocarbonyl group, etc.; an arylaminothiocarbonyl group such as a phenylaminothiocarbonyl group, a pyridylaminothiocarbonyl group, etc.; an aralkylaminocarbonyl group such as a benzylaminocarbonyl group, a phenetylaminocarbonyl group, etc.; an aralkylaminothiocarbonyl group such as a benzylaminothiocarbonyl group, a phenetylaminothiocarbonyl group; etc.; a thiol group; a $C_1$–$C_6$ linear or branched lower alkylthio group such as a methylthio group, an ethylthio group, an n-propylthio group, an isopropylthio group, an isobutylthio group, a t-butylthio group, etc.; a lower alkylsulfonyl group such as a methanesulfonyl group, an ethanesulfonyl group, etc.; a sulfonylamide group such as a methanesulfonyl amide group, a benzenesulfonylamide group, etc.; a trialkylsilyloxy group such as a trimethylsilyloxy group, a t-butyldimethylsilyloxy group, a t-butyldiphenylsilyloxy group, etc.; and so on.

Further, the substituents of the cycloalkyl group represented by $R^1$ and the heterocycloalkyl group represented by $R^1$ may further be substituted with the above-mentioned substituents. For example, as the further substituent of the above-mentioned substituted lower alkyl groups (i.e., lower alkylamino group, lower alkylthio group, etc.), a heterocyclic group, a halogen atom, an oxygen atom, a sulfur atom, a hydroxyl group, an alkoxy group, an alkylthio group, an amido group, a carboxyl group, an acyloxy group, a sulfonylamide group, etc. may be mentioned. As the further substituent of the above-mentioned substituted acyl group, substituted aryl group, substituted aralkyl group (i.e., the acyloxy group, the arylaminocarbonyl group, aralkyloxycarbonyl group, etc.), a lower alkyl group; a substituted lower alkyl group such as a morpholinomethyl group, a piperazinomethyl group, etc; a heterocyclic group, a halogen atom, an oxygen atom, a sulfur atom, a hydroxyl group, an alkoxy group, an alkylthio group, an amide group, a carboxyl group, an acyloxy group, a sulfonylamide group, etc. may be mentioned.

The preferable examples of the lower alkyl group indicated by $R^2$, $R^3$, or $R^4$ and $R^{2'}$, $R^{3'}$ or $R^{4'}$ in the formulae (I) and (I') are $C_1$–$C_6$ linear or branched alkyl group such as a methyl group, an ethyl group, an n-propyl group, an isopropyl group, an isobutyl group, a t-butyl group, etc. The preferable examples of the halogen atom indicated by $R^2$, $R^3$, or $R^4$, in the formula (I), are fluorine, chlorine, bromine and iodine. The preferable examples of a combination of $R^2$, $R^3$, and $R^4$, or a combination of $R^{2'}$, $R^{3'}$ and $R^{4'}$, are all hydrogen atoms.

The preferable examples of the lower alkyl group of the substituted or unsubstituted lower alkyl group indicated by $R^5$ or $R^6$ in formula (I) or (I') are a $C_1$ to $C_6$ linear or branched alkyl group such as a methyl group, an ethyl group, an n-propyl group, an isopropyl group, an isobutyl group, a t-butyl group, etc. The preferable examples of the substituent group of the lower alkyl group are preferably a $C_6$ to $C_{14}$ aryl group such as a phenyl group, etc., a lower alkenyl group such as a vinyl group, etc., a $C_3$ to $C_6$ cycloalkyl group such as a cyclopropyl group, a cyclobutyl group, a cyclopentyl group and a cyclohexyl group; a halogen atom such as fluorine, chlorine, bromine and iodine; a hydroxyl group; a $C_1$–$C_6$ linear or branched lower alkoxy group such as a methoxy group, an ethoxy group, an n-propoxy group, an isobutyloxy group, a t-butyloxy group, etc.; a cyano group, a nitro group, an amino group, a $C_1$–$C_6$ linear or branched lower alkylamino group such as a methylamino group, an ethylamino group, an n-propylamino group, an isopropylamino group, an isobutylamino group, a t-butylamino group, an acylamide group such as a formamide group, an acetamide group, a benzamide group, etc.; a $C_1$–$C_6$ acyl group such as a formyl group, an acetyl group, a propionyl group, an isobutyryl group, a t-butyryl group, a benzoyl group, etc.; an acyloxy group such as a formyloxy group, an acetoxy group, a benzoyloxy group, etc.; a carboxyl group; a $C_1$–$C_6$ linear or branched lower alkoxycarbonyl group such as a methoxycarbonyl group, an ethoxycarbonyl group, an n-propoxycarbonyl group, an isobutyloxycarbonyl group, a t-butyloxycarbonyl group, etc.; an aralkyloxycarbonyl group such as a benzyloxycarbonyl group, a phenetyloxycarbonyl group, etc.; a carbamoyl group, a thiol group, a $C_1$–$C_6$ linear or branched lower alkylthio group such as a methylthio group, an ethylthio group, an n-propylthio group, an isopropylthio group, an isobutylthio group, t-butylthio group, etc.; a sulfonyl group; etc.

The preferable examples of the cycloalkyl group of the substituted or unsubstituted cycloalkyl group indicated by $R^5$ or $R^6$ in formulae (I) and (I') are a $C_3$–$C_6$ cycloalkyl group such as a cyclopropyl group, a cyclobutyl group, a cyclopentyl group, a cyclohexyl group, etc. The preferable examples of the substituent group for the cycloalkyl group are a $C_6$ to $C_{14}$ aryl group such as a phenyl group, etc.; a lower alkenyl group such as a vinyl group, etc.; a halogen atom such as fluorine, chlorine, bromine, iodine etc.; a hydroxyl group; a $C_1$–$C_6$ linear or branched lower alkoxy group such as a methoxy group, an ethoxy group, an n-propoxy group, an isobutyloxy group, a t-butyloxy group, etc.; a cyano group; a nitro group; an amino group; a $C_1$–$C_6$ linear or branched lower alkylamino group such as a methylamino group, an ethylamino group, an n-propylamino group, an isopropylamino group, an isobutylamino group, a t-butylamino group, etc.; an acylamide group such as a formamide group, an acetamide group, a benzamide group, etc.; a $C_1$–$C_8$ acyl group such as a formyl group, an acetyl group, a propionyl group, an isobutyryl group, a t-butyryl group, a benzoyl group, etc.; an acyloxy group such as a formyloxy group, an acetoxy group, a benzoyloxy group, etc.; a carboxyl group; a $C_1$–$C_6$ linear or branched lower alkoxycarbonyl group such as a methoxycarbonyl group, an ethoxycarbonyl group, an n-propoxycarbonyl group, an isobutyloxycarbonyl group, a t-butyloxycarbonyl group, etc.; an aralkyloxycarbonyl group such as a benzyloxycarbonyl group, a phenetyloxycarbonyl group, etc.; a carbamoyl group, a thiol group, a $C_1$–$C_6$ linear or branched lower alkylthio group such as a methylthio group, an ethylthio group, an n-propylthio group, an isopropylthio group, an isobutylthio group, t-butylthio group, etc.; a sulfonyl group, etc.

The preferable examples of the aryl group of the substituted or unsubstituted aryl group indicated by $R^5$ or $R^6$ in formulae (I) and (I') are a $C_6$ to $C_{14}$ aryl group such as a phenyl group, a naphthyl group, an indenyl group, an anthryl group, etc. The more preferable example is a phenyl group. Further, preferable examples of the substituent group for the aryl group are a $C_1$–$C_6$ linear or branched alkyl group such as a methyl group, an ethyl group, an n-propyl group, an isopropyl group, an isobutyl group and a t-butyl group, etc.; a $C_6$–$C_{14}$ aryl group such as a phenyl group, a naphthyl group, etc.; a halogen atom such as fluorine, chlorine, bromine, iodine, etc., a hydroxyl group, a $C_1$–$C_6$ linear or branched lower alkoxy group such as a methoxy group, an ethoxy group, an n-propoxy group, an isobutyloxy group, a t-butyloxy group, etc.; a cyano group, a nitro group, an amino group, a $C_1$–$C_6$ linear or branched lower alkylamino group such as a methylamino group, an ethylamino group, an n-propylamino group, an isopropylamino group, an isobutylamino group, a t-butylamino group, etc.; an acylamide group such as a formamide group, an acetamide group, a benzamide group, etc.; a $C_1$–$C_8$ acyl group such as a formyl group, an acetyl group, a propionyl group, an isobutyryl group, a t-butyryl group, a benzoyl group, etc.; an acyloxy group such as a formyloxy group, an acetoxy group, a benzoyloxy group, etc.; a carboxyl group; a $C_1$–$C_6$ linear or branched lower alkoxycarbonyl group such as a methoxycarbonyl group, an ethoxycarbonyl group, an n-propoxycarbonyl group, an isobutyloxycarbonyl group, a t-butyloxycarbonyl group, etc.; an aralkyloxycarbonyl group such as a benzyloxycarbonyl group, a phenetyloxycarbonyl group, etc.; a carbamoyl group, a thiol group; a $C_1$–$C_6$ linear or branched lower alkylthio group such as a methylthio group, an ethylthio group, an n-propylthio group, an isopropylthio group, an isobutylthio group, a t-butylthio group, etc.; a sulfonyl group; etc.

Further, preferable examples of the heteroaryl group of the substituted or unsubstituted heteroaryl group indicated by $R^5$ or $R^6$ in formulae (I) and (I') are a monocyclic or polycyclic heteroaryl group having a 5- to 7-member ring including 1 to 4 hetero atoms including an oxygen atom, a nitrogen atom, or a sulfur atom such as a pyrrole group, a furyl group, a thienyl group, an imidazolyl group, a thiazolyl group, a pyridyl group, a pyrimidyl group, a pyridazinyl group, a pyrazyl group, an indolyl group, a quinolyl group, an isoquinolyl group, a benzimidazolyl group, a benzthiazolyl group, a pyrazolyl group, an isooxazolyl group, an isothiazolyl group, an oxadiazolyl group, etc. The examples of preferable substituent groups for the heteroaryl group are a $C_1$–$C_6$ linear or branched alkyl group such as a methyl group, an ethyl group, an n-propyl group, an isopropyl group, an isobutyl group, a t-butyl group, etc.; a $C_6$–$C_{14}$ aryl group such as a phenyl group, a naphthyl group, etc.; a halogen atom such as fluorine, chlorine, bromine or iodine, etc.; a hydroxyl group, a $C_1$–$C_6$ linear or branched lower alkoxy group such as a methoxy group, an ethoxy group, an n-propoxy group, an isobutyloxy group, a t-butyloxy group, etc.; a cyano group, a nitro group, an amino group, a $C_1$–$C_6$ linear or branched lower alkylamino group such as a methylamino group, an ethylamino group, an n-propylamino group, an isopropylamino group, an isobutylamino group, a t-butylamino group, etc.; an acylamide group such as a formamide group, an acetamide group, a benzamide group, etc.; a $C_1$–$C_6$ acyl group such as a formyl group, an acetyl group, a propionyl group, an isobutyryl group, a t-butyryl group, a benzoyl group, etc.; an acyloxy group such as a formyloxy group, an acetoxy group, a benzoyloxy group, etc.; a carboxyl group; a $C_1$–$C_6$ linear or branched lower alkoxycarbonyl group such as a methoxycarbonyl group, an ethoxycarbonyl group, an n-propoxycarbonyl group, an isobutyloxycarbonyl group, a t-butyloxycarbonyl group, etc.; an aralkyloxycarbonyl group such as a benzyloxycarbonyl group, a phenetyloxycarbonyl group, etc.; a carbamoyl group, a thiol group, a $C_1$–$C_6$ linear or branched lower alkylthio group such as a methylthio group, an ethylthio group, an n-propylthio group, an isopropylthio group, an isobutylthio group, t-butylthio group, etc.; a sulfonyl group, etc. The preferable examples of the substituted or unsubstituted heteroaryl group indicated by $R^5$ or $R^6$ are a 4-pyridyl group, a 3-pyridyl group, a 3,5-dichloropyridin-4-yl group, etc.

The preferable examples of the lower alkyl group of the substituted or unsubstituted lower alkyl group indicated by $R^7$ in formula (I) are a $C_1$–$C_6$ linear or branched alkyl group such as a methyl group, an ethyl group, an n-propyl group, an isopropyl group, an isobutyl group, a t-butyl group, etc. The preferable examples of the substituent group for the lower alkyl group are a $C_6$–$C_{14}$ aryl group such as a phenyl group, a lower alkenyl group such as a vinyl group, etc.; a halogen atom such as fluorine, chlorine, bromine or iodine, etc.; a cyano group; a nitro group; an amino group; an acylamide group such as a formamide group, an acetamide group, a benzamide group, etc.; a $C_1$–$C_8$ acyl group such as a formyl group, an acetyl group, a propionyl group, an isobutyryl group, a t-butyryl group, a benzoyl group, etc.; an acyloxy group such as a formyloxy group, an acetoxy group, a benzoyloxy group, etc.; a $C_1$–$C_6$ linear or branched lower alkoxycarbonyl group such as a methoxycarbonyl group, an ethoxycarbonyl group, an n-propoxycarbonyl group, an isobutyloxycarbonyl group, a t-butyloxycarbonyl group, etc.; an aralkyloxycarbonyl group such as a benzyloxy carbonyl group, a phenetyloxycarboxyl group, etc.

The preferable examples of the cycloalkyl group for the substituted or unsubstituted cycloalkyl group indicated by $R^7$ in formula (I) are a $C_3$–$C_6$ cycloalkyl group such as a cyclopropyl group, a cyclobutyl group, a cyclopentyl group, a cyclohexyl group, etc. The preferable examples of the substituent group for the cycloalkyl group are a $C_6$–$C_{14}$ aryl group such as a phenyl group, etc., a lower alkenyl group such as a vinyl group, etc. a halogen atom such as fluorine, chlorine, bromine, iodine, etc., a hydroxyl group, a $C_1$–$C_6$ linear or branched lower alkoxy group such as a methoxy group, an ethoxy group, an n-propoxy group, an isobutyloxy group, a t-butyloxy group, etc.; a cyano group, a nitro group, an amino group, a $C_1$–$C_6$ linear or branched lower alkylamino group such as a methylamino group, an ethylamino group, an n-propylamino group, an isopropylamino group, an isobutylamino group, a t-butylamino group, etc.; an acylamide group such as a formamide group, an acetamide group, a benzamide group, etc.; a $C_1$–$C_6$ acyl group such as a formyl group, an acetyl group, a propionyl group, an isobutyryl group, a t-butyryl group, a benzoyl group, etc.; an acyloxy group such as a formyloxy group, an acetoxy group, a benzoyloxy group, etc.; a carboxyl group; a $C_1$–$C_6$ linear or branched lower alkoxycarbonyl group such as a methoxycarbonyl group, an ethoxycarbonyl group, an n-propoxycarbonyl group, an isobutyloxycarbonyl group, a t-butyloxycarbonyl group, etc.; an aralkyloxycarbonyl group such as a benzyloxycarbonyl group, a phenetyloxycarbonyl group, etc.; a carbamoyl group, a thiol group, a $C_1$–$C_6$ linear or branched lower alkylthio group such as a methylthio group, an ethylthio group, an n-propylthio group, an isopropylthio group, an isobutylthio group, t-butylthio group, etc.; a sulfonyl group, etc.

The specific examples of the 1-cycloalkyl-1,8-naphthyridin-4-one derivative described in the above formula (I) or (I') of the present invention are as follows.

(a) a 1-cycloalkyl-1,8-naphthyridin-4-one derivative where all of $R^2$, $R^3$, and $R^4$ are hydrogen atoms;

(b) a 1-cycloalkyl-1,8-naphthyridin-4-one derivative where $R^1$ is a substituted or unsubstituted cyclohexyl group.

(c) a 1-cycloalkyl-1,8-naphthyridin-4-one derivative where $R^1$ is a substituted or unsubstituted cyclopentyl group.

(d) a 1-cycloalkyl-1,8-naphthyridin-4-one derivative where $R^1$ is a substituted or unsubstituted cyclobutyl group.

(e) a 1-cycloalkyl-1,8-naphthyridin-4-one derivative where $R^1$ is a substituted or unsubstituted cyclopropyl group.

(f) a 1-cycloalkyl-1,8-naphthyridin-4-one derivative where $R^1$ is a substituted or unsubstituted 5- or 6-membered heterocycloalkyl group containing one oxygen or sulfur atom.

(g) a 1-cycloalkyl-1,8-naphthyridin-4-one derivative where $R^1$ is a substituted or unsubstituted 5- or 6-membered heterocycloalkyl group containing the same or different two hetero atoms consisting of oxygen, sulfur and nitrogen atoms.

(h) a 1-cycloalkyl-1,8-naphthyridin-4-one derivative where $R^1$ is a substituted or unsubstituted azetidinyl group.

(i) a 1-cycloalkyl-1,8-naphthyridin-4-one derivative where $R^1$ is a substituted or unsubstituted pyrrolidinyl group.

(j) a 1-cycloalkyl-1,8-naphthyridin-4-one derivative where $R^1$ is a substituted or unsubstituted piperidyl group.

(k) a 1-cycloalkyl-1,8-naphthyridin-4-one derivative where $R^1$ is a substituted or unsubstituted tetrahydrofuryl group.

(l) a 1-cycloalkyl-1,8-naphthyridin-4-one derivative where either one of $R^5$ or $R^6$ is a hydrogen atom.

(m) a 1-cycloalkyl-1,8-naphthyridin-4-one derivative where one of $R^5$ or $R^6$ is a substituted or unsubstituted phenyl group and the other is a hydrogen atom.

(n) a 1-cycloalkyl-1,8-naphthyridin-4-one derivative where one of $R^5$ or $R^6$ is a pyridyl group and the other is a hydrogen atom.

(o) a 1-cycloalkyl-1,8-naphthyridin-4-one derivative where one of $R^5$ or $R^6$ is a 4-pyridinyl group and the other is a hydrogen atom.

(p) a 1-cycloalkyl-1,8-naphthyridin-4-one derivative where one of $R^5$ or $R^6$ is a 3,5-dichloropyridin-4-yl group and the other is a hydrogen atom.

The compounds of the present invention include those having one or more asymmetric carbon atoms. Based on this, there are optical isomers such as (R)-isomers, (S)-isomers, racemics, diastereomers, etc. Further, depending on the types of the substituent groups, there are double bonds, and therefore, there are also geometrical isomers such as (Z)-isomers, (E)-isomers, etc. The present invention includes these isomers separated from each other or in mixtures.

The compounds of the present invention include those capable of forming salts with acids. As the salts, acid addition salts with a mineral acid such as hydrochloric acid, a hydrobromic acid, a hydroiodic acid, a sulfuric acid, a nitric acid, a phosphoric acid, and with an organic acid such as a formic acid, an acetic acid, a propionic acid, an oxalic acid, a malonic acid, a succinic acid, a fumaric acid, a maleic acid, a lactic acid, a malic acid, a citric acid, a tartaric acid, a picric acid, a methanesulfonic acid, a trichloroacetic acid, a trifluoroacetic acid, an asparatic acid, a glutamic acid. Further, the compounds of the present invention can be isolated as a hydrate, solvates with, for example, ethanol, isopropanol, or various crystalline substances in the various crystalline forms.

The compound of formula (I) or (I') according to the present invention may be synthesized by, for example, the following method.

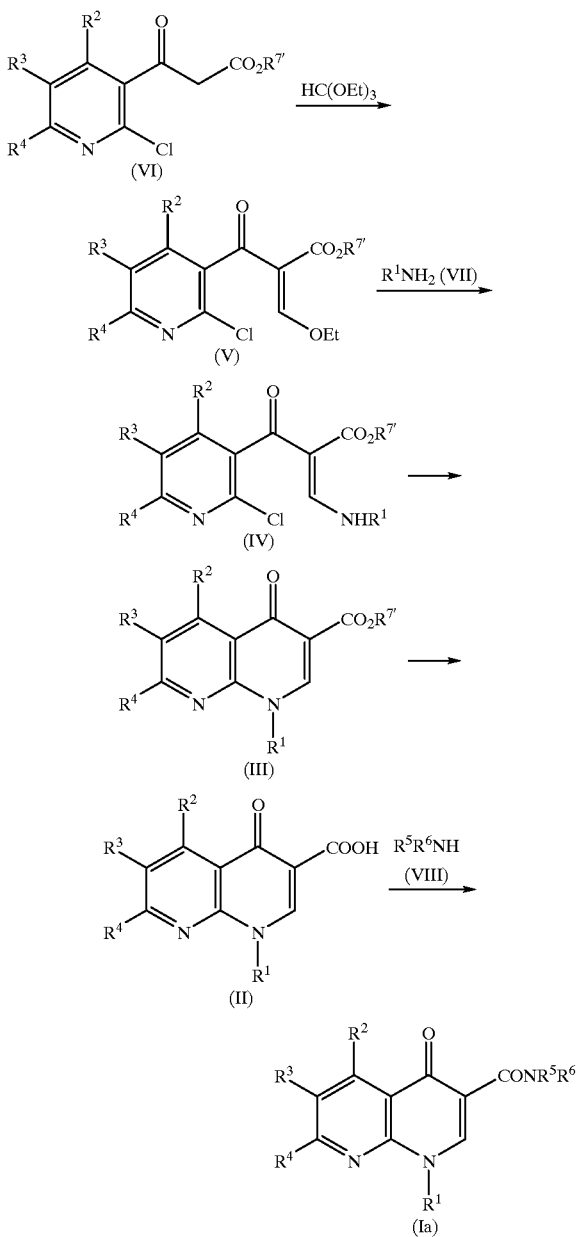

wherein, $R^1$, $R^2$, $R^3$, $R^4$, $R^5$ and $R^6$ are as defined above and $R^{7'}$ indicates $R^7$ as defined above except for a hydrogen atom, or a protective group of the carboxylic acid such as a benzyl group, an allyl group, etc.

To carry out the present method, a compound (V) is obtained from the compound (VI) according to a known method (for example, J. Med. Chem. 1986, 29, 2363, ibid. 1985, 28, 1558). This reaction causes 1 to 3 equivalents, preferably 1.5 equivalents, based upon the compound (VI), of a trialkylformate such as triethylformate etc. to act on the compound (VI) in 10 to 20 equivalents of acetic anhydride at 100 to 140° C. and distills off the solvent after the end of the reaction so as to obtain the desired compound (V). If necessary, the resultant product may be purified by vacuum distillation, etc.

Note that the starting material, that is, the compound (VI), is either a known compound or is obtained from 2-chloronicotinic acid, 2,6-dichloronicotinic acid, 2-chloro-6-methylnicotinic acid, or the like with monoethylmalonate magnesium salt according to a known method (for example, J. Med. Chem. 1986, 29, 2363).

It is possible to obtain the compound (IV) from the compound (V) obtained according to a known method (for example, J. Med. Chem. 1986, 29, 2363, ibid. 1985, 28, 1558). One equivalent, with respect to the compound (V), of a commercially available (or known) primary cycloalkylamine or heterocycloalkylamine (VII) (for example, aminocyclopentane, aminocyclohexane, aminoazetidine, aminopyrrolidine, aminopiperidine, aminotetrahydrofuran etc.) is used in a halogenated hydrocarbon such as methylene chloride etc. or an aromatic hydrocarbon such as toluene, benzene, etc. or ether such as diethyl ether, tetrahydrofuran, etc. or a mixture thereof at 0° C. to room temperature. After the end of the reaction, the resultant product is diluted with an organic solvent, which is not miscible with water, then is successively washed with water and saturated saline. The solvent is then distilled off, whereupon it is possible to obtain the desired compound (IV). If necessary, the resultant product may be purified by column chromatography etc.

The compound (IV) obtained may be processed by a known method (for example, J. Med. Chem. 1986, 29, 2363, ibid. 1985, 28, 1558) to obtain a compound (III). 1 to 1.2 equivalents, based on the compound (IV), of an alkali metal hydride such as sodium hydride, potassium hydride, etc., or strong base such as lithium diisopropylamide, lithium hexamethyldisilazane, etc., preferably sodium hydride, is used in a halogenated hydrocarbon such as methylene chloride, etc., an aromatic hydrocarbon such as toluene, benzene, etc., or an ether such as diethyl ether, tetrahydrofuran, etc., or a mixture thereof at 0° C. to room temperature. After the end of the reaction, the resultant product is diluted with an organic solvent, which is not miscible with water, then is successively washed with water and saturated saline. The solvent is then distilled off, whereupon it is possible to obtain the desired compound (III). If necessary, the resultant product may be purified by column chromatography etc.

The compound (III) thus obtained is hydrolyzed according to a known method to obtain a compound (II). The method differs depending on the $R^{7'}$, but normally can be performed under basic conditions (for example, J. Med. Chem. 1984, 27, 292) or acidic conditions (J. Med. Chem. 1986, 29, 2363).

Under basic conditions, 1 to 1.2 equivalents, based upon the compound (III), of alkali metal hydroxide such as sodium hydroxide, potassium hydroxide, etc., is used in water or an alcohol such as ethanol, methanol, etc. or ether such as diethyl ether, tetrahydrofuran, dioxane, etc., or a mixture thereof at room temperature to 60° C. After the end of the reaction, the reaction solution is made weakly acidic, is diluted with an organic solvent, which is not miscible with water, and is successively washed with water and saturated saline. The solvent is then distilled off to obtain the desired compound (II). If necessary, the resultant product may be purified by recrystallization etc. Under acidic conditions, an acid catalyst such as sulfuric acid, hydrogen chloride, etc., is made to act in water or an alcohol such as ethanol, methanol, or an ether such as diethyl ether, tetrahydrofuran, dioxane, or a mixture thereof at 60° C. to 100° C. After the end of the reaction, the solvent is distilled off to obtain the desired compound (II). If necessary, the resultant product may be purified by recrystallization etc.

When employing a special substituent group as a protective group of the carboxylic acid in $R^{7'}$ of formula (IV), it is also possible to convert the substance to the compound (II)

by that substituent group under neutral conditions. For example, when employing a benzyl group in $R^{7'}$, it is possible to convert the substance to the compound (II) by hydrogenolysis under neutral conditions. When an allyl group is employed in $R^{7'}$, it is possible to convert it to the compound (II) by formic acid in the presence of a Pd(O) complex.

The compound (II) obtained can be used to obtain the compound (Ia) in the compounds having the formula (I) of the present invention where X is the group $NR^5R^6$ according to a known method (Fourth Experimental Chemical Seminar, vol. 22, p. 137, published by MARUZEN). The reaction synthesizes an acid amide from a carboxylic acid (II) and commercially available or known amine component (VIII) (for example, methylamine, ethylamine, isopropylamine, benzylamine, phenylethylamine, aniline, tollylamine, aminobenzoic acid, aminoacetophenone, dichloroaniline, aminonaphthalene, aminopyridine, aminodichloropyridine, aminofluoropyridine, phenylenediamine, diaminopyridine, nitroaniline, etc.). This may be done by various methods, but these may be roughly divided into three groups. The first is a method where a condensation agent such as dicyclohexyl carbodiimide, carbonyl diimidazole, is used to cause a reaction between a carboxylic acid (II) and an amine component (VIII). The second is a method where a carboxylic acid (II) is converted to an acid halide, then allowed to react with an amine component (VIII). The third is a method where carboxylic acid (II) is converted to an acid anhydride, then allowed to react with an amine component (VIII).

For example, as a method passing through an acid halide, 1 to 5 equivalents, based upon the carboxylic acid (II), of an acid halogenating agent such as thionyl chloride, phosphorus pentachloride, is used in an aromatic hydrocarbon such as toluene, benzene, an ether such as tetrahydrofuran, 1,4-dioxane, or a mixture thereof or without using a solvent at room temperature to 100° C. After the end of the reaction, the solvent is distilled off to obtain the acid halide. The acid halide may be used directly, without purifying, for the next reaction. 2 to 3 equivalents, based on the acid halide, of the amine component (VIII) is reacted in a halogenated hydrocarbon such as methylene chloride, etc., an aromatic hydrocarbon such as toluene, benzene, etc., an ether such as diethyl ether, etc., or a mixture thereof at 0° C. to room temperature, or 1 to 1.5 equivalents of the amine component (VIII) is reacted in the presence of 1 to 3 equivalents of a tertiary amine such as triethylamine, diisopropylethylamine, etc., or the amine component (VIII) may be reacted with the acid halide component after reacting with an alkali metal hydride such as sodium hydride or potassium hydride, etc. to form the corresponding amine metal salt. After the end of the reaction, the substance is diluted with an organic solvent which is not miscible with water, then is successively washed with water and saturated saline. The solvent is then distilled off to obtain the desired compound (Ia). If necessary, the product may be purified by column chromatography, recrystallization, etc.

In the process of the present invention, it was possible to introduce $R^1$ substituent group, which was difficult to be introduced according to the above-mentioned method of Kaminsky et al., by the use thereof in the form of the amine component (VIII).

The type IV phosphodiesterase inhibiting activities of the compounds according to the present invention were confirmed by the following test:

(1) Method of Measurement of Type IV Phosphodiesterase Inhibiting Activity

The following assay was used to evaluate the ability of the compound of the present invention to suppress type IV phosphodiesterase, according to Biochemical. Pharmacol. 48 (6), 1219–1223 (1994).

1) Type IV phosphodiesterase activity fractions were prepared as follows. Namely, human histiocytic lymphoma cell line U937 was cultured in an RPMI1640 medium containing 10% fetal calf serum to obtain $10^9$ cells of U937. The cells were recovered by centrifugation and suspended in 40 ml of buffer A (20 mM bis-tris, 5 mM 2-mercaptoethanol, 2 mM benzamidine, 2 mM EDTA, 0.1 mM 4-(2-aminoethyl) benzensulfonyl hydrochloride, 50 mM sodium acetate, pH=6.5). The cells were broken by a sonication and centrifuged (4° C., 10,000 G, 10 minutes) to obtain a supernatant. This was filtered by a 0.45 µm filter to obtain the soluble fraction.

2) The soluble fraction obtained was applied into a 1×10 cm DEAE Sepharose column equalibrated with the buffer A. 120 ml of the buffer A containing a linear gradient solution of 0.05 to 1M sodium acetate was used to separate the phosphodiesterase and recover 24 5-ml fractions. Each of the fractions was measured for the cAMP phosphodiesterase activity. The fractions having cAMP phosphodiesterase activity which could be inhibited by 30 µM rolipram (selective type IV phosphodiesterase inhibitor) were collected and used as a stored solution for examination of the type IV phosphodiesterase inhibiting activity.

3) The test compound was reacted at a desired concentration in a reaction mixture containing 20 mM tris-HCl (pH 7.5), 1 mM $MgCl_2$, 100 µM EDTA, 330 µg/ml calf serum albumin, 10 µg/ml 5'-nucleotidase, 0.4 µCi $^3$H-cAMP (0.28 µM cAMP) and the type IV phosphodiesterase stored solution at 30° C. for 30 minutes. QAE-Sephadex suspended in 10 mM of hepes-Na (pH –7.0) was added to the reaction mixture which was then allowed to stand for 5 minutes, then the supernatant was obtained, QAE-Sephadex was further added, to the supernatant, and was allowed to stand for 5 minutes, then the supernatant was obtained and measured for radioactivity.

4) The $IC_{50}$ was measured for each compound as the concentration of the test compound inhibiting 50% of the type IV phosphodiesterase activity.

(2) Type IV Phosphodiesterase Inhibiting Activity of Various Compounds

The phosphodiesterase inhibiting activity $IC_{50}$ obtained by the above method of measurement is shown in the following Table I. Further, the inhibiting activity of the typical control agent for a type IV phosphodiesterase inhibitor, Rolipram (Tocris) was measured in the same way and the $IC_{50}$ obtained is shown in Table I.

Further, as a Comparative Example, the compound N-(2-(4-pyridyl)ethyl)-1-ethyl-7-methyl-1,8-naphthyridin-1,4-dihydro-4-one-3-carboxyamide described in WO-A-97-04775 (1997), page 17, Example 1 was synthesized and measured similarly for inhibiting activity. The phosphodiesterase inhibiting activity $IC_{50}$ obtained is shown in Table I.

TABLE I

| Example | PDEIV-$IC_{50}$ (µM) |
|---------|----------------------|
| 4       | 0.06                 |
| 9       | 0.023                |
| 10      | 0.0015               |
| 11      | 0.0017               |
| 16      | 0.054                |

TABLE I-continued

| Example | PDEIV-IC$_{50}$ ($\mu$M) |
|---|---|
| 17 | 0.0048 |
| 18 | 0.0047 |
| 19 | 0.0063 |
| 20 | 0.012 |
| 25 | 0.0009 |
| 26 | 0.0009 |
| 27 | 0.0013 |
| 28 | 0.0078 |
| 32 | 2.2 |
| 33 | 2.0 |
| 34 | 0.024 |
| 38 | 0.33 |
| 39 | 0.01 |
| 43 | 0.19 |
| 44 | 0.0027 |
| 46 | 0.013 |
| 47 | 0.04 |
| 48 | 0.0048 |
| 49 | 0.022 |
| 50 | 0.10 |
| 51 | 0.043 |
| 55 | 0.0067 |
| 56 | 0.0016 |
| 61 | 0.18 |
| 62 | 0.0023 |
| 69 | 0.21 |
| 70 | 0.0039 |
| 71 | 0.0005 |
| 72 | 0.11 |
| 79 | 0.0012 |
| 86 | 0.14 |
| 92 | 0.0021 |
| 93 | 0.069 |
| 100 | 0.043 |
| 101 | 0.0004 |
| 102 (Sulfoxide) | 0.0051 |
| 102 (Sulfon) | 0.016 |
| 106 | 0.14 |
| 107 | 0.0004 |
| 113 | 0.40 |
| 115 | 0.21 |
| 117 | 0.0037 |
| 118 | 0.0013 |
| 119 | 0.0010 |
| 120 | 0.0027 |
| 122 | 0.20 |
| 123 | 0.39 |
| 126 | 0.72 |
| 127 | 0.0072 |
| 128 | 0.0057 |
| 129 | 0.0093 |
| 130 | 0.050 |
| 133 | 0.0073 |
| 135 | 0.0045 |
| 139 | 0.24 |
| 140 | 0.0025 |
| 144 | 0.12 |
| 145 | 0.0083 |
| 149 | 0.041 |
| 150 | 0.0003 |
| 156 | 0.15 |
| 157 | 0.13 |
| 159 | 0.004 |
| 162 | 0.006 |
| 164 | 0.4 |
| 168 | 1.5 |
| 170 | 0.99 |
| 172 | 0.36 |
| 174 | 0.13 |
| 176 | 0.92 |
| 178 | 3.3 |
| 180 | 4.5 |
| 184 | 2.3 |
| 192 | 0.0041 |
| 194 | 0.96 |
| 197 | 0.0062 |
| Comp.Ex. | 5.20 |
| Rolipram | 0.46 |

As a result of the test on the phosphodiesterase inhibiting activity, it was confirmed that the 1-cycloalkyl-1,8-naphthyridin-4-one derivative according to the present invention exhibited an excellent inhibitory effect.

The inhibitory activities of the compound of the present invention on TNF-α production by LPS stimulated macrophages were confirmed by the following test:

(1) Method of Measurement of TNF-α Production Inhibitory Activity by LPS Stimulated Macrophages The following assay was used to evaluate the ability of the compound of the present invention to suppress TNF-α production by LPS stimulated macrophages according to Immunopharmacol. 29, 121–127 (1995).

1) 6 to 10 week old female BALB/c mice were used, 2 ml portions of thioglycolate were intraperitoneally administered, and the abdominal cavities were washed by 10 ml of PBS after 4 days, whereby 1 to $2\times10^7$ peritoneal cells were obtained per mouse. These were suspended in a hemocyte solution (0.75% ammonium chloride, 17 mM tris-hydrochlorate buffer, pH7.2), centrifuged, then resuspended in an RPMI1640 medium including 10% fetal calf serum and seeded in a 96-well cell culture plate at a density of $1\times10^5$ cells/50 $\mu$l/well. Since these cells adhered strongly to the tissue culture plate and were positive in nonspecific esterase staining, they were used for the test as mouse peritoneal macrophages. Mouse peritoneal macrophages were precultured overnight at 37° C. in 50% $CO_2$ for the experiment.

2) E. Coli (serum type 055:B5) derived LPS was dissolved in PBS in a concentration of 1 mg/ml, then sterilized by filtration. The test compound was dissolved in DMSO to make a 1000-fold concentration solution of the final concentration of use. 10 $\mu$l of the above LPS stock solution (final concentration 10 $\mu$g/ml) and 1 $\mu$l of the tested substance stock solution were added and mixed in 0.5 ml of RPMI1640 medium containing 10% fetal calf serum. This was added to the above cells at 50 $\mu$l/well and cultured for 8 hours. The cultured supernatant was recovered from each well and the TNF-α concentration was measured by the ELISA method (Cytoscreen® Immunoassay Kit Mouse TNF-α, BioSourse International).

3) The IC$_{50}$ was calculated for each compound as the concentration of the test compound inhibiting 50% of the TNF-α production caused by LPS stimulus.

(2) TNF-α Production Inhibitory Activity by LPS Stimulated Macrophages

The IC$_{50}$ values for the TNF-α production inhibitory activity obtained by the above method are shown in the following Table II. The comparative example was the compound described in WO-A-97-04775, Example 1, mentioned above.

TABLE II

| Example | TNF-α production inhibitory activity IC$_{50}$ ($\mu$M) |
|---|---|
| 9 | 0.1 |
| 10 | 0.01 |
| 11 | 0.004 |
| 16 | 0.3 |
| 17 | 0.01 |
| 18 | 0.001 |
| 19 | 0.007 |
| 20 | 3.0 |
| 25 | 0.0004 |
| 26 | 0.0002 |
| 27 | 0.01 |
| 28 | 0.1 |
| 32 | 4.0 |
| 33 | 5.0 |
| 34 | 0.08 |
| 39 | 5 |
| 43 | 2.5 |
| 44 | 0.01 |
| 46 | 0.5 |
| 47 | 0.8 |
| 48 | 1.5 |
| 49 | 0.2 |
| 50 | 7 |
| 51 | 0.05 |
| 55 | 0.01 |
| 56 | 0.015 |
| 86 | 3 |
| 92 | 0.07 |
| 93 | 2 |
| 100 | 0.07 |
| 101 | 0.003 |
| 102 (Sulfoxide) | 0.070 |
| 102 (Sulfon) | 0.20 |
| 106 | 0.09 |
| 107 | 0.003 |
| 113 | 0.3 |
| 117 | 0.002 |
| 119 | 0.00004 |
| 120 | 0.0007 |
| 122 | 1.2 |
| 123 | 1.2 |
| 126 | 1.8 |
| 127 | 0.015 |
| 139 | 0.37 |
| 140 | 0.010 |
| 149 | 0.078 |
| Comp.Ex. | 10.0 |
| Rolipram | 0.1 |

From the above results, it was confirmed that the 1-cycloalkyl-1,8-naphthylidin-4-one derivative of the present invention exhibits an excellent activity inhibiting the production of TNF-α.

The compound of the present invention is useful as a pharmaceutical composition for the prevention or treatment of bronchial asthma, chronic bronchitis, and other respiratory diseases, diseases relating to abnormality of the nervous system such as Alzheimer's Disease, Parkinson's Disease, diseases relating to mental abnormalities such as maniac depression, inflammatory diseases such as atopic dermitis and acquired immunity disorder syndrome, general or local joint diseases such as osteoarthritis, rheumatoid arthritis, sepsis, endotoxin shock and other diseases related to tumor necrosis factor (TNF-α) or other various cytokine (IL-1, IL-6, etc.), and the like by selectively inhibiting the type IV phosphodiesterase and further inhibiting the production of TNF-α.

The type IV phosphodiesterase inhibitor of the present invention is useful as an agent for the prevention or treatment of specifically respiratory diseases (for example, bronchial asthma, chronic bronchitis, pneumonia type diseases, adult respiratory distress syndrome, etc.), diseases relating to abnormality of the nervous system (for example, impaired learning, memory, and recognition relating to Alzheimer's Disease, Parkinson's Disease, and the like, multiple lateral sclerosis, senile dementia, amyotrophic lateral sclerosis, muscular distrophy, etc.), diseases relating to mental abnormalities (for example, maniac depression, schizophrenia, neurosis, etc.), inflammatory diseases (for example, atopic dermitis, conjunctivitis, acquired immunity disorder syndrome, keloids, etc.), general and local joint diseases (for example, osteoarthritis, gouty arthritis, rheumatoid arthritis, no dose rheumatism, etc.), tumor necrosis factor (TNF) and other cytokine (IL-1, IL-6, etc.) related diseases (for example, psoriasis, rheumatoid arthritis, Crohn disease, septicemia, septic shock, endotoxic shock, nephritis, pneumonia, bacterial or viral infection, cardiac incompetence, ateriosclerosis, cardiac infarction, etc.) etc.

For use of the effective ingredient of the present invention as a pharmaceutical or a type IV phosphodiesterase inhibitor, one or more types of the compound of the present invention may be formulated and formed into preparations suitable for the method of administration according to ordinary methods. For example, for oral administration, capsules, tablets, granules, powders, syrups, dry syrups, and other preparations may be mentioned, while for nonoral administration, injections and also rectal suppositories, vaginal suppositories, and other suppositories, sprays and other nasal agents, ointments, transdermal absorption type tapes, and other transdermal absorption agents may be mentioned.

The clinical dosage of the compound of the present invention differs depending on the symptoms, the severity of the disease, the age, and complications of the patient to which the compound is being administered and differs depending on the preparation as well, but in the case of oral administration is normally 1 to 1000 mg, preferably 1 to 500 mg, more preferably 5 to 100 mg. per adult per day as effective ingredient, and in the case of nonoral administration is one-tenth to one-half of the case of oral administration. The dosage may be suitably adjusted according to the age, symptoms, etc. of the patient.

The compound of the present invention is a selective inhibitor for type IV phosphodiesterase and has over 10-times the selectivity over other phosphodiesterase isoenzymes (i.e., PDE I–III, V and VII). Due to this, it is expected that there will be few side effects due to the action of inhibiting other phosphodiesterase isoenzymes.

Further, the compounds of the present invention are low in toxicity, and these compounds are expected to be high in safety. For example, the compounds of Examples 10, 11, 25, 26, 34, 56, 106, 117, 120, 127 and 139 exhibited no death when 10 mg/kg per day was intraperitotoneally administered for 5 weeks to mice.

The 1-cycloalkyl-1,8-naphthyridin-4-one derivative or its pharmaceutically acceptable salt or solvate of the present invention is useful as a pharmaceutical composition for the prevention or treatment of diseases involving type IV phosphodiesterase. As specific examples of diseases involving type IV phosphodiesterase, for example, respiratory diseases (for example, bronchial asthma, chronic bronchitis, pneumonia type diseases, adult respiratory distress, etc.), diseases relating to abnormality of the nervous system (for example, impaired learning, memory, and recognition relating to Alzheimer's Disease, Parkinson's Disease, and the like, multiple lateral sclerosis, senile dementia, amyotrophic lateral sclerosis, muscular distrophy, etc.), diseases relating to mental abnormalities (for example, maniac depression, schizophrenia, neurosis, etc.), inflammatory diseases (for example, atopic dermitis, conjunctivitis, acquired immunity disorder syndrome, keloids, etc.), general and local joint diseases (for example, osteoarthritis, gouty arthritis, rheumatoid arthritis, no dose rheumatism, etc.), tumor necrosis factor (TNF) and other cytokine (IL-1, IL-6, etc.) related diseases (for example, psoriasis, rheumatoid arthritis, Crohn disease, septicemia, septic shock, endotoxic shock, nephritis, pneumonia, bacterial or viral infection, cardiac incompetence, ateriosclerosis, cardiac infarction, etc.) etc. may be mentioned.

EXAMPLES

The present invention will now be further explained in detail by, but is by no means limited to, the following Examples.

Example 1

Synthesis of (±)-ethyl 3-(1-methoxycarbonylpyrrolidin-3-ylamino)-2-(2-chloronicotinoyl)acrylate A mixed solution of 385 mg (1.69 mmol) of ethyl(2-chloronicotinoyl)acetate, 1.91 ml (20.3 mmol) of acetic anhydride and 422 µl (2.54 mmol) of triethylformate was heated and stirred under an argon atmosphere at 120° C. for 1.5 hours. The solution was cooled, then the excess reactants were distilled off under vacuum to obtain ethoxy acrylate. Thereafter, to a 5 ml methylene chloride solution of the ethoxy acrylate, a 2 ml anhydrous methylene chloride solution of (±)-3-amino-1-methoxycarbonylpyrrolidine was added at 0° C., and the solution was further stirred at room temperature for 30 minutes and then, the solvent was distilled off under vacuum. The residue was purified by silica gel column chromatography (hexane/ethyl acetate=2/1) to obtain 425 mg (66%) of the above-identified compound as a slightly yellow oily substance.

IR(KBr)cm$^{-1}$: 2961, 1687, 1639, 1614, 1561, 1458, 1394. MS (FAB) 382[M+H]$^+$. $^1$-NMR(CDCl$_3$): δ 0.79 and 0.93 (total 3H, t, J=7.2 Hz) 2.02–2.18(1H, m) 2.28–2.40(1H, m) 3.41–4.05(6H, s) 3.73(3H, s) 4.11–4.21(1H, m) 7.24–7.30 (1H, m) 7.52 and 7.57 (total 1H, dd, J=1.9 and 7.4 Hz) 8.19–8.33(1H, m) 8.38(1H, dd J=1.9 and 4.9 Hz).

Example 2

Synthesis of (±)-ethyl 1-(1-methoxycarbonylpyrrolidin-3-yl)-1,4-dihydro[1,8]naphthyridin-4-one-3-carboxylate 45 mg of sodium hydride (abt. 60% oil suspension 1.13 mmol) was added to 5 ml of a tetrahydrofuran solution of 411 mg of the compound obtained in Example 1 (1.08 mmol) under an argon atmosphere at 0° C. and the solution was stirred at the same temperature for 5 minutes. It was further stirred at room temperature for 30 minutes, then water (15 ml) was added and extraction was performed with ethyl acetate (30 ml). Next, the organic layer was washed with saturated saline (10 ml), then dried over anhydrous sodium sulfate, then the solvent was distilled off under vacuum. The precipitated crystal was washed with diethyl ether and the crystal was obtained by filtration to obtain 314 mg (84%) of the above-identified compound as a colorless crystal.

IR(KBr)cm$^{-1}$: 2984, 1735, 1699, 1633, 1832. MS(FAB) 346[M+H]$^+$. $^1$H-NMR(CDCl$_3$): δ 1.41(3H, t, J=7.1 Hz) 2.25–2.57(2H, m) 3.53–3.79(3H, m) 3.76(3H, s) 3.92–4.13 (1H, m) 4.40(2H, q, J=7.1 Hz) 5.96–6.12(1H, m) 7.43(1H, dd, J=4.5 and 7.8 Hz) 8.66(1 H, s) 8.73(1H, dd, J=1.8 and 4.5 Hz) 8.80(1H, dd, J=1.8 and 7.8 Hz).

Example 3

Synthesis of (±)-1-(1-methoxycarbonylpyrrolidin-3-yl)-1,4-dihydro[1,8]naphthyridin-4-one-3-carboxylic acid To a mixed solution of 269 mg (0.78 mmol) of the compound obtained in Example 2 in 3 ml of tetrahydrofuran and 3 ml of ethanol, 857 µl (0.857 mmol) of 1N sodium hydroxide solution was added at room temperature and the solution was stirred at that temperature for 1.5 hours. Next, this was diluted with water (20 ml) and, after washing with ether (10 ml), 1N hydrochloric acid (0.87 ml) was added to an aqueous layer. After extracting with methylene chloride (40 ml), the extract was dried over anhydrous sodium sulfate, then the solvent was distilled off under vacuum. Thus, 237 mg (96%) of the above-identified compound was obtained as a slightly yellow crystal.

MS(FAB) 318[M+H]$^+$. $^1$H-NMR(CDCl$_3$): δ 2.36–2.65 (2H, m) 3.60–3.87(3H, m) 3.76(3H, s) 4.06–4.15(1H, m) 6.13–6.23(1H, m) 7.59(1H, dd, J=4.5 and 8.0 Hz) 8.85(1H, dd, J=2.0 and 8.0 Hz) 8.90(1H, dd, J=2.0 and 4.5 Hz) 8.95(1H, s) 14.27(1H, brs).

Example 4

Synthesis of (±)-N-(2,6-dichlorophenyl)-1-(1-methoxycarbonylpyrrolidin-3-yl)-1,4-dihydro[1,8] naphthyridin-4-one-3-carboxamide To a 2 ml anhydrous tetrahydrofuran solution of 63.5 mg (0.2 mmol) of the compound obtained in Example 3, 29.2 µl (0.4 mmol) of thionyl chloride was added at room temperature and heated under reflux for 1.5 hours and the solvent was distilled off under vacuum to obtain the acid chloride as a slightly yellow oily substance. To a 2 ml methylene chloride solution of this acid chloride, 83.6 µl (0.6 mmol) of triethylamine and 38.9 mg (0.24 mmol) of 2,6-dichloroaniline was added at room temperature and was stirred at 50° C. for 1.5 hours. The reaction mixture was diluted with ethyl acetate (20 ml) and successively washed with water (5 ml) and saturated saline (5 ml), then dried over anhydrous sodium sulfate and the solvent was distilled off under vacuum. The residue was purified by a silica gel chromatography (hexane/ethylacetate=1/2) to obtain 83 mg (90%) of the above-identified compound as a slightly yellow oily substance.

IR(KBr)cm$^{-1}$: 2954, 1702, 1682, 1614, 1486. MS(FAB) 461[M+H]$^+$. $^1$H-NMR(CDCl$_3$): δ 2.42–2.58(2H, m) 3.58–3.69(2H, m) 3.73 (3H, s) 3.74–3.88(1H, m) 4.06–4.15 (1H, m) 6.08–6.18(1H, m) 7.19(1H, t, J=8.2 Hz) 7.40(2H, d, J=8.2 Hz) 7.53(1H, dd, J=4.5 and 8.0 Hz) 8.83(1H, dd, J=1.9 and 4.5 Hz) 8.89(1H, dd, J=1.9 and 7.9 Hz) 9.10(1H, brs) 11.57(1H, brs).

Example 5

Synthesis of (S)-ethyl 3-(1-benzyloxycarbonylpyrrolidin-3-ylamino)-2-(2-chloronicotinoyl)acrylate The same reaction was carried out as in Example 1, except for using (S)-3-amino-1-benzyloxycarbonylpyrrolidine, instead of (±)-3-amino-1-methoxycarbonylpyrrolidine, to obtain 2.65 g (88%) of the above-identified compound as a slightly yellow oily substance.

IR(KBr)cm$^{-1}$: 2974, 1703, 1636, 1394, 1323. MS(FAB) 458[M+H]$^+$. $^1$H-NMR(CDCl$_3$): δ 0.79 and 0.92(total 3H, t, J=7.1 Hz) 2.02–2.18(1H, m) 2.29–2.40(1H, m) 3.40–3.71 (3H, m) 3.78–4.01(2 H, m) 4.08–4.21(1H, m) 5.08–5.20(2H, m) 7.21–7.41 (6H, m) 7.49–7.58(1H, m) 8.18–8.32(1H, m) 8.35–8.40(1H, m) 9.61–9.75(0.2H, m) 11.08–11.22(0.8H, m).

Example 6

Synthesis of (S)-ethyl 1-(1-benzyloxycarbonylpyrrolidin-3-yl)-1,4-dihydro[1,8]naphthyridin-4-one-3-carboxylate The same reaction was carried out as in Example 2, except for using (S)-ethyl 3-(1-benzyloxycarbonylpyrrolidin-3-ylamino)-2-(2-chloronicotinoyl)acrylate, instead of (±)-ethyl 3-(1-methoxycarbonylpyrrolidin-3-ylamino)-2-(2-chloronicotinoyl)acrylate, to obtain 2.29 g (95%) of the above-identified compound as s slightly yellow crystal.

IR(KBr)cm$^{-1}$: 2959, 2894, 1698, 1646, 1415, 1334, 1201. MS (FAB) 422[M+H]$^+$. $^1$H-NMR(CDCl$_3$): δ 1.40(3H, t, J=7.1 Hz) 2.32–2.43(1H, m) 2.45–2.59(1H, m) 3.61–3.87 (3H, m) 4.04–4.13(1H, m) 4.39(2H, q, J=7.1 Hz) 5.14–5.22 (1H, m) 6.02–6.12 (1H, m) 5.27–5.45(6H, m) 8.67(1H, s) 8.72(1H, dd, J=2.0 and 4.5 Hz) 8.80(1H, dd, J=2.0 and 7.8 Hz).

Example 7

Synthesis of (S)-1-(1-benzyloxycarbonylpyrrolidin-3-yl)-1,4-dihydro[1,8]naphthyridin-4-one-3-carboxylic acid The same reaction was carried out as in Example 3, except for using (S)-ethyl 1-(1-benzylcarbonylpyrrolidin-3-yl)-1,4-dihydro[1,8]naphthyridin-4-one-3-carboxylate, instead of (±)-ethyl 1-(1-methoxycarbonylpyrrolidin-3-yl)-1,4-dihydro[1,8]naphthyridin-4-one-3-carboxylate, to obtain 1.79 g (99%) of the above-identified compound as a slightly yellow crystal.

$^1$H-NMR(CDCl$_3$): δ 2.35–2.67(2H, m) 3.56–3.75(2H, m) 3.79–3.94 (1H, m) 4.04–4.20(1H, m) 5.09–5.24(2H, m) 6.09–6.25(1H, m) 7.21–7.46(5H, m) 7.59(1H, dd, J=4.5 and 8.0 Hz) 8.79–8.96(2H, m) 8.95(1H, s) 14.25(1H, brs).

Example 8

Synthesis of (S)-N-(2,6-dichlorophenyl)-1-(1-benzyloxycarbonylpyrrolidin-3-yl)-1,4-dihydro[1,8]naphthyridin-4-one-3-carboxamide The same reaction was carried out as in Example 4, except for using (S)-1-(1-benzyloxycarbonylpyrrolidin-3-yl)-1,4-dihydro[1,8]naphthyridin-4-one-3-carboxylic acid, instead of (±)-1-(1-methoxycarbonylpyrrodin-3-yl)-1,4-dihydro[1,8]naphthyridin-4-one-3-carboxylic acid to obtain 95 mg (66%) of the above-identified compound as a slightly yellow crystal.

IR(KBr)cm$^{-1}$: 1693, 1614, 1485, 1414, 1343. MS(FAB) 538[M+H]$^+$. $^1$H-NMR(CDCl$_3$): δ 2.43–2.58(2H, m) 3.60–3.73(2H, m) 3.81–3.92(1H, m) 4.08–4.20(1H, m) 5.09–5.22(2H, m) 6.06–6.19(1H, m) 7.14–7.21(1H, m) 7.26–7.45(7H, m) 7.52(1H, dd, J=4.5 and 8.0 Hz) 8.82(1H, dd, J=1.9 and 4.5 Hz) 8.89(1H, dd, J=1.9 and 8.0 Hz) 9.10(1H, brs) 11.58(1H, brs).

Example 9

Synthesis of (S)-N-(2,6-dichlorophenyl)-1-(1-methoxycarbonylpyrrolidin-3-yl)-1,4-dihydro[1,8]naphthyridin-4-one-3-carboxamide To a 6 ml methanol solution of 95 mg (0.177 mmol) of the compound obtained in Example 8, 50 mg of 10% palladium activated carbon was added and was stirred at room temperature for 8 hours under hydrogen atmosphere. Then, after the catalyst was removed by filtration, the mother liquor was concentrated to obtain 54 mg of (S)-N-(2,6-dichlorophenyl)-1-(3-pyrrolidyl)-1,4-dihydro[1,8]naphthyridin-4-one-3-carboxamide, as a colorless oily substance.

Then, to a 4 ml anhydrous methylene chloride solution of (S)-N-(2,6-dichlorophenyl)-1-(3-pyrrolidyl)-1,4-dihydro[1,8]naphthyridin-4-one-3-carboxamide, 28 μl (0.20 mmol) of triethylamine and 12.4 μl (0.16 mmol) of methyl chlorocarbonate were added at room temperature and stirred for 40 minutes. The reaction solution was concentrated under vacuum and the residue was purified by a silica gel chromatography (hexane/ethyl acetate=1/2) to obtain 55 mg (67%) of the above-identified compound as a colorless oily substance.

IR(KBr)cm$^{-1}$: 2953, 2880, 1699, 1683, 1615, 1485, 1452, 1391. MS(FAB) 461[M+H]$^+$. $^1$H-NMR(CDCl$_3$): δ 2.42–2.58(2H, m) 3.58–3.69(2H, m) 3.73(3H, s) 3.74–3.88 (1H, m) 4.06–4.15(1H, m) 6.08–6.18(1H, m) 7.19(1H, t, J=8.2 Hz) 7.40(2H, d, J=8.2 Hz) 7.53(1H, dd, J=4.5 and 8.0 Hz) 8.83(1H, dd, J=1.9 and 4.5 Hz) 8.89(1H, dd, J=1.9 and 7.9 Hz) 9.10(1H, brs) 11.57(1H, brs).

Example 10

Synthesis of (S)-N-(3,5-dichloropyridin-4-yl)-1-(1-benzyloxycarbonylpyrrolidin-3-yl)-1,4-dihydro[1,8]naphthyridin-4-one-3-carboxamide To a 4 ml toluene solution of 333 mg (0.846 mmol) of the compound obtained in Example 7, 185 μl (2.54 mmol) of thionyl chloride was added at room temperature and was heated under reflux for 1.5 hours. Then, after the solvent was distilled off under vacuum to obtain the acid chloride as a slightly yellow oily substance.

Then, to a 4 ml anhydrous tetrahydrofuran solution of 166 mg (1.02 mmol) of 4-amino-3,5-dichloropyridine, 102 mg (abt. 60% oil suspension, 2.54 mmol) of sodium hydride was added and stirred at room temperature for 20 minutes. Again, the reaction mixture was cooled to 0° C. and, to this solution, a 3 ml anhydrous tetrahydrofuran solution of the above-synthesized acid chloride was added and stirred at room temperature for 2 hours. Then, the reaction solution was diluted with methylene chloride (20 ml), washed with water (15 ml), followed by drying over anhydrous sodium sulfate and the solvent was distilled off under vacuum. The residue was purified by a silica gel chromatography (hexane/ethyl acetate=1/1.5) to obtain 330 mg (72%) of the above-identified compound as a colorless oily substance.

$^1$H-NMR(CDCl$_3$): δ 2.44–2.60(2H, m) 3.61–3.75(2H, m) 3.80–3.93(1H, m) 4.08–4.21(1H, m) 5.11–5.24(2H, m) 6.10–6.21(1H, m) 7.26–7.42(5H, m) 7.55(1H, dd, J=4.5 and 8.0 Hz) 8.56(2H, s) 8.83(1H, dd, J=1.9 and 4.5 Hz) 8.89(1H, dd, J=1.9 and 8.0 Hz) 9.08(1H, brs) 12.02(1H, brs).

Example 11

Synthesis of (S)-N-(3,5-dichloropyridin-4-yl)-1-(1-methoxycarbonylpyrrolidin-3-yl)-1,4-dihydro[1,8]naphthyridin-4-one-3-carboxamide To a 4 ml methanol solution of 60 mg (0.11 mmol) of the compound obtained in Example 10, 20 μl (0.12 mmol) of 6N-hydrochloric acid and 30 mg of 10% palladium activated carbon were added and stirred at room temperature for 21 hours under hydrogen atmosphere. Then, after the catalyst was removed by filtration, the mother liquor was concentrated to obtain 47 mg of (S)-N-(3,5-dichloropyridin-4-yl)-1-(3-pyrrolidyl)-1,4-dihydro[1,8]naphthyridin-4-one-3-carboxamide hydrochloride, as a colorless oily substance.

Then, to a 4 ml anhydrous methylene chloride solution of (S)-N-(3,5-dichloropyridin-4-yl)-1-(3-pyrrolidyl)-1,4-dihydro[1,8]naphthyridin-4-one- 3-carboxamide hydrochloride, 43.6 μl (0.31 mmol) of triethylamine and 9.7 μl (0.125 mmol) of methyl chlorocarbonate were added at room temperature and stirred for 40 minutes. The reaction solution was concentrated under vacuum and the residue was purified by a silica gel chromatography (hexane/ethyl acetate=1/3) to obtain 45 mg (88%) of the above-identified compound as a colorless oily substance.

IR(KBr)cm$^{-1}$: 2956, 1694, 1616, 1540, 1486, 1456. MS(FAB) 462[M+H]$^+$. $^1$H-NMR(CDCl$_3$): δ 2.42–2.63(2H, m) 3.60–3.89(3H, m) 3.74(3H, s) 4.07–4.19(1H, m) 6.10–6.21(1H, m) 7.56(1H, dd, J=4.5 and 8.0 Hz) 8.56(2H, s) 8.86(1H, dd, J=1.8 and 4.5 Hz) 8.89(1H, dd, J=1.8 and 8.0 Hz) 9.06(1H, s) 12.03(1H, brs).

Example 12

Synthesis of (R)-ethyl 3-(1-benzyloxycarbonylpyrrolidin-3-ylamino)-2-(2-chloronicotinoyl)acrylate The same reaction was carried out as in Example 1, except for using (R)-3-amino-1-benzyloxycarbonylpyrrolidine, instead of (±)-3-amino-1-methoxycarbonylpyrrolidine to obtain 1.73 g (82%) of the above-identified compound, as a slightly yellow oily substance.

IR(KBr)cm$^{-1}$: 2978, 1702, 1638, 1394, 1323. MS(FAB) 458[M+H]$^+$. $^1$H-NMR(CDCl$_3$): δ 0.79 and 0.92(total 3H, t, J=7.1 Hz) 2.02–2.18(1H, m) 2.29–2.40(1H, m) 3.40–3.71 (3H, m) 3.78–4.01(2H, m) 4.08–4.21(1H, m) 5.08–5.20(2H, m) 7.21–7.41(6H, m) 7.49–7.58(1H, m) 8.18–8.32(1H, m) 8.35–8.40(1H, m) 9.61–9.75(0.2H, m) 11.08–11.22(0.8H, m).

Example 13

Synthesis of (R)-ethyl 1-(1-benzyloxycarbonylpyrrolidin-3-yl)-1,4-dihydro[1,8] naphthyridin-4-one-3-carboxylate The same reaction was carried out as in Example 2, except for using (R)-ethyl 3-(1-benzyloxycarbonylpyrrolidin-3-ylamino)-2-(2-chloronicotinoyl)acrylate, instead of (±)-ethyl 3-(1-methoxycarbonylpyrrolidin-3-ylamino)-2-(2-chloronicotinoyl)acrylate, to obtain 1.42 g (92%) of the above-identified compound, as a slightly yellow crystal. MS(FAB) 422[M+H]$^+$. $^1$H-NMR(CDCl$_3$): δ 1.40(3H, t, J=7.1 Hz) 2.32–2.43(1H, m) 2.45–2.59(1H, m) 3.61–3.87 (3H, m) 4.04–4.13(1H, m) 4.39(2H, q, J=7.1 Hz) 5.14–5.22 (1H, m) 6.02–6.12 (1H, m) 5.27–5.45(6H, m) 8.67(1H, s) 8.72(1H, dd, J=2.0 and 4.5 Hz) 8.80(1H, dd, J=2.0 and 7.8 Hz).

Example 14

Synthesis of (R)-ethyl 1-(1-methoxycarbonylpyrrolidin-3-yl)-1,4-dihydro[1,8] naphthyridin-4-one-3-carboxylate The same reaction was carried out as in Example 11, except for using (R)-ethyl 1-(1-benzyloxycarbonylpyrrolidin-3-yl)-1,4-dihydro[1,8] naphthylidin-4-one-3-carboxylate, instead of (S)-N-(3,5-dichloropyridin-4-yl)-1-(1-benzyloxycarbonylpyrrolidin-3-yl)-1,4-dihydro[1,8]naphthylidin-4-one-3-carboxamide, to obtain 247 mg (67%) of the above-identified compound as a slightly yellow crystal.

IR(KBr)cm$^{-1}$: 2980, 2871, 1736, 1699, 1632, 1456, 1385, 1202. MS(FAB) 346[M+H]$^+$. $^1$H-NMR(CDCl$_3$): δ 1.41(3H, t, J=7.1 Hz) 2.25–2.57(2H, m) 3.53–3.79(3H, m) 3.76(3H, s) 3.92–4.13(1H, m) 4.40(2H, q, J=7.1 Hz) 5.96–6.12(1H, m) 7.43(1H, dd, J=4.5 and 7.8 Hz) 8.66(1H, s) 8.73(1H, dd, J=1.8 and 4.5 Hz) 8.80(1 H, dd, J=1.8 and 7.8 Hz).

Example 15

Synthesis of (R)-1-(1-methoxycarbonylpyrrolidin-3-yl)-1,4-dihydro[1,8]naphthyridin-4-one-3-carboxylic acid The same reaction was carried out as in Example 3, except for using (R)-ethyl 1-(1-methoxycarbonylpyrrolidin-3-yl)-1, 4-dihydro[1,8]naphtylidin-4-one-3-carboxylate, instead of (±)-ethyl 1-(1-methoxycarbonylpyrrolidin-3-yl)-1,4-dihydro[1,8]naphtylidin-4-one-3-carboxylate, to obtain 200 mg (97%) of the above-identified compound, as a slightly yellow crystal.

IR(KBr)cm$^{-1}$: 2959, 2883, 1698, 1615, 1456, 1381. MS(FAB) 318[M+H]$^+$. $^1$H-NMR(CDCl$_3$): δ 2.36–2.65(2H, m) 3.60–3.87(3H, m) 3.76(3H, s) 4.06–4.15(1H, m) 6.13–6.23(1H, m) 7.59(1H, dd, J=4.5 and 8.0 Hz) 8.85(1H, dd, J=2.0 and 8.0 Hz) 8.90(1H, dd, J=2.0 and 4.5 Hz) 8.95(1H, s) 14.27(1H, brs).

Example 16

Synthesis of (R)-N-(2,6-dichlorophenyl)-1-(1-methoxycarbonylpyrrolidin-3-yl)-1,4-dihydro[1,8] naphthyridin-4-one-3-carboxamide The same reaction was carried out as in Example 4, except for using (R)-1-(1-methoxycarbonylpyrrolidin-3-yl)-1,4-dihydro[1,8]naphthyridin-4-one-3-carboxylic acid instead of (±)-1-(1-methoxycarbonylpyrrolidin-3-yl)-1,4-dihydro[1,8]naphthyridin-4-one-3-carboxylic acid, to obtain 57 mg (42%) of the above-identified compound, as a slightly yellow oily substance.

IR(KBr)cm$^{-1}$: 3436, 2953, 1702, 1686, 1615, 1485, 1452. MS (FAB) 461[M+H]$^+$. $^1$H-NMR(CDCl$_3$): δ 2.42–2.58(2H, m) 3.58–3.69 (2H, m) 3.73(3H, s) 3.74–3.88(1H, m) 4.06–4.15(1H, m) 6.08–6.18(1H, m) 7.19(1H, t, J=8.2 Hz) 7.40(2H, d, J=8.2 Hz) 7.53(1H, dd, J=4.5 and 8.0 Hz) 8.83(1H, dd, J=1.9 and 4.5 Hz) 8.89(1H, dd, J=1.9 and 7.9 Hz) 9.10(1H, brs) 11.57(1H, brs).

Example 17

Synthesis of (R)-N-(3,5-dichloropyridin-4-yl)-1-(1-methoxycarbonylpyrrolidin-3-yl)-1,4-dihydro[1,8] naphthylidin-4-one-3-carboxamide The same reaction was carried out as in Example 10, except for using (R)-1-(1-methoxycarbonylpyrrolidin-3-yl)-1,4-dihydro[1,8]naphthyridin-4-one-3-carboxylic acid instead of (S)-1-(1-benzyloxycarbonylpyrrolidin-3-yl)-1,4-dihydro[1,8]naphthylidin-4-one-3-carboxylic acid, to obtain 120 mg (89%) of the above-identified compound as a slightly yellow oily substance.

IR(neat)cm$^{-1}$: 2952. 1694, 1614, 1540, 1484. MS(FAB) 462[M+H]$^+$. $^1$H-NMR(CDCl$_3$): δ 2.42–2.63(2H, m)

3.60–3.89(3H, m) 3.74 (3H, s) 4.07–4.19(1H, m) 6.10–6.21 (1H, m) 7.56(1H, dd, J=4.5 and 8.0 Hz) 8.56(2H, s) 8.86(1H, dd, J=1.8 and 4.5 Hz) 8.89(1 H, dd, J=1.8 and 8.0 Hz) 9.06(1H, s) 12.03(1H, brs).

Example 18

Synthesis of (S)-N-(3,5-dichloropyridin-4-yl)-1-(1-ethylaminocarbonylpyrrolidin-3-yl)-1,4-dihydro[1,8]naphthylidin-4-one-3-carboxamide To a 30 ml methanol solution of 562 mg (1.04 mmol) of the compound obtained in Example 10, 191 µl (1.15 mmol) of 6N-hydrochloric acid and 140 mg of 10% palladium activated carbon were added and stirred at room temperature for 24 hours under hydrogen atmosphere. Then, after the catalyst was removed by filtration, the mother liquor was concentrated to obtain 444 mg of (S)-N-(3,5-dichloropyridin-4-yl)-1-(3-pyrrolidyl)-1,4-dihydro[1,8]naphthylidin-4-one-3-carboxamide hydrochloride as a colorless oily substance.

Then, to a 3 ml anhydrous methylene chloride solution of 85 mg of (S)-N-(3,5-dichloropyridin-4-yl)-1-(3-pyrrolidyl)-1,4-dihydro[1,8]naphthylidin-4-one-3-carboxamide hydrochloride, 81 µl (0.58 mmol) of triethylamine and 30.5 µl (0.386 mmol) of ethyl isocyanate were added and stirred for 1 hour. The reaction solution was diluted with water (10 ml) and extracted with methylene chloride (30 ml), followed by drying over anhydrous sodium sulfate and concentrating under vacuum. The residue was purified by a silica gel chromatography (methylene chloride/methanol=20/1) to obtain 76 mg (80%) of the above-identified compound as a colorless crystal.

IR(KBr)cm$^{-1}$: 3324, 2976, 1693, 1615, 1542, 1485, 1414. MS (FAB) 475[M+H]$^+$. $^1$H-NMR(CDCl$_3$): δ 1.16(3H, t, J=7.2 Hz) 2.48–2.68(2H, m) 3.26–3.35(2H, m) 3.58–3.70 (2H, m) 3.73–3.80(1H, m) 4.06–4.13(1H, m) 4.23–4.30(1H, m) 6.15–6.23(1H, m) 7.55(1H, dd, J=4.5 and 8.0 Hz) 8.56(2H, s) 8.85(1H, dd, J=2.0 and 4.5 Hz) 8.89(1H, dd, 2.0 and 8.0 Hz) 9.06(1H, s) 12.03(1H, brs).

Example 19

Synthesis of (S)-N-(3,5-dichloropyridin-4-yl)-1-(1-methylaminothiocarbonylpyrrolidin-3-yl)-1,4-dihydro[1,8]naphthylidin-4-one-3-carboxamide The same reaction was carried out as in Example 18, except for using methyl isothiocyanate, instead of ethyl isocyanate, to obtain 70 mg (83%) of the above-identified compound, as a colorless crystal.

IR(KBr)cm$^{-1}$: 3320, 2870, 1694, 1614, 1539, 1487. MS(FAB) 177[M+H]$^+$. $^1$H-NMR(CDCl$_3$): δ 2.65–2.75(2H, m) 3.15–3.18(3H, m) 3.72–3.82(1H, m) 3.92–4.06(2H, m) 4.43–4.51(1H, m) 5.39–5.46(1H, m) 6.13–6.22(1H, m) 7.56 (1H, dd, J=4.5 and 7.8 Hz) 8.56(2H, s) 8.85(1H, dd, J=1.9 and 4.5 Hz) 8.89(1H, dd, 1.9 and 7.8 Hz) 9.04(1H, s) 11.99(1H, brs).

Example 20

Synthesis of (S)-N-(3,5-dichloropyridin-4-yl)-1-(1-aminocarbonylpyrrolidin-3-yl)-1,4-dihydro[1,8]naphthylidin-4-one-3-carboxamide To a 30 ml methanol solution of 562 mg (1.04 mmol) of the compound obtained in Example 10, 191 µl (1.15 mmol) of 6N-hydrochloric acid, and 140 mg of 10% palladium activated carbon were added, and stirred at room temperature for 24 hours under hydrogen atmosphere. Then, after the catalyst was removed by filtration, the mother liquor was concentrated to obtain 444 mg of colorless oily (S)-N-(3,5-dichloropyridin-4-yl)-1-(3-pyrrolidyl)-1,4-dihydro[1,8]naphthylidin-4-one-3-carboxamide hydrochloride.

Then, to a 3 ml anhydrous methylene chloride solution of 60 mg of (S)-N-(3,5-dichloropyridin-4-yl)-1-(3-pyrrolidyl)-1,4-dihydro[1,8]naphthylidin-4-one-3-carboxamide hydrochloride, 57 µl (0.41 mmol) of triethylamine and 37 µl (0.27 mmol) of trimethylsilyl isocyanate were added and stirred for 1 hour and then 0.5 ml of a saturated hydrochloric acid methanol solution was added and stirred for 15 minutes. Then, the reaction solution was diluted with a saturated sodium hydrogen carbonate solution (10 ml), followed by extracting with methylene chloride (20 ml). The extract was dried over anhydrous sodium sulfate and then concentrated under vacuum. The residue was purified by a silica gel chromatography (methylene chloride/methanol=15/1) to obtain 52 mg (82%) of the above-identified compound as a colorless crystal.

IR(KBr)cm$^{-1}$: 3358, 1681, 1604, 1541, 1486. MS(FAB) 447[M+H]$^+$. $^1$H-NMR(CDCl$_3$): δ 2.52–2.71 (2H, m) 3.61–3.74(2H, m) 3.77–3.85(1H, m) 4.10–4.18(1H, m) 4.45 (2H, brs) 6.13–6.22(1H, m) 7.56(1H, dd, J=4.5 and 8.0 Hz) 8.56(2H, s) 8.86(1H, dd, J=2.0 and 4.5 Hz) 8.90(1H, dd, 2.0 and 8.0Hz) 9.07(1H, s) 12.02(1 H, brs).

Example 21

Synthesis of ethyl 3-(1-benzylpiperidin-4-ylamino)-2-(2-chloronicotinoyl)acrylate The same reaction was carried out as in Example 1, except for using 4-amino-1-benzylpiperidine, instead of (±)-3-amino-1-methoxycarbonylpyrrolidine to obtain 1.25 g (94%) of the above-identified compound, as a slightly yellow oily substance.

$^1$H-NMR(CDCl$_3$): δ 0.78 and 0.91(total 3H, t, J=7.1 Hz) 1.69–1.88(2H, m) 1.92–2.06(2H, m) 2.12–2.25(2H, m) 2.80–2.95(2H, m) 3.32–3.45(1H, m) 3.50–3.56(2H, m) 3.86–4.01(2H, m) 7.20–7.36(6H, m) 7.48–7.58(1H, m) 8.17–8.25(1H, m) 8.29–8.41(1H, m) 9.61–9.72(0.2H, m) 11.08–11.22(0.81H, m).

Example 22

Synthesis of ethyl 1-(1-benzylpiperidin-4-yl)-1,4-dihydro[1,8]naphthylidin-4-one-3-carboxylate The same reaction was carried out as in Example 2, except for using ethyl 3-(1-benzylpiperidin-4-ylamino)-2-(2-chloronicotinoyl)acrylate, instead of (±)-ethyl 3-(1-methoxycarbonylpyrrolidin-3-ylamino)-2-(2-chloronicotinoyl)acrylate, to obtain 0.95 g (85%) of the above-identified compound, as a slightly yellow crystal.

IR(KBr)cm$^{-1}$: 2976, 2938, 2800, 2759, 1690, 1651, 1416, 1231. MS(FAB) 392[M+H]$^+$. $^1$H-NMR(CDCl$_3$): δ 1.42(3H, t, J=7.1 Hz) 1.96–2.16(4H, m) 2.26–2.36(2H, m) 3.05–3.15 (2H, m) 3.61(2H, s) 4.41(2H, q, J=7.1 Hz) 5.49–5.59(1H, m) 7.25–7.32(1H, m) 7.35–7.38(4H, m) 7.39(1H, dd, J=4.5 and 8.0 Hz) 8.71(1H, dd, J=2.0 and 4.5 Hz) 8.78(1H, s) 8.80(1H, dd, J=2.0 and 8.0 Hz).

Example 23

Synthesis of ethyl 1-(1-benzyloxycarbonylpiperidin-4-yl)-1,4-dihydro[1,8]naphthylidin-4-one-3-carboxylate To a 8 ml 1,2-dichloroethane solution of 590 mg (1.51 mmol) of the compound obtained in Example 22, 226 µl (1.58 mmol) of benzyl chloroformate was added and stirred at 60° C. for 1 hour and further 226 μl (1.58 mmol) of benzyl chloroformate was added and stirred at 60° C. for 1 hour. After cooling, the solvent was distilled off under vacuum and the residue was purified by a silica gel chromatography (hexane/ethyl acetate=1/4) to obtain 560 mg (85%) of the above-identified compound, as a colorless crystal.

$^1$H-NMR(CDCl$_3$): δ 1.42(3H, t, J=7.1 Hz) 1.89–2.10(4H, m) 2.97–3.13(2H, m) 4.37–4.55(2H, m) 4.41 (2H, q, J=7.1 Hz) 5.14–5.21 (2H, m) 5.63–5.75(1H, m) 7.30–7.44(6H, m) 8.65(1H, s) 8.72(1 H, dd, J=1.9 and 4.5 Hz) 8.81(1H, dd, J=1.9 and 7.9 Hz).

Example 24

Synthesis of 1-(1-benzyloxycarbonylpiperidin-4-yl)-1,4-dihydro[1,8]naphthylidin-4-one-3-carboxylic acid The same reaction was carried out as in Example 3, except for using ethyl 1-(1-benzyloxycarbonylpiperidin-4-yl)-1,4-dihydro[1,8]naphtylidin-4-one-3-carboxylate, instead of (±)-ethyl 1-(1-methoxycarbonylpyrrolidin-3-yl)-1,4-dihydro[1,8]naphtylidin-4-one-3-carboxylate, to obtain 447 mg (92%) of the above-identified compound, as a slightly yellow crystal.

IR(KBr)cm$^{-1}$: 2923, 2807, 2765, 1680, 1621, 1567, 1390. MS (FAB) 428[M+H]$^+$. $^1$H-NMR(CDCl$_3$): δ 1.94–2.10(4H, m) 2.98–3.12 (2H, m) 4.42–4.56(2H, m) 5.20(2H, s) 5.76–5.89(1H, m) 7.31–7.41(5H, m) 7.58(1H, dd, J=4.4 and 8.0 Hz) 8.86(1H, dd, J=2.0 and 8.0 Hz) 8.89(1H, dd, J=2.0 and 4.4 Hz) 8.95(1H, s) 14.36(1H, s).

Example 25

Synthesis of N-(3,5-dichloropyridin-4-yl)-1-(1-benzyloxycarbonylpiperidin-4-yl)-1,4-dihydro[1,8]naphthylidin-4-one-3-carboxamide The same reaction was carried out as in Example 10, except for using 1-(1-benzyloxycarbonylpiperidin-4-yl)-1,4-dihydro[1,8]naphtylidin-4-one-3-carboxylic acid, instead of (S)-1-(1-benzyloxycarbonylpyrrolidin-3-yl)-1,4-dihydro[1,8]naphthylidin-4-one-3-carboxylic acid, to obtain 316 mg (60%) of the above-identified compound, as a colorless crystal.

IR(KBr)cm$^{-1}$: 3454, 2964, 1691, 1619, 1490, 1222. MS(FAB) 552[M+H]$^+$. $^1$H-NMR(CDCl$_3$): δ 2.04–2.14(4H, m) 3.01–3.13(2H, m) 4.42–4.56(2H, m) 5.19(2H, brs) 5.75–5.88(1H, m) 7.27–7.45(5H, m) 7.54(1H, dd, J=4.5 and 7.9 Hz) 8.56(2H, s) 8.84(1H, dd, J=2.0 and 4.5 Hz) 8.90(1H, dd, J=2.0 and 7.9 Hz) 9.05(1H, s) 12.11(1H, brs).

Example 26

Synthesis of N-(3,5-dichloropyridin-4-yl)-1-(1-methoxycarbonylpiperidin-4-yl)-1,4-dihydro[1,8]naphthylidin-4-one-3-carboxamide The same reaction was carried out as in Example 11, except for using N-(3,5-dichloropyridin-4-yl)-1-(1-benzyloxycarbonylpiperidin-4-yl)-1,4-dihydro[1,8]naphthylidin-4-one-3-carboxamide, instead of (S)-N-(3,5-dichloropyridin-4-yl)-1-(1-benzyloxycarbonylpyrrolidin-3-yl)-1,4-dihydro[1,8]naphthylidin-4-one-3-carboxamide, to obtain 35 mg (52%) of the above-identified compound, as a yellow crystal.

IR(KBr)cm$^{-1}$: 2948, 1694, 1680, 1613, 1492, 1413, 1235. MS (FAB) 476[M+H]$^+$. $^1$H-NMR(CDCl$_3$): δ 2.01–2.13(4H, m) 2.99–3.13 (2H, m) 3.77(3H, s) 4.35–4.54(2H, m) 5.75–5.88(1H, m) 7.54(1 H, dd, J=4.5 and 8.0 Hz) 8.56(2H, s) 8.85(1H, dd, J=2.0 and 4.5 Hz) 8.90(1H, dd, J=2.0 and 8.0 Hz) 9.05(1H, s) 12.11(1H, brs).

Example 27

Synthesis of N-(3,5-dichloropyridin-4-yl)-1-(1-ethylaminocarbonylpiperidin-4-yl)-1,4-dihydro[1,8]naphthylidin-4-one-3-carboxamide The same reaction was carried out as in Example 18, except for using N-(3,5-dichloropyridin-4-yl)-1-(1-benzyloxycarbonylpiperidin-4-yl)-1,4-dihydro[1,8]naphthylidin-4-one-3-carboxamide, instead of (S)-N-(3,5-dichloropyridin-4-yl)-1-(1-benzyloxycarbonylpyrrolidin-3-yl)-1,4-dihydro[1,8]naphthylidin-4-one-3-carboxamide, to obtain 32 mg (47%) of the above-identified compound, as a colorless oily substance.

IR(KBr)cm$^{-1}$: 3395, 2952, 1680, 1616, 1540, 1488, 1238. MS (FAB) 489[M+H]$^+$. $^1$H-NMR(CDCl$_3$): δ 1.19(3H, t, J=7.2 Hz) 2.04–2.14(4H, m) 3.01–3.12(2H, m) 3.27–3.36 (2H, s) 4.19–4.28(2H, m) 4.44–4.51(1H, m) 5.74–5.85(1H, m) 7.54(1H, dd, J=4.5 and 8.0 Hz) 8.56(2H, s) 8.85(1H, dd, J=2.0 and 4.5 Hz) 8.90(1H, dd, J=2.0 and 8.0 Hz) 9.06(1H, s) 12.11(1H, brs).

Example 28

Synthesis of N-(3,5-dichloropyridin-4-yl)-1-(1-acetylpiperidin-4-yl)-1,4-dihydro[1,8]naphthylidin-4-one-3-carboxamide The same reaction was carried out as in Example 26, except for using acetic anhydride instead of methyl chlorocarbonate, to obtain 50 mg (40%) of the above-identified compound, as a slightly yellow oily substance.

IR(KBr)cm$^{-1}$: 3454, 2934, 1694, 1683, 1636, 1615, 1540, 1486. MS(FAB) 460[M+H]$^+$. $^1$H-NMR(CDCl$_3$): δ 1.95–2.23(7H, m) 2.75–2.86(1H, m) 3.31–3.42(1H, m) 4.02–4.15(1H, m) 4.92–5.01(1H, m) 5.80–5.91(1H, m) 7.55 (1H, dd, J=4.5 and 8.0 Hz) 8.56(2H, s) 8.85(1H, dd, J=1.9 and 4.5 Hz) 8.90(1H, dd, J=1.9 and 8.0 Hz) 9.04(1H, s) 12.09(1H, brs).

Example 29

Synthesis of ethyl 3-(1-methoxycarbonylazetidin-3-ylamino)-2-(2-chloronicotinoyl)acrylate The same reaction was carried out as in Example 1, except for using 3-amino-1-methoxycarbonylazetidine, instead of (±)-3-amino-1-methoxycarbonylpyrrolidine to obtain 1.34 g (74%) of the above-identified compound, as a slightly yellow oily substance.

IR(KBr)cm$^{-1}$: 2982, 1694, 1682, 1634, 1574, 1558, 1393. MS (FAB) 368[M+H]$^+$. $^1$H-NMR(CDCl$_3$): δ 0.80 and 0.93 (total 3H, t, J=7.1 Hz) 3.69–3.74(3H, m) 3.91–4.15(3H, m) 4.36–4.49(2H, m) 7.23–7.31(1H, m) 7.53 and 7.58(total 1H, dd, J=1.9 and 7.5 Hz) 8.15(0.8H, d, J=13.6 Hz) 8.19(0.2H, d, J=13.9 Hz) 8.37–8.42(1H, m) 9.85–9.96(0.2H, m) 11.26–11.37(0.8H, m).

Example 30

Synthesis of ethyl 1-(1-methoxycarbonylazetidin-3-yl)-1,4-dihydro[1,8]naphthylidin-4-one-3-carboxylate The same reaction was carried out as in Example 2, except for using ethyl 3-(1-methoxycarbonylazetidin-3-ylamino-2-

(2-chloronicotinoyl)acrylate, instead of (±)-ethyl 3-(1-methoxycarbonylpyrrolidin-3-ylamino)-2-(2-chloronicotinoyl)acrylate, to obtain 0.93 g (79%) of the above-identified compound, as a slightly yellow crystal.

IR(KBr)cm$^{-1}$: 2967, 1690, 1638, 1466, 1365, 1233. MS(FAB) 332[M+H]$^+$. $^1$H-NMR(CDCl$_3$): δ 1.43(3H, t, J=7.1 Hz) 3.75(3H, s) 4.37(2H, dd, J=5.7 and 9.8 Hz) 4.43(2H, q, J=7.1 Hz) 4.60(2H, dd, 8.3 and 9.8 Hz) 5.90–5.99(1H, m) 7.43(1H, dd, J=4.6 and 8.0 Hz) 8.70(1H, dd, J=2.0 and 4.6 Hz) 8.79(1H, dd, J=2.0 and 8.0 Hz) 8.82(1H, s).

Example 31

Synthesis of 1-(1-methoxycarbonylazetidin-3-yl)-1,4-dihydro[1,8]naphthylidin-4-one-3-carboxylic acid The same reaction was carried out as in Example 3, except for using ethyl 1-(1-methoxycarbonylazetidin-3-yl)-1,4-dihydro[1,8]naphthylidin-4-one-3-carboxylate, instead of (±)-ethyl 1-(1-methoxycarbonylpyrrolidin-3-yl)-1,4-dihydro[1,8]naphthylidin-4-one-3-carboxylate, to obtain 453 mg (87%) of the above-identified compound, as a slightly yellow crystal.

IR(KBr)cm$^{-1}$: 3088, 2963, 1716, 1823, 1460, 1392. MS(FAB) 304[M+H]$^+$. $^1$H-NMR(CDCl$_3$): δ 3.76(3H, s) 4.39(2H, dd, J=5.6 and 10.0 Hz) 4.64(2H, dd, 8.1 and 10.0 Hz) 6.01–6.10(1H, m) 7.59(1H, dd, J=4.6 and 7.7 Hz) 8.83–8.89(2H, m) 8.86(1H, s) 14.20(1H, brs).

Example 32

Synthesis of N-(3-pyridyl)-1-(1-methoxycarbonylazetidin-3-yl)-1,4-dihydro[1,8]naphthylidin-4-one-3-carboxamide The same reaction was carried out as in Example 4, except for using 1-(1-methoxycarbonylazetidin-3-yl)-1,4-dihydro[1,8]naphtyridin-4-one-3-carboxylic acid, instead of (±)-1-(1-methoxycarbonylpyrrolidin-3-yl)-1,4-dihydro[1,8]naphtylidin-4-one-3-carboxylic acid, and using 3-aminopyridine, instead of 2,6-dichloroaniline, to obtain 59 mg (57%) of the above-identified compound, as a colorless oily substance.

IR(KBr)cm$^{-1}$: 2960, 1720, 1686, 1678, 1606, 1546, 1492. MS (FAB) 380[M+H]$^+$. $^1$H-NMR(CDCl$_3$): δ 3.76(3H, s) 4.40–4.49(2H, m) 4.61–4.69(2H, m) 6.03–6.12(1H, m) 7.31 (1H, dd, J=4.6 and 8.2 Hz) 7.54(1H, dd, J=4.5 and 7.9 Hz) 8.27–8.41(2H, m) 8.80–8.94(3H, m) 9.24(1H, s) 12.05(1H, brs).

Example 33

Synthesis of N-(4-pyridyl)-1-(1-methoxycarbonylazetidin-3-yl)-1,4-dihydro[1,8]naphthylidin-4-one-3-carboxamide The same reaction was carried out as in Example 4, except for using 1-(1-methoxycarbonylazetidin-3-yl)-1,4-dihydro[1,8]naphtyridin-4-one-3-carboxylic acid, instead of (±)-1-(1-methoxycarbonylpyrrolidin-3-yl)-1,4-dihydro[1,8]naphtylidin-4-one-3-carboxylic acid, and using 4-aminopyridine, instead of 2,6-dichloroaniline, to obtain 98 mg (52%) of the above-identified compound, as a colorless crystal.

IR(KBr)cm$^{-1}$: 2951, 1690, 1607, 1569, 1537, 1504, 1422, 1368, 1195. MS(FAB) 380[M+H]$^+$. $^1$H-NMR(CDCl$_3$): δ 3.76(3H, s) 4.42(2H, dd, J=5.6 and 10.0 Hz) 4.61–4.69(2H, m) 6.03–6.12(1H, m) 7.56(1H, dd, J=4.5 and 7.9 Hz) 7.69(2H, dd, J=1.5 and 4.9 Hz) 8.54(2H, dd, J=1.5 and 4.9 Hz) 8.81–8.88(2H, m) 9.23(1H, s) 12.16(1H, brs).

Example 34

Synthesis of N-(3,5-dichloropyridin-4-yl)-1-(1-methoxycarbonylazetidin-3-yl)-1,4-dihydro[1,8]naphthylidin-4-one-3-carboxamide The same reaction was carried out as in Example 10, except for using 1-(1-methoxycarbonylazetidin-3-yl)-1,4-dihydro[1,8]naphtyridin-4-one-3-carboxylic acid, instead of (S)-1-(1-benzyloxycarbonylpyrrolidin-3-yl)-1,4-dihydro[1,8]naphtyridin-4-one-3-carboxylic acid, to obtain 60 mg (20%) of the above-identified compound, as a slightly brown oily substance.

IR(KBr)cm$^{-1}$. 2954, 1686, 1617, 1485, 1400. MS(FAB) 448[M+H]$^+$. $^1$H-NMR(CDCl$_3$): δ 3.75(3H, s) 4.44(2H, dd, J=5.7 and 9.9 Hz) 4.60–4.67(2H, m) 5.96–6.08(1H, m) 7.56(1H, dd, J=4.5 and 8.0 Hz) 8.57(2H, s) 8.82(1H, dd, J=1.9 and 4.5 Hz) 8.88(1H, d d, J=1.9 and 8.0 Hz) 9.21(1H, s) 11.99(1H, brs).

Example 35

Synthesis of ethyl 3-[(R)-tetrahydro-3-furanylamino)]-2-(2-chloronicotinoyl)acrylate The same reaction was carried out as in Example 1, except for using (R)-3-aminotetrahydrofuran, instead of (±)-3-amino-1-methoxycarbonylpyrrolidine to obtain 960 mg (84%) of the above-identified compound, as a colorless crystal.

IR(KBr)cm$^{-1}$: 2983, 1682, 1629, 1547, 1389, 1318, 1258. MS (FAB) 325[M+H]$^+$. $^1$H-NMR(CDCl$_3$): δ 0.74 and 0.92 (total 3H, t, J=7.1 Hz) 2.05–2.15(1H, m) 2.38–2.49(1H, m) 3.84–4.10(6H, m) 4.15–4.25(1H,m) 7.24–7.30(1H, m) 7.50–7.60(1H, m) 8.21 and 8.29(total 1H, d, J=14.0 Hz) 8.36–8.45(1H, m) 9.71(0.04H, br) 11.17(0.96H, br).

Example 36

Synthesis of ethyl 1-[(R)-tetrahydro-3-furanyl]-1,4-dihydro[1,8]naphthylidin-4-one-3-carboxylate The same reaction was carried out as in Example 2, except for using ethyl 3-[(R)-tetrahydro-3-furanylamino]-2-(2-chloronicotinoyl)acrylate, instead of (±)-ethyl 3-(1-methoxycarbonylpyrrolidin-3-ylamino)-2-(2-chloronicotinoyl)acrylate, to obtain 730 mg (89%) of the above-identified compound, as a colorless crystal.

IR(KBr)cm$^{-1}$: 2928, 2852, 1726, 1698, 1637, 1583, 1490, 1338, 1225. MS(FAB) 289[M+H]$^+$. $^1$H-NMR(CDCl$_3$): δ 1.42(3H, t, J=7.1 Hz) 2.03–2.23(1H, m) 2.62–2.73(1H, m) 3.92–4.00(1H, m) 4.03–4.08(1H, m) 4.12–4.18(1H, m) 4.25–4.33(1H, m) 4.41(2H, q, J=7.1 Hz) 6.24–6.30(1H, m) 7.41(1H, dd, J=4.5 and 7.9 Hz) 8.72(1H, dd, J=1.9 and 4.5 Hz) 8.80(1H, dd, J=1.9 and 7.9 Hz) 8.82(1H, s).

Example 37

Synthesis of 1-[(R)-tetrahydro-3-furanyl]-1,4-dihydro[1,8]naphthylidin-4-one-3-carboxylic acid The same reaction was carried out as in Example 3, except for using ethyl 1-[(R)-tetrahydro-3-furanyl]-1,4-dihydro[1,8]naphtyridin-4-one-3-carboxylate, instead of (±)-ethyl 1-(1-methoxycarbonylpyrrolidin-3-yl)-1,4-dihydro[1,8]

naphtylidin-4-one-3-carboxylate, to obtain 440 mg (92%) of the above-identified compound, as a colorless crystal.

IR(KBr)cm$^{-1}$: 3436, 1728, 1613, 1468, 1408, 796. MS(FAB) 261[M+H]$^+$. $^1$H-NMR(CDCl$_3$): δ 2.17–2.27(1H, m) 2.66–2.77(1H, m) 3.92–4.00(1H, m) 4.05–4.15(2H, m) 4.28–4.36(1H, m) 6.33–6.41(1H, m) 7.58(1H, dd, J=4.5 and 7.9 Hz) 8.82–8.91(2H, m) 9.09(1H, s) 14.36(1H, m).

Example 38

Synthesis of N-(4-pyridyl)-1-[(R)-tetrahydro-3-furanyl]-1,4-dihydro[1,8]naphthylidin-4-one-3-carboxamide The same reaction was carried out as in Example 4, except for using 1-[(R)-tetrahydro-3-furanyl]-1,4-dihydro[1,8]naphtyridin-4-one-3-carboxylic acid, instead of (±)-1-(1-methoxycarbonylpyrrolidin-3-yl)-1,4-dihydro[1,8]naphtylidin-4-one-3-carboxylic acid, and using 4-aminopyridine, instead of 2,6-dichloroaniline to obtain 148 mg (76%) of the above-identified compound, as a yellow crystal.

IR(KBr)cm$^{-1}$: 2981, 1682, 1573, 1534, 1486, 1406. MS(FAB) 337[M+H]$^+$. $^1$H-NMR(CDCl$_3$): δ 2.19–2.30(1H, m) 2.65–2.76(1H, m) 3.95–4.04(1H, m) 4.07–4.18(2H, m) 4.31–4.41(1H, m) 6.33–6.40 (1H, m) 7.54(1H, dd, J=4.7 and 7.8 Hz) 7.68(2H, dd, J=1.5 and 4.8 Hz) 8.52(2H, dd, J=1.5 and 4.8 Hz) 8.83–8.90(2H, m) 9.21(1H, s) 12.24(1H, brs).

Example 39

Synthesis of N-(3,5-dichloropyridin-4-yl)-1-[(R)-tetrahydro-3-furanyl]-1,4-dihydro[1,8]naphthylidin-4-one-3-carboxamide The same reaction was carried out as in Example 10, except for using 1-[(R)-tetrahydro-3-furanyl]-1,4-dihydro[1,8]naphtyridin-4-one-3-carboxylic acid, instead of (S)-1-(1-benzyloxycarbonylpyrrolidin-3-yl)-1,4-dihydro[1,8]naphtyridin-4-one-3-carboxylic acid, to obtain 176 mg (75%) of the above-identified compound, as a slightly yellow oily substance.

IR(KBr)cm$^{-1}$: 2888, 1690, 1621, 1538, 1485. MS(FAB) 405[M+H]$^+$. $^1$H-NMR(CDCl$_3$): δ 2.23–2.33(1H, m) 2.64–2.78(1H, m) 3.93–4.01(1H, m) 4.08–4.16(2H, m) 4.30–4.38(1H, m) 6.32–6.38(1H, m) 7.54(1H, dd, J=4.5 and 8.0 Hz) 8.56(2H, s) 8.85(1H, dd, J=1.9 and 4.5 Hz) 8.89(1H, dd, J=1.9 and 8.0 Hz) 9.18(1H, s) 12.07(1H, brs).

Example 40

Synthesis of ethyl 3-[(S)-tetrahydro-3-furanylamino]-2-(2-chloronicotinoyl)acrylate The same reaction was carried out as in Example 1, except for using (S)-3-aminotetrahydrofuran, instead of (±)-3-amino-1-methoxycarbonylpyrrolidine to obtain 885 mg (75%) of the above-identified compound, as a colorless crystal.

IR(KBr)cm$^{-1}$: 3206, 2983, 2884, 1682, 1629, 1548, 1389, 1318. MS(FAB) 325[M+H]$^+$. $^1$H-NMR(CDCl$_3$): δ 0.74 and 0.92(total 3H, t, J=7.1 Hz) 2.05–2.15(1H, m) 2.38–2.49(1H, m) 3.84–4.10 (6H, m) 4.15–4.25(1H,m) 7.24–7.30(1H, m) 7.50–7.60(1H, m) 8.21 and 8.29(total 1H, d, J=14.0 Hz) 8.36–8.45(1H, m) 9.71(0.04H, br) 11.17(0.96H, br).

Example 41

Synthesis of ethyl 1-[(S)-tetrahydro-3-furanyl]-1,4-dihydro[1,8]naphthylidin-4-one-3-carboxylate The same reaction was carried out as in Example 2, except for using ethyl 3-[(S)-tetrahydro-3-furanylamino]-2-(2-chloronicotinoyl)acrylate, instead of (±)-ethyl 3-(1-methoxycarbonylpyrrolidin-3-ylamino-2-(2-chloronicotinoyl)acrylate, to obtain 639 mg (87%) of the above-identified compound, as a colorless crystal.

IR(KBr)cm$^{-1}$: 2982, 2846, 1727, 1698, 1637, 1583, 1490, 1422. MS(FAB) 289[M+H]$^+$. $^1$H-NMR(CDCl$_3$): δ 1.42(3H, t, J=7.1 Hz) 2.03–2.23(1H, m) 2.62–2.73(1H, m) 3.92–4.00 (1H, m) 4.03–4.08(1H, m) 4.12–4.18(1H, m) 4.25–4.33(1H, m) 4.41(2H, q, J=7.1 Hz) 6.24–6.30(1H, m) 7.41 (1H, dd, J=4.5 and 7.9 Hz) 8.72(1H, dd, J=1.9 and 4.5 Hz) 8.80(1H, dd, J=1.9 and 7.9 Hz) 8.82(1H, s).

Example 42

Synthesis of 1-[(S)-tetrahydro-3-furanyl]-1,4-dihydro[1,8]naphthylidin-4-one-3-carboxylic acid The same reaction was carried out as in Example 3, except for using ethyl 1-[(S)-tetrahydro-3-furanyl]-1,4-dihydro[1,8]naphthyridin-4-one-3-carboxylate, instead of (±)-ethyl 1-(1-methoxycarbonylpyrrolidin-3-yl)-1,4-dihydro[1,8]naphtyridin-4-one-3-carboxylate, to obtain 474 mg (98%) of the above-identified compound, as a colorless crystal.

IR(KBr)cm 3068, 2886, 1732, 1613, 1468, 795. MS(FAB) 261[M+H]$^+$. $^1$H-NMR(CDCl$_3$): δ 2.17–2.27(1H, m) 2.66–2.77(1H, m) 3.92–4.00(1H, m) 4.05–4.15(2H, m) 4.28–4.36(1H, m) 6.33–6.41(1H, m) 7.58(1H, dd, J=4.5 and 7.9 Hz) 8.82–8.91(2H, m) 9.09(1H, s) 14.36(1H, m).

Example 43

Synthesis of N-(4-pyridyl)-1-[(S)-tetrahydro-3-furanyl]-1,4-dihydro[1,8]naphthylidin-4-one-3-carboxamide The same reaction was carried out as in Example 4, except for using 1-[(S)-tetrahydro-3-furanyl]-1,4-dihydro[1,8]naphtylidin-4-one-3-carboxylic acid, instead of (±)-1-(1-methoxycarbonylpyrrolidin-3-yl)-1,4-dihydro[1,8]naphtyridin-4-one-3-carboxylic acid, and using 4-aminopyridine, instead of 2,6-dichloroaniline, to obtain 134 mg (75%) of the above-identified compound, as a slightly yellow crystal.

$^1$H-NMR(CDCl$_3$): δ 2.19–2.30(1H, m) 2.65–2.76(1H, m) 3.95–4.04(1H, m) 4.07–4.18(2H, m) 4.31–4.41(1H, m) 6.33–6.40(1H, m) 7.54(1H, dd, J=4.7 and 7.8 Hz) 7.68(2H, dd, J=1.5 and 4.8 Hz) 8.52(2H, dd, J=1.5 and 4.8 Hz) 8.83–8.90(2H, m) 9.21(1H, s) 12.24(1H, brs).

Example 44

Synthesis of N-(3,5-dichloropyridine-4-yl)-1-[(S)-tetrahydro-3-furanyl]-1,4-dihydro[1,8]naphthylidin-4-one-3-carboxamide The same reaction was carried out as in Example 10, except for using 1-[(S)-tetrahydro-3-furanyl]-1,4-dihydro[1,8]naphtyridin-4-one-3-carboxylic acid, instead of (S)-1-(1-benzyloxycarbonylpyrrolidin-3-yl)-1,4-dihydro[1,8]naphtyridin-4-one-3-carboxylic acid, to obtain 175 mg (75%) of the above-identified compound, as a slightly yellow crystal.

IR(KBr)cm$^{-1}$: 2887, 1689, 1621, 1538, 1483, 1411. MS(FAB) 461[M+H]$^+$. $^1$H-NMR(CDCl$_3$): δ 2.23–2.33(1H, m) 2.64–2.78(1H, m) 3.93–4.01(1H, m) 4.08–4.16(2H, m) 4.30–4.38(1H, m) 6.32–6.38(1H, m) 7.54(1H, dd, J=4.5 and 8.0 Hz) 8.56(2H, s) 8.85(1H, dd, J=1.9 and 4.5 Hz) 8.89(1H, dd, J=1.9 and 8.0 Hz) 9.18(1H, s) 12.07(1H, brs).

Example 45

Synthesis of 1-(benzylpiperidine-4-yl)-1,4-dihydro [1,8]naphthylidin-4-one-3-carboxylic acid hydrochloride To an ethanol solution (1.5 ml) of 200 mg (0.51 mmol) of the compound obtained in Example 22, 425 μl of 6N hydrochloric acid was added under an argon atmosphere and stirred at 80° C. for 2 hours. After cooling, the precipitated crystal was recovered by filtration to obtain 189 mg (93%) of the above-identified compound, as a colorless crystal.

IR(KBr)cm$^{-1}$: 2514, 1721, 1615, 1464, 1414. MS(FAB) 364[M(free)+H]$^+$. $^1$H-NMR(DMSO-d$_6$): δ 2.12–2.33(2H, m) 2.10–2.57(2H, m) 3.16–3.39(2H, m) 3.50–3.63(2H, m) 4.30–4.42(2H, m) 5.75–5.95(1H, m) 7.40–7.60(5H, m) 7.78 (1H, dd, J=4.5 and 8.0 Hz) 8.78–8.84(1H, m) 8.88(1H, brs) 9.03–9.09(1H, m) 14.52(1H, m)

Example 46

Synthesis of N-(3,5-dichloropyridin-4-yl)-1-(benzylpiperidin-4-yl)-1,4-dihydro[1,8]naphthylidin-4-one-3-carboxamide The same reaction was carried out as in Example 10, except for using 1-(benzylpiperidin-4-yl)-1,4-dihydro[1,8] naphtyridin-4-one-3-carboxylic acid hydrochloride, instead of (S)-1-(1-benzyloxycarbonylpyrrolidin-3-yl)-1,4-dihydro [1,8]naphtyridin-4-one-3-carboxylic acid, to obtain 136 mg (62%) of the above-identified compound, as a slightly yellow crystal.

IR(KBr)cm$^{-1}$: 2938, 1694, 1648, 1603, 1543, 1488, 1412. MS (FAB) 508[M+H]$^+$. $^1$H-NMR(CDCl$_3$): δ 1.09–2.05(2H, m) 2.12–2.23 (2H, m) 2.26–2.36(2H, m) 3.07–3.15(2H, m) 3.61(2H, s) 5.59–5.71(1H, m) 7.25–7.37(5H, m) 7.51(1H, dd, J=4.5 and 8.0 Hz) 8.56(2H, s) 8.84(1H, dd, J=1.9 and 4.5 Hz) 8.89(1H, dd, J=1.9 and 8.0 Hz) 9.17(1H, s) 12.15(1H, brs)].

Example 47

Synthesis of N-(3,5-dichloropyridin-4-yl)-1-(4-piperidyl)-1,4-dihydro[1,8]naphthylidin-4-one-3-carboxamide hydrochloride To a 3 ml 1,2-dichloroethane solution of 136 mg (0.268 mmol) of the compound obtained in Example 46, 31.8 μl (0.294 mmol) of 1-chloroethyl chloroformate was added at room temperature and heated under reflux for 2 hours, followed by distilling off the solvent under vacuum. Then the residue was diluted with methanol (5 ml) and heated under reflux for 2 hours, followed by distilling off the solvent under vacuum. Then, the residue was washed with diethyl ether to obtain 137 mg (quantitative) of the above-identified compound as a colorless crystal.

IR(KBr)cm$^{-1}$: 2936, 1676, 1613, 1536, 1486. MS(FAB) 418[M(free)+H]$^+$. $^1$H-NMR(MeOH-d$_4$): δ 2.39–2.52(4H, m) 3.30–3.41(2H, m) 3.62–3.70(2H, m) 5.86–5.97(1H, m) 7.68(1H, dd, J=4.5 and 8.0 Hz) 8.63(2H, s) 8.89(1H, dd, J=1.8 and 8.0 Hz) 8.96(1H, d d, J=1.8 and 4.5 Hz) 9.08(1H, s).

Example 48

Synthesis of N-(3,5-dichloropyridin-4-yl)-1-(1-formylpiperidin-4-yl)-1,4-dihydro[1,8]naphthylidin-4-one-3-carboxamide To a 3 ml DMF solution of 65 mg (0.143 mmol) of the compound obtained in Example 47, 5.9 μl (0.157 mmol) of formic acid, 69.5 mg (0.157 mmol) of BOP reagent and 43.8 μl (0.314 mmol) of triethylamine were added at 0° C. and stirred at room temperature for 2 hours. The mixture was diluted with ethyl acetate (15 ml) and, after washing with saturated saline (5 ml), the product was dried over anhydrous sodium sulfate, followed by distilling off the solvent under vacuum. Then, the residue was purified by a silica gel chromatography (methylene chloride/methanol=40/1) to obtain 51 mg (80%) of the above-identified compound as a colorless oily substance.

IR(KBr)cm$^{-1}$: 2928, 1864, 1674, 1614, 1540, 1486, 1414. MS (FAB) 446[M+H]$^+$. $^1$H-NMR(CDCl$_3$): δ 1.95–2.25(4H, m) 2.83–2.93 (1H, m) 3.35–3.45(1H, m) 3.86–3.95(1H, m) 4.70–4.78(1H, m) 5.81–5.92(1H, m) 7.75(1H, dd, J=4.5 and 5.0 Hz) 8.12(1H, s) 8.56(2H, s) 8.85(1H, dd, J=2.0 and 4.5 Hz) 8.90(1H, dd, J=2.0 and 8.0 Hz) 9.03(1H, s) 12.06(1H, brs).

Example 49

Synthesis of benzyl 2-{4-[3-[(3,5-dichloropyridin-4-yl)amino]carbonyl-1,4-dihydro[1,8]naphthylidin-4-one-1-yl]piperidino}acetate To a 4 ml methylene chloride solution of 120 mg (0.264 mmol) of the compound obtained in Example 47, 67 μl (0.422 mmol) of benzyl bromoacetate and 92 μl (0.66 mmol) of triethylamine were added at room temperature and stirred at room temperature for 20 hours. Then, the mixture was diluted with methylene chloride (20 ml) and washed with water (10 ml), followed by drying over anhydrous sodium sulfate and then distilling off the solvent under vacuum. Then, the residue was purified by a silica gel chromatography (methylene chloride/methanol=40/1) to obtain 135 mg (90%) of the above-identified compound as a colorless crystal.

IR(KBr)cm$^{-1}$: 2949, 1746, 1694, 1617, 1556, 1488, 1412. MS (FAB) 566[M+H]$^+$. $^1$H-NMR(CDCl$_3$): δ 2.01–2.11(2H, m) 2.19–2.35 (2H, m) 2.62–2.72(2H, m) 3.11–3.19(2H, m) 3.40(2H, s) 5.20(2H, s) 7.27–7.42(5H, m) 7.52(1H, dd, J=4.5 and 8.0 Hz) 8.55(2H, s) 8.84(1H, dd, J=1.9 and 4.4 Hz) 8.89(1H, dd, J=1.9 and 8.0 Hz) 9.16(1H, s) 12.12(1H, brs).

Example 50

Synthesis of 2-{4-[3-[(3,5-dichloropyridin-4-yl) amino]carbonyl-1,4-dihydro[1,8]naphthylidin-4-one-1-yl}piperidinolacetic acid To a solution of 102 mg (0.18 mmol) of the compound obtained in Example 49 in 4 ml of tetrahydrofuran and 4 ml of methanol, 25 mg of 10% palladium carbon was added and stirred at room temperature and at ordinary atmospheric pressure for 3 hours under hydrogen atmosphere. The catalyst was removed, followed by distilling off the solvent under vacuum to obtain 68 mg (79%) of the above-identified compound as a colorless crystal.

IR(KBr)cm$^{-1}$: 2934, 1686, 1678, 1613, 1546, 1486. MS(FAB) 476[M+H]$^+$. $^1$H-NMR(D$_2$O): δ 2.35–2.45(2H, m) 2.50–2.63(2H, m) 3.30–3.43(2H, m) 3.75–3.86(4H, m) 5.77–5.89(1H, m) 7.69(1H, dd, J=4.5 and 8.0 Hz) 8.32(2H, s) 8.68 (1H, dd, J=1.6 and 8.0 Hz) 8.94(1H, dd, J=1.6 and 4.5 Hz) 9.05(1H, s).

Example 51

Synthesis of N-(3,5-dichloropyridin-4-yl)-1-(1-methylpiperidin-4-yl)-1,4-dihydro[1,8]naphthylidin-4-one-3-carboxamide To a 3 ml ethanol solution of 50 mg (0.11 mmol) of the compound obtained in Example 47, 44.6 μl (37%, 0.55 mmol) of formalin and 6.9 mg (0.11 mmol) of sodium cyanoborohydride were added and stirred at 0° C. for 2 hours. Then, the mixture was diluted with saturated aqueous sodium hydrogen carbonate solution (5 ml), followed by extracting with methylene chloride (15 ml). After drying the solvent was distilled off under vacuum. Then, the residue was purified by a silica gel chromatography (methylene chloride/methanol=20/1) to obtain 45 mg (95%) of the above-identified compound as a colorless crystal.

IR(KBr)cm$^{-1}$: 2944, 2777, 1690, 1616, 1536, 1485, 1414. MS (FAB) 432[M+H]$^+$. $^1$H-NMR(CDCl$_3$): δ 2.00–2.08(2H, m) 2.16–2.43(7H, m) 3.03–3.10(2H, m) 5.53–5.63(1H, m) 7.52(1H, dd, J=4.5 and 8.0 Hz) 8.55(2H, s) 8.84 (1H, dd, J=1.9 and 4.5 Hz) 8.89 (1H, dd, J=1.9 and 8.0 Hz) 9.15(1H, s) 12.13(1H, brs).

Example 52

Synthesis of ethyl 3-(4-methylpiperazine-1-ylamino)-2-(2-chloronicotinoyl)acrylate The same reaction was carried out as in Example 1, except for using 1-amino-4-methylpiperazine, instead of (±)-3-amino-1-methoxycarbonylpyrrolidine to obtain 2.33 g (98%) of the above-identified compound, as a brown crystal.

IR(KBr)cm$^{-1}$: 3186, 2940, 2800, 1690, 1625, 1562, 1397, 1281, 1246. MS(FAB) 353[M+H]$^+$. $^1$H-NMR(CDCl$_3$): δ 0.80 and 0.96(total 3H, t, J=7.1 Hz) 2.06 and 2.33(total 3H, each s) 2.54–2.70(4H, m) 2.94–3.08(4H, m) 3.92–4.07(2H, m) 7.23–7.33(1H, m) 7.49–7.61(1H, m) 8.36–8.51(2H, m) 9.85–9.94(0.2H, m) 11.27–11.38(0.8 H, m).

Example 53

Synthesis of ethyl 1-(4-methylpiperazine-1-yl)-1,4-dihydro[1,8]naphthylidin-4-one-3-carboxylate The same reaction was carried out as in Example 2, except for using ethyl 3-(4-methylpiperazin-1-ylamino)-2-(2-chloronicotinoyl)acrylate, instead of (±)-ethyl 3-(1-methoxycarbonylpyrrolidine-3-ylamino)-2-(2-chloronicotinoyl)acrylate, to obtain 880 mg (44%) of the above-identified compound as a colorless crystal.

IR(KBr)cm$^{-1}$: 2940, 2803, 1684, 1646, 1602, 1418, 1225. MS (FAB) 317[M+H]$^+$. $^1$H-NMR(CDCl$_3$): δ 1.41(3H, t, J=7.1 Hz) 2.40 (3H, brs) 2.38–2.57(2H, m) 2.84–2.94(2H, m) 3.11–3.18(2H, m) 4.40(2H, q, J=7.1 Hz) 4.36–4.48(2H, m) 7.38(1H, dd, J=4.5 and 7.9 Hz) 8.71(1H, dd, J=1.9 and 4.5 Hz) 8.75(1H, dd, J=1.9 and 7.9 Hz) 8.80(1H, s).

Example 54

Synthesis of 1-(4-methylpiperazin-1-yl)-1,4-dihydro[1,8]naphthylidin-4-one-3-carboxylic acid dihydrochloride The same reaction was carried out as in Example 45, except for using ethyl 1-(4-methylpiperazine-1-yl)-1,4-dihydro[1,8]naphthylidin-4-one-3-carboxylate, instead of ethyl 1-(1-benzylpiperidine-3-yl)-1,4-dihydro[1,8]naphthylidin-4-one-3-carboxylate, to obtain 690 mg (91%) of the above-identified compound as a colorless crystal.

IR(KBr)cm$^{-1}$: 3063, 2636, 1725, 1613, 1461, 1427, 1334. MS (FAB) 289[M(free)+H]$^+$. $^1$H-NMR(D$_2$O): δ 3.04(3H, brs) 3.38–3.84(8H, m) 7.65–7.76(1H, m) 8.74–8.84(1H, m) 8.90–8.98(1H, m) 9.05–9.18(1H, m).

Example 55

Synthesis of N-(3,5-dichloropyridin-4-yl)-1-(4-methylpiperazine-1-yl)-1,4-dihydro[1,8]naphthylidin-4-one-3-carboxamide The same reaction was carried out as in Example 10, except for using 1-(4-methylpiperazin-1-yl)-1,4-dihydro[1,8]naphthylidin-4-one-3-carboxylic acid dihydrochloride, instead of (S)-1-(1-benzyloxycarbonylpyrrolidin-3-yl)-1,4-dihydro[1,8]naphtyridin-4-one-3-carboxylic acid, to obtain 242 mg (58%) of the above-identified compound as a colorless crystal.

IR(KBr)cm$^{-1}$: 2937, 1687, 1615, 1601, 1545, 1484, 1420, 1401. MS(FAB) 433[M+H]$^+$. $^1$H-NMR(CDCl$_3$): δ 2.40(3H, s) 2.41–2.51(2H, m) 2.85–2.94(2H, m) 3.15–3.24(2H, m) 4.40–4.51(2H, m) 7.49(1H, dd, J=4.5 and 8.0 Hz) 8.56(2H, s) 8.82(1H, dd, J=1.9 and 4.5 Hz) 8.85(1H, dd, J=1.9 and 8.0 Hz) 9.20(1H, s) 12.00(1H, brs).

Example 56

Synthesis of N-(3,5-dichloropyridin-4-yl)-1-(4-methoxycarbonylpiperazin-1-yl)-1,4-dihydro[1,8]naphthylidin-4-one-3-carboxamide The same reaction was carried out as in Example 23, except for using N-(3,5-dichloropyridin-4-yl)-1-(4-methylpiperazin-1-yl)-1,4-dihydro[1,8]naphtyridin-4-one-3-carboxamide, instead of ethyl 1-(1-benzylpiperidin-3-yl)-1,4-dihydro[1,8]naphthylidin-4-one-3-carboxylate and using methyl chloroformate, instead of benzyl chloroformate, to obtain 85 mg (53%) of the above-identified compound as a colorless crystal.

IR(KBr)cm$^{-1}$: 2961, 1713, 1684, 1618, 1547, 1485, 1404, 1254. MS(FAB) 477[M+H]$^+$. $^1$H-NMR(CDCl$_3$): δ 3.18–3.34(4H, m) 3.77(3H, s) 4.10–4.35(4H, m) 7.52(1H, dd, J=4.5 and 7.9 Hz) 8.56(2H, s) 8.82(1H, dd, J=2.0 and 4.5 Hz) 8.85(1H, dd, J=2.0 and 7.9 Hz) 9.19(1H, s) 11.94(1H, brs).

Example 57

Synthesis of ethyl 3-(1,4-dioxaspiro[4,5]decan-8-ylamino)-2-(2-chloronicotinoyl)acrylate The same reaction was carried out as in Example 1, except for using 1,4-dioxaspiro[4,5]decan-8-amine, instead of (±)-3-amino-1-methoxycarbonylpyrrolidine to obtain 3.7 g (85%) of the above-identified compound as a slightly brown oily substance.

IR(KBr)cm$^{-1}$: 2953, 1698, 1631, 1397, 1110. MS(FAB) 395[M+H]$^+$. $^1$H-NMR(CDCl$_3$): δ 0.78 and 0.92(total 3H, t, J=7.1 Hz) 1.61–1.72(2H, m) 1.79–1.92(4H, m) 2.00–2.12 (2H, m) 3.38–3.50(1 H, m) 3.87–4.00(6H, m) 7.21–7.29(1H, m) 7.50–7.58(1H, m) 8.20–8.32(1H, m) 8.33–8.40(1H, m) 9.63–9.75(0.2H, m) 11.07–11.18(0.8H, m).

Example 58

Synthesis of ethyl 1-(1,4-dioxaspiro[4,5]decan-8-yl)-1,4-dihydro[1,8]naphthylidin-4-one-3-carboxylate The same reaction was carried out as in Example 2, except for using ethyl 3-(1,4-dioxaspiro[4,5]decan-8-ylamino-2-(2-chloronicotinoyl)acrylate, instead of (±)-ethyl 3-(1-methoxycarbonylpyrrolidin-3-ylamino)-2-(2-chloronicotinoyl)acrylate, to obtain 2.8 g (88%) of the above-identified compound as a slightly brown crystal.

IR(KBr)cm$^{-1}$: 2944, 1684, 1638, 1608, 1414, 1328, 1221. MS (FAB) 359[M+H]$^+$. $^1$H-NMR(CDCl$_3$): δ 1.43(3H, t, J=7.1 Hz) 1.84–2.19(8H, m) 4.01(4H, brs) 4.42(2H, q, J=7.1 Hz) 5.55–5.66(1H, m) 7.39(1H, dd, J=4.5 and 8.0 Hz) 8.72(1H, dd, J=1.9 and 4.5 Hz) 8.75(1H, s) 8.80(1H, dd, J=1.9 and 8.0 Hz).

Example 59

Synthesis of 1-(1,4-dioxaspiro[4,5]decan-8-yl)-1,4-dihydro[1,8]naphthylidin-4-one-3-carboxylic acid The same reaction was carried out as in Example 3, except for using ethyl 1-(1,4-dioxaspiro[4,5]decan-8-yl)-1,4-dihydro[1,8]naphtyridin-4-one-3-carboxylate, instead of (±)-ethyl 1-(1-methoxycarbonylpyrrolidin-3-yl)-1,4-dihydro[1,8]naphtyridin-4-one-3-carboxylate, to obtain 1.25 g (90%) of the above-identified compound as a slightly yellow crystal.

$^1$H-NMR(CDCl$_3$): δ 1.83–2.09(6H, m) 2.11–2.26(2H, m) 4.01(4H, s) 5.70–5.81(1H, m) 7.56(1H, dd, J=4.5 and 8.0 Hz) 8.85(1H, dd, J=1.9 and 8.0 Hz) 8.90(1H, dd, J=1.9 and 4.5 Hz) 9.06(1H, s) 14.48–14.51(1H, m).

Example 60

Synthesis of N-(4-pyridyl)-1-(1,4-dioxaspiro[4,5] decan-8-yl)-1,4-dihydro[1,8]naphthylidin-4-one-3-carboxamide The same reaction was carried out as in Example 4, except for using 1-(1,4-dioxaspiro[4,5]decan-8-yl)-1,4-dihydro[1,8]naphtyridin-4-one-3-carboxylic acid, instead of (±)-1-(1-methoxycarbonylpyrrolidin-3-yl)-1,4-dihydro[1,8]naphtyridin-4-one-3-carboxylic acid and using 4-aminopyridine, instead of 2,6-dichloroaniline to obtain 325 mg (88%) of the above-identified compound as a slightly brown crystal.

IR(KBr)cm$^{-1}$: 2954, 1691, 1603, 1530, 1489. MS(FAB) 407[M+H]$^+$. $^1$H-NMR(CDCl$_3$): δ 1.85–2.11(6H, m) 2.15–2.30(2H, m) 4.02(4H, s) 5.66–5.78(1H, m) 7.50–7.56 (1H, m) 7.67–7.72(2H, m) 8.52–8.58(2H, m) 8.85–8.90(2H, m) 9.16(1H, s) 12.32(1H, brs).

Example 61

Synthesis of N-(4-pyridyl)-1-(4-oxocyclohexyl)-1,4-dihydro[1,8]naphthylidin-4-one-3-carboxamide To a 30 ml aqueous solution of 305 mg (0.75 mmol) of the compound obtained in Example 60, 1.5 ml of 1N hydrochloric acid was added and stirred at room temperature for 17 hours and then at 70° C. for 1 hour. Then, 1N aqueous sodium hydroxide solution (1.5 ml) was added, followed by extracting with methylene chloride (80 ml) and, after drying, the solvent was distilled off under vacuum to obtain 82 mg (34%) of the above-identified compound as a colorless crystal.

IR(KBr)cm$^{-1}$: 3520, 2968. 1728, 1692, 1603, 1531, 1490, 1415. MS(FAB) 363[M+H]$^+$. $^1$H-NMR(CDCl$_3$): δ 2.31–2.48(4H, m) 2.62–2.78(4H, m) 6.04–6.16(1H, m) 7.55–7.60(1H, m) 7.65–7.69(2 H, m) 8.52–8.56(2H, m) 8.85–8.90(2H, m) 9.08(1H, s) 12.23(1 H, brs).

Example 62

Synthesis of N-(3,5-dichloropyridin-4-yl)-1-(1-ethoxycarbonylpiperidin-4-yl)-1,4-dihydro[1,8] naphthylidin-4-one-3-carboxamide The same reaction was carried out as in Example 23, except for using N-(3,5-dichloropyridin-4-yl)-1-(benzylpiperidin-4-yl)-1,4-dihydro[1,8]naphthylidin-4-one-3-carboxamide, instead of ethyl 1-(1-benzylpiperidin-3-yl)-1,4-dihydro[1,8]naphtyridin-4-one-3-carboxylate and using ethyl chloroformate, instead of benzyl chloroformate, to obtain 162 mg (84%) of the above-identified compound as a colorless crystal.

IR(KBr)cm$^-$: 2987, 1677, 1617, 1489, 1438, 1234. MS(FAB) 490[M+H]$^+$. $^1$H-NMR(CDCl$_3$): δ 1.31(3H, t, J=7.1 Hz) 1.95–2.12(4H, m) 2.98–3.10(2H, m) 4.20(2H, q, J=7.1 Hz) 4.36–4.52(2H, m) 5.75–5.86(1H, m) 7.54(1H, dd, J=4.5 and 8.0 Hz) 8.56(2H, s) 8.84(1H, dd, J=1.9 and 4.5 Hz) 8.90(1H, dd, J=1.9 and 8.0 Hz) 9.06(1H, s) 12.11(1H, brs).

Example 63

Synthesis of ethyl 3-{trans-[4-(tert-butoxycarbonyl) amino]cyclohexyl}amino-2-(2-chloronicotinoyl) acrylate The same reaction was carried out as in Example 1, except for using tert-butyl N-(trans-4-aminocyclohexyl)carbamate, instead of (±)-3-amino-1-methoxycarbonylpyrrolidine to obtain 5.3 g (quant.) of the above-identified compound as a slightly brown crystal.

IR(KBr)cm$^{-1}$: 3345, 2986, 2942, 1696, 1683, 1619, 1520, 1317. MS(FAB) 452[M+H]$^+$. $^1$H-NMR(CDCl$_3$): δ 0.78 and 0.91(total 3H, t, J=7.1 Hz) 1.16–1.34(2H, m) 1.42–1.48(9H, m) 1.49–1.66(2H, m) 2.05–2.20(4H, m) 3.28–3.38(1H, m) 3.41–3.56(1H, m) 3.89–4.02(2H, m) 4.32–4.46(1H, m) 7.21–7.28(1H, m) 7.48–7.58 (1H, m) 8.17–8.34(1H, m) 8.34–8.45(1H, m) 9.51–9.66(0.15H, m) 10.97–10.9(0.85H, m).

Example 64

Synthesis of ethyl 1-[trans-4-(tert-butoxycarbonyl) amino]cyclohexyl-1,4-dihydro[1,8]naphthylidin-4-one-3-carboxylate The same reaction was carried out as in Example 2, except for using ethyl 3-{trans-[4-(tert-butoxycarbonyl)amino] cyclohexyl}amino-2-(2-chloronicotinoyl)acrylate, instead of (±)-ethyl 3-(1-methoxycarbonylpyrrolidine-3-ylamino)-2-(2-chloronicotinoyl)acrylate, to obtain 3.5 g (89%) of the above-identified compound as a slightly yellow crystal.

IR(KBr)cm$^{-1}$: 3328, 2978, 2934, 1730, 1710, 1622, 1512, 1232. MS(FAB) 416[M+H]$^+$. $^1$H-NMR(CDCl$_3$): δ 1.42(3H, t, J=7.1 Hz) 1.44–1.56(11H, m) 1.83–1.96(2H, brs) 2.05–2.14(2H, m) 2.20–2.29(2H, m) 3.52–3.66(1H, br) 4.36–4.50(1H, m)4.41(2H, q, J=7.1 Hz) 5.44–5.55(1H, m) 7.39(1H, dd, J=4.5 and 7.9 Hz) 8.68(1H, s) 8.71(1H, dd, J=1.9 and 4.5 Hz) 8.80(1H, dd, J=1.9 and 7.9 Hz).

Example 65

Synthesis of ethyl 1-(trans-4-aminocyclohexyl)-1,4-dihydro[1,8]naphthylidin-4-one-3-carboxylate trifluoroacetate To a 4.4 ml methylene chloride solution of 1.2 g (2.89 mmol) of the compound obtained in Example 64, 2.22 ml of trifluoroacetic acid was added at 0° C. and stirred at room temperature for 1 hour and 2.22 ml of trifluoroacetic acid was further added thereto and stirred for 1 hour. The solvent was distilled off the solvent under vacuum. Then, the residue was washed with diethyl ether to obtain 1.3 g (quant.) of the above-identified compound as a colorless foamy substance.

IR(KBr)cm$^{-1}$: 2980, 1732, 1678, 1626, 1205, 1136. MS(FAB) 316[M(free)+H]$^+$. $^1$H-NMR(MeOH-d$_4$): δ 1.39 (3H, t, J=7.1 Hz) 1.68–1.82(2H, m) 2.01–2.31(6H, m) 3.29–3.39(1H, m) 4.36(2H, q, J=7.1 Hz) 5.54–5.67(1H, m)

7.57(1H, dd, J=4.5 and 8.0 Hz) 8.76(1H, dd, J=2.0 and 8.0 Hz) 8.86(1H, dd, J=2.0 and 4.5 Hz) 8.88(1H, s).

Example 66

Synthesis of ethyl 1-[trans-4-(benzyloxycarbonylamino)cyclohexyl]-1,4-dihydro[1,8]naphthylidin-4-one-3-carboxylate To a solution of 1.28 g (2.89 mmol) of the compound obtained in Example 65 in 40 ml of 1,4-dioxane and 20 ml of water, 1.25 ml (8.94 mmol) of triethylamine and 511 μl (3.58 mmol) of benzyloxycarbonyl chloride were added at 0° C., and stirred at 0° C. for 10 minutes and then at room temperature for 1 hour, followed by diluting with methylene chloride (60 ml) and successively washed with water (30 ml) and saturated saline (20 ml). The solvent was distilled off under vacuum. Then, the residue was washed with diethyl ether to obtain 1.06 g (79%) of the above-identified compound as a colorless crystal.

IR(KBr)cm$^{-1}$: 3268, 2941, 1707, 1682, 1634, 1609, 1415, 1206. MS(FAB) 450[M+H]$^+$. $^1$H-NMR(CDCl$_3$): δ 1.43(3H, t, J=7.1 Hz) 1.45–1.54(2H, m) 1.85–2.00(2H, m) 2.08–2.15(2H, m) 2.23–2.32(2H, m) 3.62–3.76(1H, m) 4.41(2H, q, J=7.1 Hz) 4.63–4.73(1H, br) 5.08–5.18(2H, m) 5.45–5.56(1H, m) 7.30–7.45(6H, m) 8.69(1H, s) 8.71(1H, dd, J=1.9 and 4.5 Hz) 8.80(1H, dd, J=1.9 and 7.8 Hz).

Example 67

Synthesis of 1-[trans-4-(benzyloxycarbonylamino)cyclohexyl]-1,4-dihydro[1,8]naphthylidin-4-one-3-carboxylic acid The same reaction was carried out as in Example 3, except for using ethyl 1-[trans-4-(benzyloxycarbonylamino)cyclohexyl]-1,4-dihydro[1,8]naphtyridin-4-one-3-carboxylate, instead of (±)-ethyl 1-(1-methoxycarbonylpyrrolidin-3-yl)-1,4-dihydro[1,8]naphtyridin-4-one-3-carboxylate, to obtain 820 mg (97%) of the above-identified compound as a colorless crystal.

IR(KBr)cm$^{-1}$: 3352, 2944, 1720, 1691, 1618, 1528, 1474, 1230. MS(FAB) 422[M+H]$^+$. $^1$H-NMR(CDCl$_3$): δ 1.49–1.61(2H, m) 1.93–2.06(2H, m) 2.12–2.21(2H, m) 2.28–2.36(2H, m) 3.62–3.74(1 H, m) 4.60–4.71(1H, br) 5.08–5.19(2H, m) 5.58–5.69(1H, m) 7.30–7.42(5H, m) 7.56(1H, dd, J=4.5 and 8.0 Hz) 8.85(1H, dd, J=2.0 and 8.0 Hz) 8.88(1H, dd, J=2.0 and 4.5 Hz) 8.97(1H, s) 14.4(1H, brs).

Example 68

Synthesis of N-(3,5-dichloropyridin-4-yl)-1-[trans-4-(benzyloxycarbonylamino)cyclohexyl]-1,4-dihydro[1,8]naphthylidin-4-one-3-carboxamide The same reaction was carried out as in Example 10, except for using 1-[trans-4-(benzyloxycarbonylamino)cyclohexyl]-1,4-dihydro[1,8]naphtyridin-4-one-3-carboxylic acid, instead of (S)-1-(1-benzyloxycarbonylpyrrolidin-3-yl)-1,4-dihydro[1,8]naphtyridin-4-one-3-carboxylic acid, to obtain 100 mg (74%) of the above-identified compound as a colorless crystal.

IR(KBr)cm$^{-1}$: 2944, 1693, 1618, 1542, 1489, 1412. MS(FAB) 566[M+H]$^+$. $^1$H-NMR(CDCl$_3$): δ 1.45–1.56(2H, m) 1.94–2.11(2H, m) 2.10–2.19(2H, m) 2.24–2.36(2H, m) 3.60–3.74(1H, m) 4.60–4.71(1H, m) 5.05–5.20(2H, m) 5.54–5.65(1H, m) 7.28–7.41(5H, m) 7.51(1H, dd, J=4.5 and 8.0 Hz) 8.56(2H, s) 8.84(1H, dd, J=1.9 and 4.5 Hz) 8.89(1H, dd, J=1.9 and 8.0 Hz) 9.07(1H, s) 12.14(1H, brs).

Example 69

Synthesis of N-(3,5-dichloropyridin-4-yl)-1-(trans-4-aminocyclohexyl)-1,4-dihydro[1,8]naphthylidin-4-one-3-carboxamide acetate To 300 mg (2.89 mmol) of the compound obtained in Example 68, 3 ml of 30% hydrobromic acid was added and stirred at room temperature for 3 hours and diluted with diethyl ether (50 ml) to recover the precipitated crystal by filtration. The resultant crystal was converted to the acetic acid salt to obtain 319 mg (quant.) of the above-identified compound as a colorless crystal.

IR(KBr)cm$^{-1}$: 2949, 1698, 1619, 1545, 1489, 1413. MS(FAB) 360[M(free)+H]$^+$. $^1$H-NMR(DMSO-d$_6$): δ 1.26–1.41(2H, m) 1.87(3 H, s) 1.92–2.04(6H, m) 2.75–2.84(1H, m) 5.41–5.53(1H, m) 7.71(1H, dd, J=4.5 and 8.0 Hz) 8.72(2H, s) 8.80(1H, dd, J≦1.9 and 8.0 Hz) 9.02(1H, dd, J=1.9 and 4.5 Hz) 9.04(1H, s) 12.17(1H, br).

Example 70

Synthesis of N-(3,5-dichloropyridin-4-yl)-1-[trans-4-(acetylamino)cyclohexyl]-1,4-dihydro[1,8]naphthylidin-4-one-3-carboxamide To a 6 ml methylene chloride solution of 62 mg (0.126 mmol) of the compound obtained in Example 69, 17.8 μl (0.189 mmol) of acetic anhydride and 30.6 μl (0.378 mmol) of pyridin were added and stirred at room temperature for 1.5 hours and diluted with 40 ml of ethyl acetate and successively washed with water (10 ml) and saturated saline (5 ml). The solvent was then distilled off under vacuum. Then, the residue was purified by recrystallization from ethanol to obtain 37 mg (62%) of the above-identified compound as a colorless crystal.

IR(KBr)cm$^-$: 3306, 2943, 1696, 1619, 1544, 1490, 1413. MS (FAB) 317[M+H]$^+$. $^1$H-NMR(CDCl$_3$): δ 1.42–1.65(2H, m) 2.00(3H, s) 1.97–2.34(6H, m) 3.85–3.97(1H, m) 5.23–5.34(1H, m) 5.49–5.61(1H, m) 7.48–7.55(1H, m) 8.56(2H, s) 8.79–8.90(2H, m) 9.07(1H, s) 12.13(1H, brs).

Example 71

Synthesis of N-(3,5-dichloropyridin-4-yl)-1-[trans-4-(ethylaminocarbonylamino)cyclohexyl]-1,4-dihydro[1,8]naphthylidin-4-one-3-carboxamide To a 3 ml methylene chloride solution of 56 mg (0.114 mmol) of the compound obtained in Example 69, 31.7 μl (0.227 mmol) of triethylamine and 11.2 μl (0.142 mmol) of ethyl isocyanate were added and stirred at room temperature for 2 hours and 11.2 μl (0.142 mmol) of ethyl isocyanate was further added and stirred at room temperature for 2 hours, followed by diluting with 30 ml of methylene chloride. After washing with 10 ml of water, the solvent was distilled off. Then, the residue was purified by recrystallization from ethanol to obtain 16 mg (28%) of the above-identified compound as a colorless crystal.

IR(KBr)cm$^{-1}$: 3326, 2936, 1695, 1639, 1618, 1556, 1489, 1414. MS(FAB) 503[M+H]$^+$. $^1$H-NMR(DMSO-d$_6$): δ 0.99 (3H, t, J=7.2 Hz) 1.20–1.38(2H, m) 1.95–2.10(5H, m) 2.92–3.05(1H, m) 3.50–3.62(1H, m) 5.39–5.52(1H, m) 5.64–5.73(2H, m) 7.68–7.73(1H, m) 8.72(2H, s) 8.75–8.82 (1H, m) 8.98–9.03(1H, m) 9.08(1H, s) 12.16(1H, brs).

Example 72

Synthesis of N-(3,5-dichloropyridin-4-yl)-1-[trans-4-(methanesulfonylamino)cyclohexyl]-1,4-dihydro[1,8]naphthylidin-4-one-3-carboxamide The same reaction was carried out as in Example 70, except for using methanesulfonyl chloride and triethylamine, instead of acetic anhydride and pyridine, respectively, to obtain 43 mg (53%) of the above-identified compound as a colorless crystal.

IR(KBr)cm$^{-1}$: 3296, 2952, 1698, 1618, 1489, 1413, 1326. MS (FAB) 510[M+H]$^+$. $^1$H-NMR(CDCl$_3$): δ 1.60–1.74(2H, m) 1.99–2.13(2H, m) 2.16–2.25(2H, m) 2.32–2.41(2H, m) 3.04(3H, s) 3.40–3.54(2H, m) 4.16–4.22(1H, m) 5.55–5.65 (1H, m) 7.53(1H, dd, J=4.5 and 8.0 Hz) 8.56(2H, s) 8.84(1H, dd, J=1.9 and 4.5 Hz) 8.89(1H, J=1.9 and 8.0 Hz) 9.06(1H, s) 12.12(1H, brs).

Example 73

Synthesis of (1R,3R)-3-azidocyclopentyl acetate

To a 8 ml DMF solution of 580 mg (2.61 mmol) of (1R,3S)-3-[(methylsulfonyl)oxy]cyclopentyl acetate, 203 mg (3.13 mmol) of sodium azide and 26 μl (0.13 mmol) of 15-crown-5-ether were added and stirred at 80° C. for 3 hours, followed by concentrating and then by diluting with 50 ml of diethyl ether. The residue was washed with 10 ml of saturated saline and then the solvent was distilled off to obtain 360 mg (82%) of the above-identified compound as a slightly brown oily substance.

IR(neat)cm$^{-1}$: 2978, 2360, 2101, 1738, 1732, 1241. $^1$H-NMR(CDCl$_3$): δ 1.67–1.78(2H, m) 2.01(3H, s) 2.00–2.18(4H, m) 4.06–4.15(1H, m) 5.19–5.26(1H, m).

Example 74

Synthesis of ethyl 3-{[(1R,3R)-3-(acetoxy) cyclopentyl]amino}-2-(2-chloronicotinoyl)acrylate To a 10 ml methanol solution of 330 mg (1.95 mmol) of the compound obtained in Example 73, 30 mg of 10% palladium carbon was added and was stirred for 40 minutes under hydrogen atmosphere. Then, after the catalyst was removed, the mother liquor was concentrated to obtain an amine compound as a colorless oily substance.

Then, a mixed solution of 444 mg (1.95 mmol) of ethyl (2-chloronicotinoyl)acetate, 1.84 ml (19.5 mmol) of acetic anhydride and 422 μl (2.54 mmol) of triethyl formate were heated with stirring at 130° C. for 1.5 hours under an argon atmosphere. After cooling, excess amounts of the reagents were distilled off under vacuum to obtain the ethoxy acrylate. Thereafter, to a 20 ml solution of the ethoxy acrylate in methylene chloride, a 2 ml solution of the amine compound in anhydrous methylene chloride was added at 0° C. Further, after stirring at room temperature for 1.5 hours, the solvent was removed. The residue was purified by a silica gel chromatography (hexane/ethyl acetate=1/1) to obtain 620 mg (83%) of the above-identified compound as a slightly brown oily substance.

IR(neat)cm$^{-1}$: 2980, 1738, 1652, 1634, 1600, 1246. $^1$H-NMR(CDCl$_3$): δ 0.78 and 0.92(total 3H, t, J=7.1 Hz) 1.68–2.08(3H, m) 2.05(3H, s) 2.18–2.38(3H, m) 3.85–4.00 (2H, m) 4.04–4.18(1H, m) 5.23–5.31(1H, m) 7.20–7.32(1H, m) 7.48–7.58(1H, m) 8.18–8.34(1H, m) 8.36–8.45(1H, m) 9.64(0.17H, br) 11.08(0.83H, m).

Example 75

Synthesis of ethyl 1-[(1R,3R)-3-(acetoxy) cyclopentyl]-1,4-dihydro[1,8]naphthylidin-4-one-3-carboxylate The same reaction was carried out as in Example 2, except for using ethyl 3-{[(1R,3R)-3-(acetoxy)cyclopentyl] amino}-2-(2-chloronicotinoyl)acrylate, instead of (±)-ethyl 3-(1-methoxycarbonylpyroridin-3-ylamino)-2-(2-chloronicotinoyl)acrylate, to obtain 232 mg (43%) of the above-identified compound as a colorless crystal.

IR(KBr)cm$^{-1}$: 2982, 1736, 1328, 1489, 1417, 1241, 1206. MS (FAB) 345[M+H]$^+$. $^1$H-NMR(CDCl$_3$): δ 1.42(3H, t, J=7.1 Hz) 1.91–2.05(2H, m) 2.10(3H, s) 2.24–2.33(1H, m) 2.36–2.52(3H, m) 4.41(2H, q, J=7.1 Hz) 5.40–5.56(1H, m) 5.90–6.01(1H, m) 7.141(1 H, dd, J=4.5 and 8.0 Hz) 8.69(1H, s) 8.74(1H, dd, J=2.0 and 4.5 Hz) 8.80(1H, dd, J≦2.0 and 8.0 Hz).

Example 76

Synthesis of 1-[(1R,3R)-3-(hydroxy)cyclopentyl]-1, 4-dihydro[1,8]naphthylidin-4-one-3-carboxylic acid To a 5 ml ethanol solution of 212 mg (0.616 mmol) of the compound obtained in Example 75, 1.23 ml (1.23 mmol) of a 1N aqueous sodium hydroxide solution was added and stirred at room temperature for 3 hours, followed by diluting with 15 ml of water and then washed with 10 ml of diethyl ether. Thereafter, 1.25 ml of 1N hydrochloric acid was added to the aqueous phase to be neutralized.

Then, the aqueous phase was extracted with 40 ml of methylene chloride and the solvent was distilled off, to obtain 152 mg (90%) of the above-identified compound as a colorless crystal.

IR(KBr)cm$^{-1}$: 3436, 2944, 1710, 1614, 1474, 1412. MS(FAB) 275[M+H]$^+$. $^1$H-NMR(CDCl$_3$): δ 1.84–1.98(2H, m) 2.11–2.21(1H, s) 2.30–2.41(2H, m) 2.54–2.65(1H, m) 4.64–4.70(1H, brs) 6.21–6.32(1H, m) 7.56(1H, dd, J=4.5 and 8.0 Hz) 8.84(1H, dd, J=2.0 and 8.0 Hz) 8.90(1H, dd, J=2.0 and 4.5 Hz) 8.98(1H, s) 14.5(1H, brs).

Example 77

Synthesis of 1-[(1R,3R)-3-(acetoxy)cyclopentyl]-1, 4-dihydro[1,8]naphthylidin-4-one-3-carboxylic acid To a 6 ml methylene chloride solution of 142 mg (0.518 mmol) of the compound obtained in Example 76, 184 μl (2.59 mmol) of acetyl chloride was added, followed by adding, at room temperature, 184 μl (2.59 mmol) of acetyl chloride three times each for a one hour interval. The mixture was stirred for further 1 hour after the completion of the addition. Then, the solvent was distilled off, to obtain 167 mg (quant.) of the above-identified compound as a slightly brown crystal.

IR(KBr)cm$^{-1}$: 3051, 1732, 1619, 1478, 1416, 1237. MS(FAB) 317[M+H]$^+$. $^1$H-NMR(CDCl$_3$): δ 1.95–2.12(2H, m) 2.10(3H, s) 2.25–2.36(1H, m) 2.42–2.59(3H, m) 5.41–5.49(1H, m) 6.04–6.14(1 H, m) 7.58(1H, dd, J=4.4 and 8.0 Hz) 8.85(1H, dd, J=1.9 and 8.0 Hz) 8.90(1H, dd, J=1.9 and 4.4 Hz) 8.98(1H, s) 14.4(1H, brs).

Example 78

Synthesis of N-(3,5-dichloropyridin-4-yl)-1-[(1R, 3R)-3-(acetoxy)cyclopentyl]-1,4-dihydro[1,8] naphthylidin-4-one-3-carboxamide The same reaction was carried out as in Example 10, except for using 1-[(1R,3R)-3-(acetoxy)cyclopentyl]-1,4-dihydro[1,8]naphthylidin-4-one-3-carboxylic acid, instead of (S)-1-(1-benzyloxycarbonylpyrrolidin-3-yl)-1,4-dihydro [1,8]naphthylidin-4-one-3-carboxylic acid, to obtain 83 mg (40%) of the above-identified compound as a colorless crystal.

IR(KBr)cm$^{-1}$: 2973, 1737, 1694, 1616, 1544, 1488, 1412, 1232. MS(FAB) 461[M+H]$^+$. $^1$H-NMR(CDCl$_3$): δ 1.93–2.16(2H, m) 2.10(3H, s) 2.32–2.56(4H, m) 5.42–5.50 (1H, m) 6.02–6.11(1H, m) 7.54(1H, dd, J=4.5 and 8.0 Hz) 8.56(2H, s) 8.85–8.94(2H, m) 9.08(1H, s) 12.12(1H, brs).

Example 79

Synthesis of N-(3,5-dichloropyridin-4-yl)-1-[(1R, 3R)-3-(hydroxy)cyclopentyl]-1,4-dihydro[1,8] naphthylidin-4-one-3-carboxamide To a 6 ml ethanol solution of 71 mg (0.154 mmol) of the compound obtained in Example 78, 169 μl (0.169 mmol) of a 1N aqueous sodium hydroxide solution and stirred at room temperature for 2 hours, followed by diluting with 15 ml of water and extracted with 30 ml of ethyl acetate. After washing with 5 ml of saturated saline water, the solvent was distilled off and the residue was recrystallized from ethanol, to obtain 39 mg (60%) of the above-identified compound as a colorless crystal.

IR(KBr)cm$^{-1}$: 3498, 2934, 1681, 1604, 1542, 1488. MS(FAB) 419[M+H]$^+$. $^1$H-NMR(CDCl$_3$): δ 1.83–2.05(2H, m) 2.17–2.27(1H, s) 2.32–2.43(2H, m) 2.52–2.65(1H, m) 4.65–4.74(1H, m) 6.19–6.31(1H, m) 7.53(1H, dd, J=4.5 and 7.9 Hz) 8.56(2H, s) 8.84–8.93(2H, m) 9.08(1H, s) 12.16(1H, brs).

Example 80

Synthesis of (5S,7R)-1-aza-7-[(methanesulfonyl) oxy]-3-oxabicyclo[3,3,0]octan-2-one To a 30 ml anhydrous methylene chloride solution of 950 mg (6.64 mmol) of (5S,7R)-1-aza-7-hydroxy-3-oxabicyclo [3,3,0]octan-2-one, 668 μl (8.63 mmol) of methanesulfonyl chloride and 1.38 ml (9.96 mmol) of triethylamine were added at room temperature under an argon atmosphere and stirred at the same temperature for 2 hours. The reaction mixture was diluted with methylene chloride (30 ml) and successively washed with water (20 ml) and saturated saline (20 ml), followed by drying over anhydrous sodium sulfate. The solvent was distilled off under vacuum to obtain 1.05 g (quant.) of the above identified compound as a slightly yellow crystal.

IR(KBr)cm$^-$: 3018, 1758, 1351, 1168, 950.898. MS(FAB) 222[M+1]$^+$. $^1$H-NMR(CDCl$_3$): δ 1.72–1.81(1H, m) 2.44–2.49(1H, m) 3.06(3H, s) 3.39(1H, dd, J=1.1 and 13.7 Hz) 4.12(1H, dd, J=6.0 and 13.7 Hz) 4.16–4.25(2H, m) 4.55–4.60(1H, m) 5.36–5.40(1H, m).

Example 81

Synthesis of (5S,7S)-1-aza-7-azid-3-oxabicyclo[3,3, 0]octan-2-one

To a 80 ml anhydrous dimethylformamide solution of 1.50 g (6.78 mmol) of (5S,7R)-1-aza-7-[(methanesulfonyl) oxy]-3-oxabicyclo[3,3,0]octan-2-one, 660 mg (10.2 mmol) of sodium azide at room temperature under an argon atmosphere and stirred at 60° C. for 2 hours. Then the solvent was distilled off under vacuum and the residue was diluted with methylene chloride (100 ml) and successively washed with water (50 ml) and saturated saline (50 ml), followed by drying over anhydrous sodium sulfate. The solvent was distilled off under vacuum. The residue was purified by a silica gel column chromatography (hexane/ethyl acetate=1/ 3) to obtain 1.08 g (95%) of the above identified compound as a slightly yellow crystal.

IR(KBr)cm$^{-1}$: 3466, 3368, 2106, 1752, 1394, 1217, 777. MS (FAB) 169[M+1]$^+$. $^1$H-NMR(CDCl$_3$): δ 1.75–1.82(1H, m) 2.32–2.40(1H, m) 3.25(1H, dd, J=5.2 and 12.6 Hz) 3.79–3.84(1H, m) 4.05–4.12(1H, m) 4.17(1H, dd, J=4.9 and 8.8 Hz) 4.23–4.28(1H, m) 4.54–4.59(1H, m).

Example 82

Synthesis of ethyl 3-[(5S,7S)-1-aza-3-oxabicyclo[3, 3,0]octan-2-one-7-yl]amino-2-(2-chloronicotinoyl) acrylate To a 100 ml methanol solution of 1.05 g (6.24 mmol) of (5S,7S)-1-aza-7-azid-3-oxabicyclo[3,3,0]octan-2-one, 110 mg of 10% palladium activated carbon was added and was stirred at room temperature for 2 hours under hydrogen atmosphere. Then, after the catalyst was removed by filtration, the mother liquor was concentrated to obtain (5S,7S)-7-amino-1-aza-3-oxabicyclo[3,3,0]octan-2-one.

Then, a mixed solution of 1.18 g (5.18 mmol) of ethyl (2-chloronicotinoyl)acetate, 5.89 ml (62.4 mmol) of acetic anhydride and 1.29 ml (7.78 mmol) of triethyl formate were heated with stirring at 120° C. for 1.5 hours under an argon atmosphere. After cooling, excess amounts of the reagents were distilled off to obtain the ethoxy acrylate. Thereafter, to a 10 ml anhydrous methylene chloride solution of the ethoxy acrylate, a 15 ml methylene chloride solution of (5S,7S)-7-amino-1-aza-3-oxabicyclo[3,3,0]octan-2-one was added at 0° C. under an argon atmosphere and, after stirring at room temperature for 2 hours, the solvent was removed. The residue was purified by a silica gel chromatography (ethyl acetate) to obtain 1.69 g (86%) of the above-identified compound as a colorless crystal.

IR(KBr)cm$^{-1}$: 3218, 2984, 1756, 1684, 1634, 1394, 1079. MS(FAB) 380[M+1]$^+$. $^1$H-NMR(CDCl$_3$): δ 0.81 and 0.92 (total3H, t, J=7.1 Hz) 1.79–1.85(1H, m) 2.55–2.58(1H, m) 3.65–3.71 (2H, m) 3.93 and 3.97(total2H, q, J=7.1 Hz) 4.08–4.34(3H, m) 4.54–4.59(1H, m) 7.20–7.31(1H, m) 7.53 and 7.58(total1H, dd, J=1.9 and 7.6 Hz) 8.15–8.25(1H, m) 8.38(1H, dd, J=1.9 and 4.7 Hz).

Example 83

Synthesis of ethyl 1-[(5S,7S)-1-aza-3-oxabicyclo[3, 3,0]octan-2-one-7-yl]-1,4-dihydro[1,8]naphthylidin-4-one-3-carboxylate The same reaction was carried out as in Example 2, except for using ethyl 3-[(5S,7S)-1-aza- 3-oxabicyclo[3,3,0]octan-2-one-7-yl]-2-(2-chloronicotinoyl)acrylate, instead of (±)-ethyl 3-(1-methoxycarbonylpyrrolidine-3-ylamino)-2-(2-chloronicotinoyl)acrylate, to obtain 1.45 g (97%) of the above-identified compound as a colorless crystal.

IR(KBr)cm$^{-1}$: 3566, 2976, 1748, 1694, 1641, 1230, 1204, 788. MS(FAB) 344[M+1]$^+$. $^1$H-NMR(CDCl$_3$): δ 1.42(3H, t, J=7.1 Hz) 2.50–2.62(2H, m) 3.75–3.81(1H, m) 4.11–4.13 (1H, m) 4.24–4.26(1H, m) 4.33–4.37(1H, m) 4.41(2H, q, J=7.1 Hz) 4.63–4.68(1H, m) 5.38–5.42(1H, m) 7.43(1H, dd, J=4.5 and 7.8 Hz) 8.64(1H, s) 8.72(1H, dd, J=1.9 and 4.5 Hz) 8.78(1H, dd, J=1.9 and 7.8 Hz).

Example 84

Synthesis of 1-[(5S,7S)-1-aza-oxabicyclo[3,3,0] octan-2-one-7-yl]-1,4-dihydro[1,8]naphthylidin-4-one-3-carboxylic acid The same reaction was carried out as in Example 3, except for using ethyl 1-[(5S,7S)-1-aza-3-oxabicyclo[3,3,0]octan- 2-one-7-yl]-1,4-dihydro[1,8]naphtyridin-4-one-3-carboxylate, instead of (±)-1-(1-methoxycarbonylpyrrolidine-3-yl)-1,4-dihydro[1,8]naphtyridin-4-one-3-carboxylate, to obtain 594 mg (65%) of the above-identified compound as a colorless crystal.

IR(KBr)cm$^{-1}$: 3627, 3552, 3064, 1744, 1619, 1456, 1229, 802. MS(FAB) 316[M+1]$^+$. $^1$H-NMR(DMSO-d$_6$): δ 2.54–2.59(1H, m) 3.23–3.28(1H, m) 3.63–3.69(1H, m) 3.83–3.88(1H, m) 1.21–4.33(2H, m) 4.55–4.59(1H, m) 5.79–5.87(1H, m) 7.73(1H, dd, J=4.5 and 8.0 Hz) 8.77(1H, dd, J=1.9 and 8.0 Hz) 8.85(1 H, dd, J=1.9 and 4.5 Hz) 9.18(1H, s) 14.60(1H, brs).

Example 85

Synthesis of N-(4-pyridyl)-1-[(5S,7S)-1-aza-3-oxabicyclo[3,3,0]octan-2-one-7-yl]-1,4-dihydro[1,8]naphthylidin-4-one-3-carboxamide The same reaction was carried out as in Example 4, except for using 1-[(5S,7S)-1-aza-3-oxabicyclo[3,3,0]octan-2-one-7-yl]-1,4-dihydro[1,8]naphtyridin-4-one-3-carboxylic acid, instead of (±)-1-(1-methoxycarbonylpyrrolidine-3-yl)-1,4-dihydro[1,8]naphtyridin-4-one-3-carboxylic acid, and using 4-aminopyridine, instead of 2,6-dichloroaniline, respectively, to obtain 137 mg (63%) of the above-identified compound as a yellow crystal.

IR(KBr)cm$^{-1}$: 3450, 1741, 1688, 1604, 1533, 1498, 1418, 1221. MS(FAB) 392[M+1]$^+$. $^1$H-NMR(CDCl$_3$): δ 2.61–2.63 (2H, m) 3.83(1H, dd, J=9.4 and 12.7 Hz) 4.15(1H, dd, J=4.7 and 12.7 Hz) 4.28–4.39(2H, m) 4.66–4.71(1H, m) 5.38–5.48 (1H, m) 7.55(1H, dd, J=4.6 and 7.8 Hz) 7.66–7.69(2H, m) 8.53–8.55(2H, m) 8.82–8.86(2H, m) 9.02(1H, s) 12.14(1H, brs).

Example 86

Synthesis of N-(3,5-dichloropyridine-4-yl)-1-[(5S,7S)-1-aza-3-oxabicyclo[3,3,0]octan-2-one-7-yl]-1,4-dihydro[1,8]naphthylidin-4-one-3-carboxamide The same reaction was carried out as in Example 10, except for using 1-[(5S,7S)-1-aza-3-oxabicyclo[3,3,0]octan-2-one-7-yl]-1,4-dihydro[1,8]naphtyridin-4-one-3-carboxylic acid, instead of (S)-1-(1-benzyloxycarbonylpyrrolidin-3-yl)-1,4-dihydro[1,8]naphtyridin-4-one-3-carboxylic acid, to obtain 106 mg (43%) of the above-identified compound as a yellow crystal.

IR(KBr)cm$^{-1}$: 2922, 1756, 1684, 1616, 1540, 1488, 1398, 1233. MS(FAB) 460[M+1]$^+$. $^1$H-NMR(CDCl$_3$): δ 2.63–2.66 (2H, m) 3.82(1H, dd, J=9.3 and 12.7 Hz) 4.16(1H, dd, J=4.7 and 12.7 Hz) 4.28–4.31(1H, m) 4.35–4.39(1H, m) 4.65–4.70 (1H, m) 5.33–5.37(1H, m) 7.55(1H, dd, J=4.6 and 8.0 Hz) 8.57(2H, s) 8.84–8.89(2H, m) 9.03(1H, s) 11.97(1H, brs).

Example 87

Synthesis of benzyl (2S,4R)-2-[(dimethylamino)carbonyl]-4-[(methanesulfonyl)oxy]pyrrolidin-1-carboxylate The same reaction was carried out as in Example 80, except for using benzyl (2S,4R)-2-[(dimethylamino)carbonyl]-4-hydroxypyridin-1-carboxylate, instead of (5S,7R)-1-aza-7-hydroxy-3-oxabicyclo[3,3,0]octane-2-one, to obtain 2.25 g (99%) of the above-identified compound as a colorless oily substance.

IR(neat)cm$^{-1}$: 2938, 1694, 1645, 1456, 1360, 1173, 902. MS (FAB) 371[M+1]$^+$. $^1$H-NMR(CDCl$_3$): δ 2.30–2.37(1H, m) 2.47–2.56(1H, m) 2.81(3H, s) 2.99(1.5H, s) 3.00(1.5H, s) 3.04(1.5H, s) 3.17(1.5H, s) 3.76–3.97(2H, m) 4.78–4.94(1H, m) 4.99–5.21(2H, m) 5.34–5.60(1H, m) 7.30–7.52(5H, m).

Example 88

Synthesis of benzyl (2S,4S)-2-[(dimethylamino)carbonyl]-4-azidpyrrolidin-1-carboxylate The same reaction was carried out as in Example 81, except for using benzyl (2S,4R)-2-[(dimethylamino)carbonyl]-4-[(methanesulfonyl)oxy]pyrrolidine-1-carboxylate, instead of (5S,7R)-1-aza-7-[(methanesulfonyl)oxy]-3-oxabicyclo[3,3,0]octan-2-one, to obtain 800 mg (47%) of the above-identified compound as a colorless oily substance.

IR(neat)cm$^{-1}$: 2947, 2104, 1715, 1645, 1417, 1360, 1118. MS(FAB) 318[M+1]$^+$. $^1$H-NMR(CDCl$_3$): δ]1.93–1.20(1H, m) 2.53–2.60(1H, m) 2.84(1.5H, s) 2.86(1.5H, s) 3.00(1.5H, s) 3.10(1.5H, s) 3.48–3.53(1H, m) 3.94–4.09(2H, m) 4.61–4.75 (1H, m) 5.00–5.22(2H, m) 7.25–7.52(5H, m).

Example 89

Synthesis of ethyl 3-[(3S,5S)-(1-benzyloxycarbonyl-5-dimethylaminocarbonyl)pyrrolidinyl]amino-2-(2-chloronicotinoyl)acrylate To a 15 ml methanol solution of 700 mg (2.21 mmol) of benzyl (2S,4S)-2-[(dimethylamino)carbonyl]-4-azidpyrrolidin-1-carboxylate, 150 mg of Lindlar catalyst was added and was stirred at room temperature for 1 hour under hydrogen atmosphere. Then, after the catalyst was removed by filtration, the mother liquor was concentrated to obtain benzyl (2S,4S)-4-amino-2-[(dimethylamino)carbonyl]pyrrolidin-1-carboxylate.

Then, a mixed solution of 479 mg (2.11 mmol) of ethyl (2-chloronicotinoyl)acetate, 2.83 ml (30.0 mmol) of acetic anhydride and 500 μl (3.0 mmol) of triethyl formate were heated with stirring at 120° C. for 1.5 hours under an argon atmosphere. After cooling, excess amounts of the reagents were distilled off under vacuum to obtain the ethoxy acrylate. Thereafter, to a 3 ml anhydrous methylene chloride solution of the ethoxy acrylate, a 10 ml methylene chloride solution of benzyl (2S,4S)-4-amino-2-[(dimethylamino)carbonyl]pyrrolidin-1-carboxylate was added at 0° C. under an argon atmosphere after stirring at room temperature for 2 hours, the solvent was removed. The residue was purified by a silica gel chromatography (ethyl acetate) to obtain 950 mg (86%) of the above-identified compound as a colorless crystalline.

IR(KBr)cm$^{-1}$: 3166, 1704, 1624, 1568, 1394, 1235, 757. MS (FAB) 529[M+1]$^+$. $^1$H-NMR(CDCl$_3$): δ 0.89(3H, t, J=7.0 Hz) 2.03–2.18(1H, m) 2.52–2.65(1H, m) 2.82(1.5H, s) 2.89(5H, s) 3.04–3.25(3H, m) 3.74–4.15(5H, m) 4.92–5.17 (3H, m) 7.20–7.35(6H, m) 7.51–7.58(1H, m) 8.06–8.90(1H, m) 8.33–8.36(1H, m) 11.41(1H, brs).

Example 90

Synthesis of ethyl 1-[(3S,5S)-(1-benzyloxycarbonyl-5-dimethylaininocarbonyl)pyrrolidin-3-yl]-1,4-dihydro[1,8]naphthylidin-4-one-3-carboxylate The same reaction was carried out as in Example 2, except for using ethyl 3-[(3S,5S)-(1-benzyloxycarbonyl-5-dimethylaminocarbonyl)pyrrolidinyl]amino-2-(2-chloronicotinoyl)acrylate, instead of (±)-ethyl 3-(1- methoxycarbonylpyrrolidin-3-ylamino)-2-(2-chloronicotinoyl)acrylate, to obtain 630 mg (73%) of the above-identified compound as a slightly yellow crystal.

IR(KBr)cm$^{-1}$: 2952, 1695, 1646, 1486, 1417, 788. MS(FAB) 493[M+1]$^+$. $^1$H-NMR(CDCl$_3$): δ 1.41(3H, t, J=7.1 Hz) 1.44–1.57(1H, m) 2.30–2.34(1H, m) 2.87(3H, brs) 3.05(1.5H, s) 3.20(1.5H, s) 3.81–3.84(1H, m) 4.30–4.41 (1H, m) 4.40(2H, q, J=7.1 Hz) 4.84–5.23(3H, m) 6.16–6.26 (1H, m) 7.25–7.43(6H, m) 8.68–8.71 (1H, m) 8.77–8.80(1H, m) 8.92–8.98(1H, m).

Example 91

Synthesis of 1-[(3S,5S)-(1-benzyloxycarbonyl-5-dimethylaminocarbonyl)pyrrolidin-3-yl]-1,4-dihydro[1,8]naphthylidin-4-one-3-carboxylic acid The same reaction was carried out as in Example 3, except for using ethyl 1-[(3S,5S)-(1-benzyloxycarbonyl-5-dimethylaminocarbonyl)pyrrolidin-3-yl]-1,4-dihydro[1,8] naphtyridin-4-one-3-carboxylate, instead of (±)-1-(1-methoxycarbonylpyrrolidin-3-yl]-1,4-dihydro[1,8] naphtyridin-4-one-3-carboxylate, to obtain 461 mg (81%) of the above-identified compound as a colorless crystal.

IR(KBr)cm$^{-1}$: 3520, 1710, 1621, 1421, 1349, 796. MS(FAB) 465[M+1]$^+$. $^1$H-NMR(CDCl$_3$): δ 2.41–2.58(1H, m) 2.83–2.95(1 H, m) 2.89(3H, brs) 3.06(1.5H, s) 3.21 (1.5H, s) 3.79–3.90(1H, m) 4.31–4.51 (1H, m) 4.82–5.23 (3H, m) 6.07–6.25(1H, m) 7.30–7.19(5H, m) 7.53–7.59(1H, m) 8.81–8.89(2H, m) 9.13–9.2(1H, m) 14.17–14.22(1H, m).

Example 92

Synthesis of N-(3,5-dichloropyridin-4-yl)-1-[(3S, 5S)-(1-benzyloxycarbonyl-5-dimethylaminocarbonyl)pyrrolidin-3-yl]-1,4-dihydro [1,8]naphthylidin-4-one-3-carboxamide The same reaction was carried out as in Example 10, except for using 1-[(3S,5S)-(1-benzyloxycarbonyl-5-dimethylaminocarbonyl)pyrrolidin-3-yl]-1,4-dihydro[1,8] naphtyridin-4-one-3-carboxylic acid, instead of (S)-1-(1-benzyloxycarbonyl pyrrolidin-3-yl)-1,4-dihydro[1,8] naphtyridin-4-one-3-carboxylic acid, to obtain 198 mg (76%) of the above-identified compound as a yellow crystal.

IR(KBr)cm$^{-1}$: 2944, 1694, 1616, 1541, 1486, 1415, 1343, 1222, 1121, 791. MS(FAB) 609[M+1]$^+$. $^1$H-NMR(CDCl$_3$): δ 2.50–2.67(1H, m) 2.81–2.93(1H, m) 2.89(3H, s) 3.05 (1.5H, s) 3.19(1.5H, s) 3.80–3.90(1H, m) 4.32–4.53(1H, m) 4.83–5.22(3H, m) 6.01–6.18(1H, m) 7.29–7.35(5H, m) 7.51–7.55(1H, m) 8.55(2H, s) 8.82–8.84(1H, m) 8.86–8.89 (1H, m) 9.21–9.24 (1H, m) 11.96–12.00(1H, m).

Example 93

Synthesis of N-(3,5-dichloropyridin-4-yl)-1-[(3S, 5S)-(5-dimethylaminocarbonyl)pyrrolidin-3-yl]-1,4-dihydro[1,8]naphthylidin-4-one-3-carboxamide To a 15 ml methanol solution of 100 mg (0.16 mmol) of N-(3,5-dichloropyridin-4-yl)-1-[(3S,5S)-(1-benzyloxycarbonyl-5-dimethylaminocarbonyl)pyrrolidin-3-yl]-1,4-dihydro[1,8]naphthylidin-4-one-3-carboxamide, 20 mg of 10% palladium activated carbon and stirred at room temperature overnight under a hydrogen atmosphere. Then, after the catalyst was removed by filtration, the mother liquor was concentrated and the residue was purified by a silica gel column chromatography (methylene chloride/methanol=5/1), to obtain 45 mg (58%) of the above-identified compound as a colorless crystal.

IR(KBr)cm$^{-1}$: 2925, 1688, 1614, 1540, 1485, 1413, 1335, 1219, 790. MS(FAB) 475[M+1]$^+$. $^1$H-NMR(CDCl$_3$): δ 2.32–2.39(1 H, m) 2.73–2.79(1H, m) 3.03(3H, s) 3.08(3H, s) 3.53–3.55 (2H, m) 4.16–4.19(1H, m) 5.89–5.94(1H, m) 7.53(1H, dd, J=4.6 and 8.0 Hz) 8.55(2H, s) 8.57(1H, dd, J=1.9 and 4.6 Hz) 8.88(1H, dd, J=1.9 and 8.0 Hz) 9.17(1H, s) 12.05(1H, brs).

Example 94

Synthesis of 4-hydroxytetrahydrothiopyran

To a mixed solution of 15.0 g (0.13 mol) of tetrahydrothiopyran-4-one in 100 ml of ethanol and 100 ml of tetrahydrofuran, 2.44 g (0.06 mol) of sodium borohydride was added at 0° C. and stirred at room temperature for 2 hours under an argon atmosphere. The solvent of the reaction solution was distilled off under vacuum, diluted with ethyl acetate (200 ml), and successively washed with water (100 ml) and saturated saline (100 ml), dried over anhydrous sodium sulfate and the solvent was distilled off under vacuum. The residue was purified by a silica gel column chromatography (hexane/ethyl acetate=1/2) to obtain 14.6 g (96%) of the above-identified compound, as a colorless crystal.

IR(KBr)cm$^{-1}$: 3282, 2929, 1428, 1338, 1271, 1058. MS(FAB) 119[M+1]$^+$. $^1$H-NMR(CDCl$_3$): δ 1.40(1H, d, J=4.4 Hz) 1.66–1.76(2H, m) 2.13–2.20(2H, m) 2.55–2.63 (2H, m) 2.75–2.81(2 H, m) 3.63–3.69(1H, m).

Example 95

Synthesis of 4-(methanesulfonyl)oxytetrahydrothiopyran

To a 300 ml methylene chloride solution of 14.6 g (0.12 mol) of 4-hydroxytetrahydrothiopyran, 11.5 ml (0.15 mol) of methanesulfonyl chloride and 25.8 ml (0.19 mol) of triethylamine were added at 0° C. and stirred at room temperature for 1 hour. The reaction mixture was diluted with methylene chloride (100 ml) and successively washing with water (100 ml) and saturated saline (100 ml), followed by drying over anhydrous sodium sulfate. The solvent was then distilled off under vacuum to obtain 24.5 g (quant.) of the above-identified compound as a slightly brown crystal.

IR(KBr)cm$^{-1}$: 3017, 2933, 1346, 1173, 963, 850. MS(FAB) 197[M+1]$^+$. $^1$H-NMR(CDCl$_3$): δ 2.07–2.26(4H, m) 2.55–2.63(2 H, m) 2.83–2.90(2H, m) 3.03(3H, s) 4.77–34.82(1H, m).

Example 96

Synthesis of 4-aminotetrahydrothiopyran hydrochloride

To a 80 ml dimethylformamide solution of 2.60 g (13.2 mmol) of 4-(methanesulfonyl)oxytetrahydrothiopyran, 1.51 g (15.9 mmol) of sodium diformylimide was added at room temperature and stirred at 130° C. for 2.5 hours. The solvent was distilled off under vacuum from the reaction mixture. The reaction mixture was then diluted with methylene chloride (150 ml) and successively washing with water (50 ml) and saturated saline (50 ml), followed by drying over anhydrous sodium sulfate. The solvent was distilled off under vacuum to obtain the diformyl imide product.

To a 60 ml ethanol solution of this diformyl imide product, 8.4 ml of conc. sulfuric acid was added at room temperature and stirred at 80° C. for 18 hours. The solvent was distilled off under vacuum. Then, the residue was washed with diethyl ether to obtain 920 mg (45%) of the above-identified compound, as a brown crystal.

MS(FAB) 118[M+1]$^+$. $^1$H-NMR(DMSO-d$_6$): δ 1.58–168 (2H, m) 2.19–2.24(2H, m) 2.65–2.69(2H, m) 2.99–3.08(1H, m) 3.29–3.42(2H, m).

Example 97

Synthesis of ethyl 3-(4-tetrahydrothiopyranylamino)-2-(2-chloronicotinoyl)acrylate The same reaction was carried out as in Example 1, except for using 4-aminotetrahydrothiopyran hydrochloride and triethyl amine, instead of (±)-3-amino-1-methoxycarbonylpyrrolidine to obtain 740 mg (44%) of the above-identified compound as a colorless crystal.

IR(KBr)cm$^{-1}$: 3221, 1688, 1616, 1553, 1392, 1315, 1255, 1133. MS(FAB) 355[M+1]$^+$. $^1$H-NMR(CDCl$_3$): δ 0.79 and 0.92(total3H, t, J=7.1 Hz) 1.85–1.95(2H, m) 2.31–2.37(2H, m) 2.70–2.81(4H, m) 3.33–3.41(1H, m) 3.92 and 3.97 (total2H, q, J=7.1 Hz) 7.23–7.27(1H, m) 7.52 and 7.56 (total1H, dd, J=1.8 and 7.4 Hz) 8.18–8.32(1H, m) 8.37(1H, dd, J=1.8 and 4.8 Hz) 11.13(1H, brs).

Example 98

Synthesis of ethyl 1-(4-tetrahydrothiopyranyl)-1,4-dihydro[1,8]naphthylidin-4-one-3-carboxylate The same reaction was carried out as in Example 2, except for using ethyl 3-(4-tetrahydrothiopyranylamino)-2-(2-chloronicotinoyl)acrylate, instead of (±)-ethyl 3-(1-methoxycarbonylpyrrolidin-3-ylamino)-2-(2-chloronicotinoyl)acrylate, to obtain 570 mg (90%) of the above-identified compound as a colorless crystal.

IR(KBr)cm$^{-1}$: 2982, 1728, 1627, 1487, 1410, 1207, 1092, 791. ME(FAB) 319[M+1]$^+$. $^1$H-NMR(CDCl$_3$): δ 1.43(3H, t, J=7.1 Hz) 2.14–2.23(2H, m) 2.31–2.35(2H, m) 2.81–2.85 (2H, m) 2.99–3.05(2H, m) 4.42(2H, q, J=7.1 Hz) 5.52–5.56 (1H, m) 7.41 (1H, dd, J=4.5 and 7.9 Hz) 8.67–8.72(1H, m) 3.72(1H, s) 8.80(1H, dd, J=1.9 and 7.9 Hz).

Example 99

Synthesis of 1-(4-tetrahydrothiopyranyl)-1,4-dihydro[1,8]naphthylidin-4-one-3-carboxylic acid The same reaction was carried out as in Example 3, except for using ethyl 1-(4-tetrahydrothiopyranyl)-1,4-dihydro[1,8]naphtyridin-4-one-3-carboxylate, instead of (±)-1-(1-methoxycarbonylpyrrolidine-3-yl)-1,4-dihydro[1,8]naphtyridin-4-one-3-carboxylate, to obtain 269 mg (98%) of the above-identified compound as a colorless crystal.

IR(KBr)cm$^{-1}$: 2911, 1715, 1622, 1456, 1412, 786. MS(FAB) 291[M+1]$^+$. $^1$H-NMR(CDCl$_3$): δ 2.17–2.38(4H, m) 2.81–2.85(2H, m) 2.99–3.04(2H, m) 5.61–5.71(1H, m) 7.57(4H, dd, J=4.5 and 7.9 Hz) 8.84–8.90(2H, m) 9.01(1H, s) 14.38 (1H, brs).

Example 100

Synthesis of N-(4-pyridyl)-1-(4-tetrahydrothiopyranyl)-1,4-dihydro[1,8]naphthylidin-4-one-3-carboxamide The same reaction was carried out as in Example 4, except for using 1-(4-tetrahydrothiopyranyl)-1,4-dihydro[1,8]naphtyridin-4-one-3-carboxylic acid and 4-aminopyridine, instead of (±)-1-(1-methoxycarbonylpyrrolidine-3-yl)-1,4-dihydro[1,8]naphtyridin-4-one-3-carboxylic acid and 2,6-dichloroaniline, respectively, to obtain 109 mg (87%) of the above-identified compound as a slightly yellow crystal.

MS(FAB) 367[M+1]$^+$. $^1$H-NMR(CDCl$_3$): δ 2.25–2.40 (4H, m) 2.83–2.88(2H, m) 3.02–3.09(2H, m) 5.62–5.68(1H, m) 7.53(1H, dd, J=4.5 and 7.8 Hz) 7.67–7.70(2H, m) 8.52–8.55(2H, m) 8.82–8.80(2H, m) 9.12(1H, s) 12.25(1H, brs).

Example 101

Synthesis of N-(3,5-dichloropyridin-4-yl)-1-(4-tetrahydrothiopyranyl)-1,4-dihydro[1,8]naphthylidin-4-one-3-carboxamide The same reaction was carried out as in Example 10, except for using 1-(4-tetrahydrothiopyranyl)-1,4-dihydro[1,8]naphtyridin-4-one-3-carboxylic acid, instead of (S)-1-(1-benzyloxycarbonylpyrrolidin-3-yl-1,4-dihydro[1,8]naphtylidin-4-one-3-carboxylic acid, to obtain 178 mg (85%) of the above-identified compound as a yellow crystal.

IR(KBr)cm$^{-1}$: 2916, 1681, 1620, 1538, 1486, 1410. MS(FAB) 435[M+1]$^+$. $^1$H-NMR(CDCl$_3$): δ 2.26–2.38(4H, m) 2.82–2.86 (2H, m) 2.98–3.07(2H, m) 5.60–5.69(1H, m) 7.53(1H, dd, J=4.5 and 8.0 Hz) 8.56(2H, s) 8.84(1H, dd, J=1.9 and 4.5 Hz) 8.90(1H, dd, J=1.9 and 8.0 Hz) 9.11(1H, s) 12.12(1H, brs).

Example 102

Syntheses of N-(3,5-dichloropyridin-4-yl)-1-(1-oxotetrahydrothiopyran-4-yl)-1,4-dihydro[1,8]naphthylidin-4-one-3-carboxamide (sulfoxide) and N-(3,5-dichloropyridin-4-yl)-1-(1,1-dioxotetrahydrothiopyran-4-yl)-1,4-dihydro[1,8]naphthylidin-4-one-3-carboxamide (sulfone)

To a 4 ml methylene chloride solution of 100 mg (0.23 mmol) of N-(3,5-dichloropyridin-4-yl)-1-(4-tetrahydrothiopyranyl)-1,4-dihydro[1,8]naphtyridin-4-one-3-carboxamide, 50 mg (0.23 mmol) of m-chloroperbenzoic acid (80%) was added at 0° C. and stirred at room temperature for 3 hours. The reaction mixture was diluted with methylene chloride (30 ml) and successively washed with an aqueous sodium bisulfite-sodium hydrogen carbonate solution (10 ml) and water (10 ml), followed by drying over anhydrous sodium sulfate. The solvent was distilled off under vacuum. The residue was purified by a silica gel column chromatography (methylene chloride/methanol=20/1), to obtain 94 mg (90%) of the sulfoxide and 14 mg (13%) of the sulfone of the above-identified compounds as slightly yellow crystals.

Sulfoxide

IR(KBr)cm$^{-1}$: 2924, 1684, 1616, 1540, 1488, 1412, 1024. MS(FAB) 451[M+1]$^+$. $^1$H-NMR(CDCl$_3$): δ 2.09–2.13(1H, m) 2.39–2.46(2H, m) 2.75–3.09(3H, m) 3.29–3.32(1H, m) 3.58–3.63 (1H, m) 5.71–5.88(1H, m) 7.55–7.59(1H, m) 8.46–8.57(2H, m) 8.82–8.91(2H, m) 8.98 and 9.20(total1H, s) 11.98 and 12.03(total1H, brs).

Sulfone

IR(KBr)cm$^{-1}$: 1688, 1616, 1544, 1488, 1286, 1126. MS(FAB) 467[M+1]$^+$. $^1$H-NMR(CDCl$_3$): δ 2.39–2.43(2H, m) 2.82–2.92 (2H, m) 3.28–3.41(4H, m) 5.82–5.91(1H, m) 7.57(1H, dd, J=4.5 and 8.0 Hz) 8.57(2H, s) 8.85(1H, dd, J=1.9 and 4.5 Hz) 8.91(1H, dd, J=1.9 and 8.0 Hz) 9.08(1H, s) 11.98(1H, brs).

Example 103

Synthesis of ethyl 3-(1-morpholinoamino)-2-(2-chloronicotinoyl)acrylate

The same reaction was carried out as in Example 1, except for using 4-aminomorpholine, instead of (±)-3-amino-1- methoxycarbonylpyrrolidine, to obtain 750 mg (88%) of the above-identified compound as a colorless crystal.

IR(KBr)cm$^{-1}$: 3166, 1699, 1633, 1575, 1394, 1231, 1112. MS(FAB) 340[M+1]$^+$. $^1$H-NMR(CDCl$_3$): δ 0.81 and 0.97 (total3H, t, J=7.1 Hz) 2.92–2.30(4H, m) 3.80–3.84(4H, m) 3.93 and 3.99(total2H, q, J=7.1 Hz) 7.23–7.28(1H, m) 7.52 and 7.58(total1H, dd, J=1.9 and 7.5 Hz) 8.38(1H, dd, J=1.9 and 4.9 Hz) 8.40–8.50(1H, m) 11.30 and 11.33(total1H, brs).

Example 104

Synthesis of ethyl 1-(1-morpholino)-1,4-dihydro[1,8]naphthylidin-4-one-3-carboxylate The same reaction was carried out as in Example 2, except for using ethyl 3-(1-morpholinoamino)-2-(2-chloronicotinoyl)acrylate, instead of (±)-ethyl 3-(1-methoxycarbonylpyrrolidin-3-ylamino)-2-(2-chloronicotinoyl)acrylate to obtain 1.55 g (91%) of the above-identified compqound as a slightly yellow crystal.

IR(KBr)cm$^{-1}$: 3072, 2952, 1737, 1603, 1430, 1203, 1102, 796. MS(FAB) 304[M+1]$^+$. $^1$H-NMR(CDCl$_3$): δ 1.42(3H, t, J=7.1 Hz) 3.09–3.11(2H, m) 3.78–3.82(2H, m) 3.98–4.02 (2H, m) 4.40(2H, q, J=7.1 Hz) 4.38–4.45(2H, m) 7.41 (1H, dd, J=4.5 and 7.8 Hz) 8.73(1H, dd, J=1.8 and 4.5 Hz) 8.77(1H, dd, J=1.8 and 7.8 Hz) 8.81(1H, s).

Example 105

Synthesis of 1-(1-morpholino)-1,4-dihydro[1,8]naphthylidin-4-one-3-carboxylic acid The same reaction was carried out as in Example 3, except for using ethyl 1-(1-morpholino)-1,4-dihydro[1,8]naphtyridin-4-one-3-carboxylate, instead of (±)-1-(1-methoxycarbonylpyrrolidin-3-yl)- 1,4-dihydro[1,8]naphtylidin-4-one-3-carboxylate, to obtain 795 mg (73%) of the above-identified compound as a colorless crystal.

IR(KBr)cm$^{-1}$: 3061, 1710, 1622, 1510, 1472, 1105, 799. MS (FAB) 276[M+1]$^+$. $^1$H-NMR(CDCl$_3$): δ 3.11–3.15(2H, m) 3.79–3.82(2H, m) 3.99–4.02(2H, m) 4.40–4.44(2H, m) 7.57(1H, dd, J=4.5 and 8.0 Hz) 8.83(1H, dd, J=2.0 and 8.0 Hz) 8.90(1H, dd, J=2.0 and 4.5 Hz) 9.14(1H, s) 14.18(1H, brs).

Example 106

Synthesis of N-(4-pyridyl)-1-(1-morpholino)-1,4-dihydro[1,8]naphthylidin-4-one-3-carboxamide The same reaction was carried out as in Example 4, except for using 1-(1-morpholino)-1,4-dihydro[1,8]naphtyridin-4-one-3-carboxylic acid and 4-aminopyridine, instead of (±)-1-(1-methoxycarbonylpyrrolidin-3-yl)-1,4-dihydro[1,8]naphtyridin-4-one-3-carboxylic acid and 2,6-dichloroaniline, respectively, to obtain 24 mg (13%) of the above-identified compound as a slightly yellow crystal.

IR(KBr)cm$^{-1}$: 2968, 1688, 1585, 1530, 1487, 1403, 1102. MS(FAB) 352[M+1]$^+$. $^1$H-NMR(CDCl$_3$): δ 3.12–3.16(2H, m) 3.80–3.85(2H, m) 4.00–4.02(2H, m) 4.40–4.45(2H, m) 7.53(1H, dd, J=4.5 and 8.0 Hz) 7.67–7.69(2H, m) 8.53–8.55 (2H, m) 8.83(1H, dd, J=2.0 and 8.0 Hz) 8.86(1H, dd, J=2.0 and 4.5 Hz) 9.21(1H, s) 12.14(1H, brs).

Example 107

Synthesis of N-(3,5-dichloropyridin-4-yl)-1-(1-morpholino)-1,4-dihydro[1,8]naphthylidin-4-one-3-carboxamide The same reaction was carried out as in Example 10, except for using 1-(1-morpholino)- 1,4-dihydro[1,8]naphtyridin-4-one-3-carboxylic acid, instead of (S)-1-(1-benzyloxycarbonylpyrrolidin-3-yl)-1,4-dihydro[1,8]naphtyridin-4-one-3-carboxylic acid to obtain 190 mg (83%) of the above-identified compound as a slightly yellow crystal.

IR(KBr)cm$^{-1}$: 2859, 1691, 1600, 1541, 1508, 1418, 1323, 1110, 792. MS(FAB) 420[M+1]$^+$. $^1$H-NMR(CDCl$_3$): δ 3.14–3.16(2 H, m) 3.78–3.85(2H, m) 4.00–4.03(2H, m) 4.42–4.47(2H, m) 7.53(1H, dd, J=4.8 and 7.7 Hz) 8.56–8.88 (2H, m) 9.22(1H, s) 11.97(1H, brs).

Example 108

Synthesis of ethyl 3-[(trans-4-hydroxycvclohexyl)aminol-2-(2-chloronicotinoyl)acrylate The same reaction was carried out as in Example 1, except for using trans-4-aminocyclohexanol, instead of (±)-3-amino-1-methoxycarbonylpyrrolidine to obtain 7.24 g (93%) of the above-identified compound as a slightly yellow crystal.

IR(KBr)cm$^{-1}$: 3442, 2940, 1688, 1620, 1552, 1393, 1257, 1137. MS(FAB) 353[M+1]$^+$. $^1$H-NMR(CDCl$_3$): δ 0.78 and 0.92(total3H, t, J=7.2 Hz) 1.40–1.60(5H, m) 2.06–2.17(4H, m) 3.37–3.40(1H, m) 3.69–3.75(1H, m) 3.90 and 3.97 (total2H, q, J=7.2 Hz) 7.22–7.26(1H, m) 7.52 and 7.56 (total1H, dd, J=1.9 and 7.5 Hz) 8.20–8.35(1H, m) 8.36(1H, dd, J=1.9 and 4.8 Hz) 9.62 and 11.10(total1H, brs).

Example 109

Synthesis of ethyl 1-(trans-4-hydroxycyclohexyl)-1,4-dihydro[1,8]naphthylidin-4-one-3-carboxylate The same reaction was carried out as in Example 2, except for using ethyl 3-[(trans-4-hydroxycyclohexyl)amino]-2-(2-chloronicotinoyl)acrylate, instead of (±)-ethyl 3-(1-methoxycarbonylpyrrolidin- 3-ylamino)-2-(2-chloronicotinoyl)acrylate, to obtain 4.66 g (80%) of the above-identified compound as a colorless crystal.

IR(KBr)cm$^{-1}$: 3334, 2930, 1730, 1685, 1619, 1492, 1416, 1219, 1082, 790. MS(FAB) 317[M+1]$^+$. $^1$H-NMR(CDCl$_3$): δ 1.43(3H, t, J=7.1 Hz) 1.61–1.72(3H, m) 1.82–1.93(2H, m) 2.09–2.24(4H, m) 3.77–3.85(1H, m) 4.42(2H, q, J=7.1 Hz) 5.49–5.58 (1H, m) 7.41 (1H, dd, J=4.5 and 7.8 Hz) 8.70(1H, s) 8.74(1H, dd, J=2,0 and 4.5 Hz) 8.80(1H, dd, J=2.0 and 7.8 Hz).

Example 110

Synthesis of ethyl 1-[trans-4-(t-butyldiphenylsilyloxy)cyclohexyl]-1,4-dihydro[1,8]naphthylidin-4-one-3-carboxylate To a 120 ml dimethylformamide solution of 4.59 g (14.5 mmol) of ethyl 1-(trans-4-hydroxycyclohexyl)-1,4-dihydro [1,8]naphthylidin-4-one-3-carboxylate and 4.53 ml (17.4 mmol) of t-butyldiphenylsilyl chloride and 1.98 g (29.0 mmol) of imidazole were added at room temperature and stirred at 50° C. for one day. The solvent of the reaction mixture was distilled off under vacuum, diluted with 200 ml of ethyl acetate and successively washed with water (100 ml), saturated potassium hydrogen sulfate solution (100 ml), saturated aqueous sodium hydrogen carbonate (100 ml) and saturated saline (100 ml). Then, after drying over sodium sulfate, the solvent was distilled off under vacuum. The residue was purified by a silica gel column chromatography (hexane/ethyl acetate=1/2) to obtain 7.67 g (95%) of the above-identified compound as a colorless crystal.

IR(KBr)cm$^{-1}$: 3070, 2932, 1691, 1736, 1648, 1485, 1414, 1206, 1110, 703. MS(FAB) 555[M+1]$^+$. $^1$H-NMR(CDCl$_3$): δ 1.07(9H, s) 1.39(3H, t, J=7.1 Hz) 1.59–1.77(4H, m) 1.93–2.04(4H, m) 3.70–3.78(1H, m) 4.38(2H, q, J=7.1 Hz) 5.44–5.51(1H, m) 7.35–7.47(6H, m) 7.68–7.73(5H, m) 8.71 (1H, dd, J=1.9 and 4.5 Hz) 8.56(1H, s) 8.77(1H, dd, J=1.9 and 7.9 Hz).

Example 111

Synthesis of 1-[trans-4-(t-butyldiphenylsilyloxy) cyclohexyl]-1,4-dihydro[1,8]naphthylidin-4-one-3-carboxylic acid The same reaction was carried out as in Example 3, except for using ethyl 1-[trans-4-(t-butyldiphenylsilyloxy) cyclohexyl]-1,4-dihydro[1,8]naphtylidin-4-one-3-carboxylate, instead of (±)-1-(1-methoxycarbonylpyrrolidin-3-yl)-1,4-dihydro[1,8] naphtyridin-4-one-3-carboxylate, to obtain 1.71 g (90%) of the above-identified compound as a colorless crystal.

IR(KBr)cm$^{-1}$: 2936, 1729, 1612, 1472, 1071, 790. MS(FAB) 527[M+1]$^+$. $^1$H-NMR(CDCl$_3$): δ 1.08(9H, s) 1.64–1.77(4H, m) 1.95–2.06(4H, m) 3.70–3.76(1H, m) 5.59–5.64(1H, m) 7.37–7.48(6H, m) 7.54(1H, dd, J=4.5 and 7.9 Hz) 7.68–7.71(4H, m) 8.82(1H, dd, J=1.9 and 7.9 Hz) 8.84(1H, s) 8.88(1H, dd, J=1.9 and 4.5 Hz) 14.45(1H, brs).

Example 112

Synthesis of N-(4-pyridyl)-1-[trans-4-(t-butyldiphenylsilyloxy)cyclohexyl]-1,4-dihydro[1,8] naphthylidin-4-one-3-carboxamide The same reaction was carried out as in Example 4, except for using 1-[trans-4-(t-butyldiphenylsilyloxy)cyclohexyl-1,4-dihydro[1,8]naphtyridin-4-one-3-carboxylic acid and 4-aminopyridine, instead of (±)-1-(1-methoxycarbonylpyrrolidin-3-yl)-1,4-dihydro[1,8] naphtyridin-4-one-3-carboxylic acid and 2,6-dichloroaniline, respectively to obtain 90 mg (79%) of the above-identified compound as a slightly yellow crystal.

IR(KBr)cm$^{-1}$: 3069, 2932, 1688, 1615, 1527, 1488, 1414, 1110. MS(FAB) 603[M+1]$^+$. $^1$H-NMR(CDCl$_3$): δ 1.09(9H, s) 1.68–1.79(4H, m) 1.97–2.04(4H, m) 3.74–3.77(1H, m) 5.59–5.64(1H, m) 7.39–7.53(7H, m) 7.64–7.71(6H, m) 8.50–8.53(2H, m) 8.81–8.84(2H, m) 8.95(1H, s) 12.28(1H, brs).

Example 113

Synthesis of N-(4-pyridyl)-1-(trans-4-hydroxycyclohexyl)-1,4-dihydro[1,8]naphthylidin-4-one-3-carboxamide To a 15 ml tetrahydrofuran solution of 416 mg (0.68 mmol) of N-(4-pyridyl)-1-[trans-4-(t-butyldiphenylsilyloxy) cyclohexyl]-1,4-dihydro[1,8]naphthylidin-4-one-3-carboxamide, 1.02 ml (1.02 mmol) of a 1M tetrabutylammonium fluoride/tetrahydrofuran solution was added at room temperature and stirred for 4 hours. The solvent was distilled off under vacuum from the reaction mixture and the residue was purified by a silica gel column chromatography (methylene chloride/methanol=10/1), to obtain 220 mg (89%) of the above-identified compound as a slightly yellow crystal.

IR(KBr)cm$^{-1}$: 13450, 3220, 2928, 1692, 1608, 1532, 1189, 1411, 1196, 1080. MS(FAB) 365[M+1]$^+$. $^1$H-NMR (CDCl$_3$): δ 1.6–1.77(2H, m) 1.91–2.01(2H, m) 2.12–2.26 (4H, m) 3.80–3.88 (1H, m) 5.62–5.69(1H, m) 7.51–7.55(1H, m) 7.67–7.70(2H, m) 8.52–8.55(2H, m) 8.84–8.87(2H, m) 9.08(1H, s) 12.31(1H, brs).

Example 114

Synthesis of cis-4-{3-[(4-pyridylamino)carbonyl]-4-oxo[1,8]naphthylidin-1(4H)-yl}cyclohexylacetate To a 6 ml tetrahydrofuran solution of 100 mg (0.27 mmol) of N-(4-pyridyl)-1-(trans-4-hydroxycyclohexyl)-1,4-dihydro[1,8]naphthylidin-4-one-3-carboxamide, 79 mg (0.30 mmol) of triphenyl phosphine and 47 μl (0.82 mmol) of acetic acid were added at 0° C. and stirred at room temperature for 3 hours.

Further, 79 mg (0.30 mmol) of triphenyl phosphine and 47 μl (0.82 mmol) of acetic acid and stirred at room temperature overnight. Further, 79 mg (0.30 mmol) of triphenyl phosphine and, 47 μl (0.82 mmol) of acetic acid were added and stirred at room temperature for 2 hours, at 50° C. for 3 hours, and at 65° C. overnight. Further, 79 mg (0.30 mmol) of triphenyl phosphine and 47 μl (0.82 mmol) of acetic acid were added and stirred at 65° C. all day. The reaction mixture was diluted with ethyl acetate (30 ml), washed with an aqueous saturated sodium hydrogen carbonate solution (20 ml) and water (20 ml) in this order. After drying over anhydrous sodium sulfate, the solvent was distilled off under vacuum from the reaction mixture and the residue was purified by a silica gel column chromatography (ethyl acetate/methanol=10/1), to obtain 64 mg (57%) of the above-identified compound as a colorless crystal.

IR(KBr)cm$^{-1}$: 2952, 1736, 1691, 1605, 1529, 1489, 1414, 1228, 785. MS(FAB) 407[M+1]$^+$. $^1$H-NMR(CDCl$_3$): δ 1.85–2.21(8 H, m) 2.17(3H, s) 5.17–5.19(1H, m) 5.60–5.74 (1H, m) 7.51–7.56(1H, m) 7.68–7.71(2H, m) 8.53–8.55(2H, m) 8.84–8.89(2H, m) 9.16(1H, s) 12.37(1H, brs).

Example 115

Synthesis of N-(4-pyridyl)-1-(cis-4-hydroxycyclohexyl)-1,4-dihydro[1,8]naphthylidin-4-one-3-carboxamide The same reaction was carried out as in Example 3, except for using cis-4-{3-[(4-pyridylamino)carbonyl]-4-oxo[1,8] naphtyridin-1(4H)-yl}cyclohexylacetate, instead of (±)-1-(1-methoxycarbonylpyrrolidin-3-yl)-1,4-dihydro[1,8] naphtyridin-4-one-3-carboxylate, to obtain 9 mg (18%) of the above-identified compound as a colorless crystal.

IR(KBr)cm$^{-1}$: 3216, 2942, 1684, 1614, 1531, 1491, 1412, 1293, 1194, 790. MS(FAB) 365[M+1]$^+$. $^1$H-NMR(CDCl$_3$): δ 1.86–1.90(4H, m) 2.05–2.39(4H, m) 4.21–4.26(1H, m) 5.61–5.70(1 H, m) 7.52(1H, dd, J=4.5 and 7.9 Hz) 7.68–7.71 (2H, m) 8.52–8.54(2H, m) 8.84–8.88(2H, m) 9.21(1H, s) 12.34(1H, brs).

Example 116

Synthesis of N-(3,5-dichloropyridin-4-yl)-1-[trans-4-(t-butyldiphenylsilyloxy)cyclohexyl]-1,4-dihydro [1,8]naphthylidin-4-one-3-carboxamide The same reaction was carried out as in Example 10, except for using 1-[trans-4-(t-butyldiphenylsilyloxy) cyclohexyl]-1,4-dihydro[1,8]naphtyridin-4-one-3-carboxylic acid, instead of (S)-1-(1-benzyloxycarbonylpyrrolidin-3-yl)-1,4-dihydro[1,8] naphtyridin-4-one-3-carboxylic acid, to obtain 366 mg (96%) of the above-identified compound as a slightly yellow crystal.

IR(KBr)cm$^{-1}$: 3070, 2932, 1689, 1615, 1540, 1486, 1413, 1109, 703. MS(FAB) 671[M+1]$^+$. $^1$H-NMR(CDCl$_3$): δ 1.08 (9H, s) 1.69–1.81(4H, m) 1.99–2.06(4H, m) 3.72–3.77(1H, m) 5.58–5.64(1H, m) 7.37–7.47(6H, m) 7.50(1H, dd, J=4.5 and 7.8 Hz) 7.68–7.71(4H, m) 8.54(2H, s) 8.82–8.88(2H, m) 8.94(1H, s) 12.14(1H, brs).

Example 117

Synthesis of N-(3,5-dichloropyridin-4-yl)-1-(trans-4-hydroxycyclohexyl)-1,4-dihydro[1,8]naphthylidin-4-one-3-carboxamide The same reaction was carried out as in Example 113, except for using N-(3,5-dichloropyridin-4-yl)-1-[trans-4-(t-butyldiphenylsilyloxy)cyclohexyl]-1,4-dihydro[1,8]naphtyridin-4-one-3-carboxamide, instead of N-(4-pyridyl)-1-[trans-4-(t-butyldiphenylsilyloxy)cyclohexyl]-1,4-dihydro[1,8]naphtyridin-4-one-3-carboxamide, to obtain 3.06 g (89%) of the above-identified compound as a slightly yellcow crystal.

IR(KBr)cm$^{-1}$: 3376, 2941, 1688, 1615, 1541, 1490, 1414, 1193, 1075, 791. MS(FAB) 433[M+1]$^+$. $^1$H-NMR(CDCl$_3$): δ 1.62–1.73(2H, m) 1.90–2.01(2H, m) 2.11–2.23(2H, m) 2.21–2.25(2 H, m) 3.80–3.83(1H, m) 5.65–5.71(1H, m) 7.53(1H, dd, J=4.5 and 7.9 Hz) 8.56(2H, s) 8.86(1H, dd, J=1.9 and 4.5 Hz) 8.89(1H, dd, J=1.9 and 7.9 Hz) 9.07(1H, s) 12.17(1H, brs).

Example 118

Synthesis of cis-4-[3-{[(3,5-dichloro-4-pyridinyl)amino]carbonyl}-4-oxo[1,8]naphthylidin-1(4H)-yl[cyclohexylacetate The same reaction was carried out as in Example 114, except for using N-(3,5-dichloropyridin-4-yl)-1-(trans-4-hydroxycyclohexyl)-1,4-dihydro[1,8]naphthylidin-4-one-3-carboxamide, instead of N-(4-pyridyl)-1-(trans-4-hydroxycyclohexyl)-1,4-dihydro[1,8]naphthylidin-4-one-3-carboxamide, to obtain 71 mg (65%) of the above-identified compound as a colorless crystal.

IR(KBr)cm$^-$: 2954, 1726, 1684, 1615, 1539, 1488, 1417, 1226, 797. MS(FAB) 475[M+1]$^+$. $^1$H-NMR(CDCl$_3$): δ 1.83–1.99(4 H, m) 2.12–2.21(4H, m) 2.15(3H, s) 5.15–5.17 (1H, m) 5.65–5.72(1H, m) 7.53(1H, dd, J=4.5 and 8.0 Hz) 8.57(2H, s) 8.85(1H, dd, J=1.9 and 4.5 Hz) 8.90(1H, dd, J=1.9 and 8.0 Hz) 9.16(1H, s) 12.21(1H, brs).

Example 119

Synthesis of N-(3,5-dichloropyridin-4-yl)-1-(cis-4-hydroxycyclohexyl)-1,4-dihydro[1,8]naphthylidin-4-one-3-carboxamide The same reaction was carried out as in Example 3, except for using cis-4-[3-{[(3,5-dichloro-4-pyridinyl)amino]carbonyl}-4-oxo[1,8]naphyridin-1(4H)-yl]cyclohexylacetate, instead of (±)-1-(1-methoxycarbonylpyrrolidin-3-yl)-1,4-dihydro[1,8]naphtyridin-4-one-3-carboxylate, to obtain 46 mg (84%) of the above-identified compound as a colorless crystal.

IR(KBr)cm$^{-1}$: 3562, 2939, 1684, 1612, 1540, 1487, 1412, 1187, 9721. MS(FAB) 433[M+1]$^+$. $^1$H-NMR(CDCl$_3$): δ 1.86–1.90 (4H, m) 2.04–2.08(2H, m) 2.28–2.38(2H, m) 4.21–4.22(1H, m) 5.61–5.68(1H, m) 7.52(1H, dd, J=4.5 and 8.0 Hz) 8.56(2H, s) 8.85(1H, dd, J=2.0 and 4.5 Hz) 8.90(1H, dd, J=2.0 and 8.0 Hz) 9.20(1H, s) 12.21(1H, brs).

Example 120

Synthesis of N-(3,5-dichloropyridin-4-yl)-1-(4-oxocyclohexyl)-1,4-dihydro[1,8]naphthylidin-4-one-3-carboxamide To a 50 ml methylene chloride solution of 1.39 g (6.46 mmol) of pyridinium chlorochromate and 530 mg (6.46 mmol) of sodium acetate, a 50 ml methylene chloride solution of N-(3,5-dichloropyridin-4-yl)-1-(trans-4-hydroxycyclohexyl)-1,4-dihydro[1,8]naphthyridin-4-one-3-carboxamide was added at room temperature and was stirred for 1 hour. Further, 348 mg (1.62 mmol) of pyridinium chlorochromate and 133 mg (1.62 mmol) of sodium acetate were added and stirred at room temperature for 30 minutes, followed by diluting with diethyl ether. Then, after filtration, the mother liquor was concentrated. The residue was purified by a silica gel chromatography (hexane/ethyl acetate= 1/4) to obtain 630 mg (90%) of the above-identified compound as a slightly yellow crystal.

IR(KBr)cm$^{-1}$: 2932, 1688, 1618, 1540, 1485, 1414, 1348, 786. MS(FAB) 431[M+1]$^+$. $^1$H-NMR(CDCl$_3$): δ 2.35–2.43 (4H, m) 2.68–2.73(4H, m) 6.04–6.11(1H, m) 7.56(1H, dd, J=4.5 and 8.0 Hz) 8.56(2H, s) 8.88(1H, dd, J=1.9 and 4.5 Hz) 8.92(1H, dd, J=1.9 and 8.0 Hz) 9.07(1H, s) 12.07(1H, brs).

Example 121

Synthesis of N-(3-chloropyridin-4-yl)-1-{trans-4-(t-butyldiphenylsilyloxy)cyclohexyl}-1,4-dihydro[1,8]naphthylidin-4-one-3-carboxamide The same reaction was carried out as in Example 4, except for using 1-{trans-4-(t-butyldiphenylsilyloxy)cyclohexyl}-1,4-dihydro[1,8]naphthyridin-4-one-3-carboxylic acid and 4-amino-3-chloropyridine, instead of (±)-1-(1-methoxycarbonylpyrrolidin-3-yl)-1,4-dihydro[1,8]naphtyridin-4-one-3-carboxylic acid and 2,6-dichloroaniline, respectively, to obtain 1.05 g (87%) of the above-identified compound as a colorless crystal.

IR(KBr)cm$^{-1}$: 2933, 1684, 1617, 1580, 1488, 1412, 1111, 701. MS(FAB) 637[M+1]$^+$. $^1$H-NMR(CDCl$_3$): δ 1.99(9H, s) 1.68–1.81(4H, m) 1.97–2.07(4H, m) 3.71–3.79(1H, m) 5.58–5.68(1H, m) 7.38–7.48(6H, m) 7.50(1H, dd, J=4.5 and 7.9 Hz) 7.69–7.72(4H, m) 8.40–8.42(1H, m) 8.55–8.57(2H, m) 8.83(1H, dd, J=1.9 and 4.5 Hz) 8.89(1H, dd, J=1.9 and 7.9 Hz) 8.95(1H, s) 12.71(1H, brs).

Example 122

Synthesis of N-(3-chloropyridin-4-yl)-1-(trans-4-hydroxycyclohexyl)-1,4-dihydro[1,8]naphthylidin-4-one-3-carboxamide The same reaction was carried out as in Example 113, except for using N-(3-chloropyridin-4-yl)-1-{trans-4-(t-butyldiphenylsilyloxy)cyclohexyl}-1,4-dihydro[1,8]naphtyridin-4-one-3-carboxamide, instead of N-(4-pyridyl)-1-{trans-4-(t-butyldiphenylsilyloxy)cyclohexyl}-1,4-dihydro[1,8]naphtyridin-4-one-3-carboxamide, to obtain 570 mg (91%) of the above-identified compound as a colorless crystal.

IR(KBr)cm$^{-1}$: 3200, 2939, 1690, 1571, 1490, 1413, 1194. MS(FAB) 399[M+1]$^+$. $^1$H-NMR(DMSO-d$_6$): δ 1.40–1.51 (2H, m) 1.98–2.08(6H, m) 4.72–4.75(1H, m) 5.47–5.53(1H, m) 7.71(1H, dd, J=4.5 and 8.0 Hz) 8.47(1H, d, J=5.5 Hz) 8.57(1H, d, J=5.5 Hz) 8.65(1H, s) 8.82(1H, dd, J=1.9 and 8.0 Hz) 9.02(1H, dd, J=1.9 and 4.5 Hz) 9.09(1H, s) 12.90(1H, brs).

Example 123

Synthesis of N-(3-chloropyridin-4-yl)-1-(4-oxocyclohexyl)-1,4-dihydro[1,8]naphthylidin-4-one-3-carboxamide The same reaction was carried out as in Example 120, except for using N-(3-chloropyridin-4-yl)-1-(trans-4- hydroxycyclohexyl)-1,4-dihydro[1,8]naphtyridin-4-one-3-carboxamide, instead of N-(3,5-dichloropyridin-4-yl)-1-(trans-4-hydroxycyclohexyl)-1,4-dihydro[1,8]naphtyridin-4-one-3-carboxamide, to obtain 22 mg (11%) of the above-identified compound as a colorless crystal.

IR(KBr)cm$^{-1}$: 3532, 2956, 1728, 1558, 1490, 1418, 1306. MS(FAB) 397[M+1]$^+$. $^1$H-NMR(CDCl$_3$): δ 2.33–2.50(4H, m) 2.65–2.80(4H, m) 6.08–6.12(1H, m) 7.56(1H, dd, J=4.5 and 7.9 Hz) 8.43–8.45(1H, m) 8.57–8.59(2H, m) 8.88(1H, dd, J=1.8 and 4.5 Hz) 8.95(1H, dd, J=1.8 and 7.9 Hz) 9.08(1H, s) 12.66 (1H, brs).

Example 124

Synthesis of ethyl 1-(trans-4-methoxycyclohexyl)-1,4-dihydro[1,8]naphthylidin-4-one-3-carboxylate To a 2 ml methylene chloride solution of 50 mg (0.16 mmol) of ethyl 1-(trans-4-hydroxycyclohexyl)-1,4-dihydro[1,8]naphthylidin-4-one-3-carboxylate, 26 mg (0.17 mmol) of trimethyloxonium tetrafluoroborate at room temperature and stirred at the same temperature overnight. The reaction mixture was diluted with ethyl acetate (30 ml) and successively washed with an aqueous saturated sodium hydrogen carbonate solution (10 ml) and saturated saline (10 ml), followed by drying over anhydrous sodium sulfate. The solvent was distilled off under vacuum and the residue was purified by a silica gel column chromatography (ethyl acetate/methanol=20/1), to obtain 37 mg (71%) of the above-identified compound as a colorless crystal.

IR(KBr)cm$^{-1}$: 3074, 2963, 1720, 1626, 1485, 1417, 1208, 1095, 806. MS(FAB) 331[M+1]$^+$. $^1$H-NMR(CDCl$_3$): δ 1.43 (3H, t, J=7.1 Hz) 1.50–1.61(2H, m) 1.78–1.89(2H, m) 2.09–2.17(2H, m) 2.28–2.33(2H, m) 3.26–3.32(1H, m) 3.42 (3H, s) 4.42(2 H, q, J=7.1 Hz) 5.50–5.57(1H, m) 7.41(1H, dd, J=4.5 and 7.9 Hz) 8.70(1H, s) 8.74(1H, dd, J=1.9 and 4.5 Hz) 8.80(1H, dd, J=1.9 and 7.9 Hz).

Example 125

Synthesis of 1-(trans-4-methoxycyclohexyl)-1,4-dihydro[1,8]naphthylidin-4-one-3-carboxylic acid The same reaction was carried out as in Example 3, except for using ethyl 1-(trans-4-methoxycyclohexyl)-1,4-dihydro[1,8]naphthylidin-4-one-3-carboxylate, instead of (±)-1-(1-methoxycarbonylpyrrolidin-3-yl)-1,4-dihydro[1,8]naphtyridin-4-one-3-carboxylate, to obtain 206 mg (83%) of the above-identified compound as a colorless crystal.

IR(KBr)cm$^{-1}$: 3082, 2950, 1731, 1620, 1476, 1099, 805. MS(FAB) 303[M+1]$^+$. $^1$H-NMR(CDCl$_3$): δ 1.51–1.62(2H, m) 1.84–1.94(2H, m) 2.13–2.16(2H, m) 2.31–2.34(2H, m) 3.283.33(1 H, m) 3.42(3H, s) 5.64–5.71(1H, m) 7.57(1H, dd, J=4.5 and 8.0 Hz) 8.85(1H, dd, J=2.0 and 8.0 Hz) 8.91(1H, dd, J=2.0 and 4.5 Hz) 8.98(1H, s) 14.49(1H, brs).

Example 126

Synthesis of N-(4-pyridyl)-1-(trans-4-methoxycyclohexyl)-1,4-dihydro[1,8]naphthylidin-4-one-3-carboxamide The same reaction was carried out as in Example 4, except for using 1-(trans-4-methoxychlorohexyl)-1,4-dihydro[1,8]naphtyridin-4-one-3-carboxylic acid and 4-aminopyridine, instead of (±)-1-( 1-methoxycarbonylpyrrolidin-3-yl)-1,4-dihydro[1,8]naphtyridin-4-one-3-carboxylic acid and 2,6-dichloroaniline, respectively, to obtain 94 mg (83%) of the above-identified compound as a slightly yellow crystal.

IR(KBr)cm$^{-1}$: 3081, 2938, 1692, 1600, 1536, 1490, 1412, 1193, 1100, 826, 794. MS(FAB) 379[M+1]$^+$. $^1$H-NMR (CDCl$_3$): 1.52–1.62(2H, m) 1.87–1.97(2H, m) 2.14–2.18 (2H, m) 2.31–2.35(2H, m) 3.29–3.43(1H, m) 3.43(3H, s) 5.62–5.69(1H, m) 7.51–7.55(1H, m) 7.67–7.70(2H, m) 8.52–8.55(2H, m) 8.84–8.87(2H, m) 9.08(1H, s) 12.32(1H, brs).

Example 127

Synthesis of N-(3,5-dichloropyridin-4-yl)-1-(trans-4-methoxycyclohexyl)-1,4-dihydro[1,8] naphthylidin-4-one-3-carboxamide The same reaction was carried out as in Example 10, except for using 1-(trans-4-methoxycyclohexyl)-1,4-dihydro[1,8]naphthylidin-4-one-3-carboxylic acid, instead of (S)-1-(1-benzyloxycarbonylpyrrolidin-3-yl)-1,4-dihydro[1,8]naphthylidin-4-one-3-carboxylic acid, to obtain 116 mg (87%) of the above-identified compound as a slightly yellow crystal.

IR(KBr)cm$^{-1}$: 3050, 2944, 1680, 1619, 1487, 1408, 1098, 784. MS(FAB) 447[M+1]$^+$. $^1$H-NMR(CDCl$_3$): 1.54–1.62 (2H, m) 1.90–1.97(2H, m) 2.14–2.18(2H, m) 2.30–2.34(2H, m) 3.27–3.33(1H, m) 3.42(3H, s) 5.62–5.69(1H, m) 7.53 (1H, dd, J=4.5 and 7.8 Hz) 8.56(2H, s) 8.86(1H, dd, J=1.9 and 4.5 Hz) 8.89(1H, dd, J=1.9 and 7.8 Hz) 9.08(1H, s) 12.18(1H, brs).

Example 128

Synthesis of trans-4-[3-{[(3,5-dichloro-4-pyridinyl) amino]carbonyl}-4-oxo[1,8]naphthylidin-1(4H)-yl] cyclohexylpivalate To a 8 ml chloroform solution of 100 mg (0.23 mmol) of N-(3,5-dichloropyridin-4-yl)-1-(trans-4-hydroxycyclohexyl)-1,4-dihydro[1,8]naphthylidin-4-one-3-carboxamide, 34 μl (0.28 mmol) of pivaloyl chloride and 28 μl (0.35 mmol) of pyridine were added at room temperature and stirred at room temperature for 2 hours. Then, at room temperature, 34 μl (0.28 mmol) of pivaloyl chloride, 28 μl (0.35 mmol) of pyridine and 2 mg (0.02 mmol) of dimethyl aminopyridine were added and stirred at the same temperature for 1 hour. Further, 34 μl (0.28 mmol) of pivaloyl chloride, 28 μl (0.35 mmol) of pyridine were added and stirred at 50° C. for 2 hours. Further, 34 μl (0.28 mmol) of pivaloyl chloride and 28 μl (0.35 mmol) of pyridine were added at 60° C. for 1 hour. Further, 68 μl (0.56 mmol) of pivaloyl chloride and 56 μl (0.70 mmol) of pyridine were added and stirred at 60° C. for 2 hours and at room temperature overnight. The reaction mixture was diluted with methylene chloride (10 ml), and, after successively washing with an aqueous saturated sodium hydrogen carbonate solution (10 ml) and saturated saline (10 ml), followed by drying over anhydrous sodium sulfate, the solvent was distilled off under vacuum. The residue was purified by a silica gel column chromatography (hexane/ethyl acetate= 3/1) to obtain 118 mg (99%) of the above-identified compound as a slightly yellow crystal.

IR(KBr)cm$^{-1}$: 2960, 1716, 1694, 1616, 1558, 1486, 1175, 792. MS(FAB) 517[M+1]$^+$. $^1$H-NMR(CDCl$_3$): 1.21(9H, s) 1.69–1.79(2H, m) 2.01–2.10(2H, m) 2.15–2.20(2H, m) 2.24–2.29(2H, m) 4.79–4.84(1H, m) 5.60–5.69(1H, m) 7.53 (1H, dd, J=4.5 and 7.9 Hz) 8.56(2H, s) 8.85(1H, dd, J=1.9 and 4.5 Hz) 8.89(1H, dd, J=1.9 and 7.9 Hz) 9.08(1H, s) 12.14(1H, brs).

Example 129

Synthesis of trans-4-[3-{[(3,5-dichloro-4-pyridinyl) amino]carbonyl}-4-oxo[1,8]naphthylidin-1(4H)-yl] cyclohexylpropionate The same reaction was carried out as in Example 128, except for using propionyl chloride, instead of pivaloyl chloride, to obtain 108 mg (92%) of the above-identified compound as a slightly yellow crystal.

IR(KBr)cm$^{-1}$: 2943, 1727, 1694, 1615, 1543, 1488, 1413, 1189, 791. MS(FAB) 489[M+1]$^+$. $^1$H-NMR(CDCl$_3$): 1.16 (3H, t, J=7.6 Hz) 1.71–1.79(2H, m) 2.03–2.10(2H, m) 2.15–2.19(2H, m) 2.25–2.29(2H, m) 2.34(2H, q, J=7.6 Hz) 4.83–4.88(1H, m) 5.60–5.67(1H, m) 7.53(1H, dd, J=4.5 and 7.9 Hz) 8.56(2H, s) 8.86(1H, dd, J=1.9 and 4.5 Hz) 8.89(1H, dd, J=1.9 and 7.9 Hz) 9.07(1H, s) 12.14(1H, brs).

Example 130

Synthesis of trans-4-[3-{[(3,5-dichloro-4-pyridinyl)amino]carbonyl}-4-oxo[1,8]naphthylidin-1(4H)-yl]cyclohexylbenzoate The same reaction was carried out as in Example 128, except for using benzoyl chloride, instead of pivaloyl chloride, to obtain 130 mg (quant.) of the above-identified compound as a slightly yellow crystal.

IR(KBr)cm$^{-1}$: 2940, 1694, 1616, 1556, 1488, 1410, 1326, 1282, 1116, 791, 716. MS(FAB) 537[M+1]$^+$. $^1$H-NMR (CDCl$_3$): 1.85–1.95(2H, m) 2.08–2.18(2H, m) 2.22–2.25 (2H, m) 2.41–2.45(2H, m) 5.07–5.14(1H, m) 5.68–5.78(1H, m) 7.44–7.60(3H, m) 7.54(1H, dd, J=4.5 and 7.9 Hz) 8.05–8.11(2H, m) 8.57(2H, m) 8.87(1H, dd, J=1.9 and 4.5 Hz) 8.91(1H, dd, J=1.9 and 7.9 Hz) 9.11(1H, s) 12.16(1H, brs).

Example 131

Synthesis of trans-4-[3-{[(3,5-dichloro-4-pyridinyl)amino]carbonyl}-4-oxo[1,8]naphthylidin-1(4H)-yl]cyclohexyl 4-(chloromethyl)benzoate The same reaction was carried out as in Example 128, except for using 4-chloromethylbenzoyl chloride, instead of pivaloyl chloride, to obtain 273 mg (81%) of the above-identified compound as a slightly yellow crystal.

IR(KBr)cm$^{-1}$: 2944, 1719, 1686, 1618, 1542, 1483, 1413, 1275, 1104, 791. MS(FAB) 585[M+1]$^+$. $^1$H-NMR(CDCl$_3$): 1.84–1.94(2H, m) 2.09–2.18(2H, m) 2.21–2.26(2H, m) 2.40–2.44(2H, m) 4.63(2H, s) 5.08–5.12(1H, m) 5.68–5.75 (1H, m) 7.47–7.52(2H, m) 7.54(1H, dd, J=4.5 and 8.0 Hz) 8.04–8.09(2H, m) 8.57(2H, s) 8.87(1H, dd, J=1.9 and 4.5 Hz) 8.90(1H, dd, J=1.9 and 8.0 Hz) 9.11(1H, s) 12.14(1H, brs).

Example 132

Synthesis of trans-4-[3-{[(3,5-dichloro-4-pyridinyl)amino]carbonyl}-4-oxo[1,8]naphthylidin-1(4H)-yl]cyclohexyl 4-[(4-methylpiperazino)methylibenzoate To a 4 ml methylene chloride solution of 120 mg (0.20 mmol) of trans-4-[3-{[(3,5-dichloro-4-pyridinyl)amino]carbonyl}-4-oxo[1,8]naphthylidin-1(4H)-yl]cyclohexyl 4-(chloromethyl)benzoate, 43 μl (0.31 mmol) of triethylamine, 27 μl (0.25 mmol) of N-methyl piperazine and 3 mg (0.02 mmol) of sodium iodide were added at room temperature and stirred at 40° C. for 5 hours. Further 43 μl (0.31 mmol) of triethylamine, 27 μl (0.25 mmol) of N-methylpiperazine and 3 mg (0.02 mmol) of sodium iodide were added and stirred at 40° C. overnight. The reaction mixture was diluted with methylene chloride (30 ml), and, after successively washing with water (20 ml) and saturated saline (20 ml), followed by drying over anhydrous sodium sulfate, the solvent was distilled off under vacuum. The residue was purified by a silica gel column chromatography (methylene chloride/methanol=5/1) to obtain 74 mg (56%) of the above-identified compound as a slightly yellow crystal.

IR(KBr)cm$^{-1}$: 2944, 1686, 1612, 1542, 1484, 1413, 1274, 1098, 789. MS(FAB) 649[M+1]$^+$. $^1$H-NMR(CDCl$_3$): 1.83–1.92(2H, m) 2.08–2.17(2H, m) 2.29–2.34(2H, m) 2.38–2.43(2H, m) 2.48–2.59(8H, m) 3.49 and 3.58(total3H, s) 5.06–5.13(1H, m) 5.66–5.74(1H, m) 7.41–7.43(2H, m) 7.54(1H, dd, J=4.5 and 8.0 Hz) 7.99–8.02(2H, m) 8.57(2H, s) 8.87(1H, dd, J=1.9 and 4.5 Hz) 8.90(1H, dd, J=1.9 and 8.0 Hz) 9.11(1H, s) 12.14(1H, s).

Example 133

Synthesis of trans-4-[3-{[(3,5-dichloro-4-pyridinyl)amino]carbonyl}-4-oxo[1,8]naphthylidin-1(4H)-yl]cyclohexyl 4-[(4-methylpiperazino)methyl]benzoate dihydrochloride To a 2 ml methanol solution of 60 mg (0.09 mmol) of trans-4-[3-{[(3,5-dichloro-4-pyridinyl)amino]carbonyl}-4-oxo[1,8]naphthylidin-1(4H)-yl]cyclohexyl 4-[(4-methylpiperazino)methyl]benzoate, 69 μl (0.28 mmol) of 4N-hydrochloric acid/dioxane was added at room temperature and stirred. Diethyl ether (10 ml) was added and the precipitated crystal was recovered by filtration to obtain 63 mg (94%) of the above-identified compound as a slightly yellow crystal.

IR(KBr)cm$^-$: 3431, 2944, 1686, 1618, 1541, 1488, 1280, 796. MS(FAB) 649[M+1]$^+$. $^1$H-NMR(DMSO-d$_6$): 1.76–1.86(2H, m) 2.10–2.13(2H, m) 2.21–2.35(6H, m) 2.78 (3H, brs) 3.08–3.56 (6H, m) 5.12–5.20(1H, m) 5.59–5.68 (1H, m) 7.55–7.68(2H, m) 7.73(1H, dd, J=4.5 and 8.0 Hz) 7.98–8.01(2H, m) 8.73(2H, s) 8.82(1H, dd, J=1.8 and 8.0 Hz) 9.03(1H, dd, J=1.8 and 4.5 Hz) 9.17(1H, s) 12.18(1H, brs).

Example 134

Synthesis of trans-4-[3-{[(3,5-dichloro-4-pyridinyl)amino]carbonyl}-4-oxo[1,8]naphthylidin-1(4H)-yl]cyclohexyl 4-(morpholinomethyl)benzoate The same reaction was carried out as in Example 132, except for using morpholine, instead of N-methylpiperazine, to obtain 100 mg (77%) of the above-identified compound as a slightly yellow crystal.

IR(KBr)cm$^{-1}$: 2954, 1713, 1694, 1615, 1540, 1487, 1411, 1276, 1113, 794. MS(FAB) 636[M+1]$^+$. $^1$H-NMR(CDCl$_3$): 1.84–1.93(2H, m) 2.08–2.18(2H, m) 2.21–2.25(2H, m) 2.39–2.47(6H, m) 3.56(2H, s) 3.70–3.73(4H, m) 5.05–5.12 (1H, m) 5.65–5.73(1H, m) 7.42–7.52(2H, m) 7.54(1H, dd, J=4.5 and 8.0 Hz) 7.99–8.02(2H, m) 8.57(2H, s) 8.87(1H, dd, J=1.9 and 4.5 Hz) 8.90(1H, dd, J=1.9 and 8.0 Hz) 9.11(1H, s) 12.15(1H, brs)

Example 135

Synthesis of trans-4-[3-{[(3,5-dichloro-4-pyridinyl)amino]carbonyl}-4-oxo[1,8]naphthylidin-1(4H)-yl]cyclohexyl 4-(morpholinomethyl)benzoate hydrochloride The same reaction was carried out as in Example 133, except for using trans-4-[3-{[(3,5-dichloro-4-pyridinyl)amino]carbonyl}-4-oxo[1,8]naphthylidin-1(4H)-yl]cyclohexyl 4-(morpholinomethyl)benzoate, instead of trans-4-[3-{[(3,5-dichloro-4-pyridinyl)amino]carbonyl}-4-oxo[1,8]naphthylidin-1(4H)-yl]cyclohexyl 4-[(4- methylpiperazino)methyl]benzoate, to obtain 68 mg (80%) of the above-identified compound as a slightly yellow crystal.

IR(KBr)cm$^{-1}$: 3438, 1687, 1613, 1540, 1487, 1415, 1279, 1116. MS(FAB) 636[M+1]$^+$. $^1$H-NMR(DMSO-d$_6$): 1.75–1.85(2H, m) 2.11–2.16(2H, m) 2.23–2.43(4H, m) 3.08–3.28(4H, m) 3.68–3.75(2H, m) 3.91–3.99(2H, m) 4.44 (2H, brs) 5.12–5.20(1H, m) 5.59–5.67(1H, m) 7.71–7.75 (2H, m) 7.73(1H, dd, J=4.5 and 8.0 Hz) 8.05–8.08(2H, m) 8.73(2H, s) 8.82(1H, dd, J=1.9 and 8.0 Hz) 9.03(1H, dd, J=1.9 and 4.5 Hz) 9.17(1H, s) 12.18(1H, s).

Example 136

Synthesis of ethyl 3-cyclopropylamino-2-(2-chloronicotinoyl acrylate

The same reaction was carried out as in Example 1, except for using cyclopropylamine, instead of (±)-3-amino-1-methoxycarbonylpyrrolidine to obtain 1.40 g (90%) of the above-identified compound as a colorless crystal.

IR(KBr)cm$^{-1}$: 2986, 1691, 1615, 1544, 1390, 1320, 1253, 810, 760. MS(FAB) 295[M+1]$^+$. $^1$H-NMR(CDCl$_3$): δ 0.85–0.97(4 H, m) 0.93(3H, t, J=7.1 Hz) 2.98–3.03(1H, m) 3.97(2H, q, J=7.1 Hz) 7.23–5.26(1H, m) 7.50(1H, dd, J=1.9 and 7.5 Hz) 8.26–8.30(1H, m) 8.36(1H, dd, J=1.9 and 4.7 Hz) 11.07(1H, brs Example 137

Synthesis of ethyl 1-cyclopropyl-1,4-dihydro[1,8] naphthylidin-4-one-3-carboxylate The same reaction was carried out as in Example 2, except for using ethyl 3-cyclopropylamino-2-(2-chloronicotinoyl) acrylate, instead of (±)-ethyl 3-(1-methoxycarbonylpyrrolidin-3-ylamino)-2-(2-chloronicotinoyl)acrylate, to obtain 900 mg (75%) of the above-identified compound as a colorless crystal.

IR(KBr)cm$^{-1}$: 2996, 1728, 1628, 1480, 1428, 1354, 1268, 1219, 780. MS(FAB) 259[M+1]$^+$. $^1$H-NMR(CDCl$_3$): δ 1.05–1.09(2 H, m) 1.27–1.34(2H, m) 1.42(3H, t, J=7.1 Hz) 3.68–3.73(1H, m) 4.41(2H, q, J=7.1 Hz) 7.43(1H, dd, J=4.6 and 8.0 Hz) 8.70(1H, s) 8.77(1H, dd, J=1.9 and 8.0 Hz) 8.80(1H, dd, J=1.9 and 4.6 Hz).

Example 138

Synthesis of 1-cyclopropyl-1,4-dihydro[1,8] naphthylidin-4-one-3-carboxylic acid The same reaction was carried out as in Example 3, except for using ethyl 1-cyclopropyl-1,4-dihydro[1,8]naphthyridin-4-one-3-carboxylate, instead of (±)-1-(1-methoxycarbonylpyrrolidin-3-yl)-1,4-dihydro[1,8] naphtyridin-4-one-3-carboxylate, to obtain 630 mg (83%) of the above-identified compound as a colorless crystal.

IR(KBr)cm$^{-1}$: 3078, 1732, 1615, 1518, 1472, 1404, 1327, 964, 803. MS(FAB) 231[M+1]$^+$. $^1$H-NMR(CDCl$_3$): δ 1.11–1.16(2 H, m) 1.34–1.40(2H, m) 3.83–3.90(1H, m) 7.58(1H, dd, J=4.5 and 8.0 Hz) 8.82(1H, dd, J=1.8 and 8.0 Hz) 8.96(1H, dd, J=1.8 and 4.5 Hz) 8.99(1H, s) 14.37(1H, s).

Example 139

Synthesis of N-(4-pyridyl)-1-cyclopropyl-1,4-dihydro[1,8]naphthylidin-4-one-3-carboxamide The same reaction was carried out as in Example 4, except for using 1-cyclopropyl-1,4-dihydro[1,8]naphtyridin-4-one- 3-carboxylic acid and 4-aminopyridine, instead of (±)-1-(1-methoxycarbonylpyrrolidin-3-yl)-1,4-dihydro[1,8] naphtyridin-4-one-3-carboxylic acid and 2,6-dichloroaniline, respectively, to obtain 166 mg (83%) of the above-identified compound as a slightly yellow crystal.

IR(KBr)cm$^{-}$: 3016, 1686, 1618, 1591, 1530, 1484, 1431, 1328, 1195, 791. MS(FAB) 307[M$^+$1]$^+$. $^1$H-NMR(CDCl$_3$): δ 1.13–1.17(2H, m) 1.34–1.38(2H, m) 3.83–3.88(1H, m) 7.55 (1H, dd, J=4.5 and 8.0 Hz) 7.67–7.69(2H, m) 8.52–8.55(2H, m) 8.82 (1H, dd, J=1.8 and 8.0 Hz) 8.92(1H, dd, J=1.8 and 4.5 Hz) 9.08(1H, s) 12.24(1H, brs).

Example 140

Synthesis of N-(3,5-dichloropyridin-4-yl)-1-cyclopropyl-1,4-dihydro[1,8]naphthylidin-4-one-3-carboxamide The same reaction was carried out as in Example 10, except for using 1-cyclopropyl-1,4-dihydro[1,8] naphtyridin-4-one-3-carboxylic acid, instead of (S)-1-(1-benzyloxycarbonylpyrrolidin-3-yl)-1,4-dihydro[1,8] naphtyridin-4-one-3-carboxylic acid, to obtain 200 mg (82%) of the above-identified compound as a slightly yellow crystal.

IR(KBr)cm$^{-1}$: 3070, 1684, 1623, 1541, 1481, 1429, 1336, 1239, 793. MS(FAB) 375[M+1]$^+$. $^1$H-NMR(CDCl$_3$): δ 1.14–1.17(2 H, m) 1.33–1.39(2H, m) 3.82–3.87(1H, m) 7.54(1H, dd, J=4.5 and 7.9 Hz) 8.56(2H, s) 8.85(1H, dd, J=1.9 and 7.9 Hz) 8.92(1H, dd, J=1.9 and 4.5 Hz) 9.08(1H, s) 12.08(1H, brs).

Example 141

Synthesis of ethyl 3-cyclobutylamino-2-(2-chloronicotinoyl)acrylate

The same reaction was carried out as in Example 1, except for using aminocyclobutane, instead of (±)-3-amino-1-methoxycarbonylpyrrolidine, to obtain 1.43 g (88%) of the above-identified compound as a slightly yellow crystal.

IR(KBr)cm$^{-1}$: 3216, 2985, 1682, 1626, 1548, 1388, 1321, 1271, 1218, 836. MS(FAB) 309[M+1]$^+$. $^1$H-NMR(CDCl$_3$): δ 0.78 and 0.92(total3H, t, J=7.1 Hz) 1.76–1.87(2H, m) 2.16–2.27(2 H, m) 2.41–2.49(2H, m) 3.91 and 3.96(total2H, q, J=7.1 Hz) 4.02–4.09(1H, m) 7.22–7.27(1H, m) 7.52 and 7.56(total1H, dd, J=1.9 and 7.5 Hz) 8.14 and 8.24(total1H, d, J=14.4 Hz) 8.37(1H, dd, J=1.9 and 4.8 Hz) 11.21(1H, brs).

Example 142

Synthesis of ethyl 1-cyclobutyl-1,4-dihydro[1,8] naphthylidin-4-one-3-carboxylate The same reaction was carried out as in Example 2, except for using ethyl 3-cyclobutylamino-2-(2-chloronicotinoyl) acrylate, instead of (±)-ethyl 3-(1-methoxycarbonylpyrrolidin-3-ylamino)-2-(2-chloronicotinoyl)acrylate, to obtain 1.17 g (95%) of the above-identified compound as a slightly yellow crystal.

IR(KBr)cm$^{-1}$: 2987, 1695, 1636, 1486, 1433, 1345, 1211, 788. MS(FAB) 273[M+1]$^+$. $^1$H-NMR(CDCl$_3$): δ 1.43(3H, t, J=7.1 Hz) 1.94–1.20(2H, m) 2.38–2.44(2H, m) 2.60–2.69 (2H, m) 4.42(2H, q, J=7.1 Hz) 5.52–5.58(1H, m) 7.39(1H, dd, J=4.5 and 7.9 Hz) 8.72(1H, dd, J=1.9 and 4.5 Hz) 8.78(1H, dd, J=1.9 and 7.9 Hz) 8.81 (1H, s).

Example 143

Synthesis of 1-cyclobutyl-1,4-dihydro[1,8] naphthylidin-4-one-3-carboxylic acid

The same reaction was carried out as in Example 3, except for using ethyl 1-cyclobutyl-1,4-dihydro[1,8]naphthylidin-4- one-3-carboxylate, instead of (±)-1-(1-methoxycarbonylpyrrolidin-3-yl)-1,4-dihydro[1,8]naphtyridin-4-one-3-carboxylate, to obtain 944 mg (93%) of the above-identified compound as a slightly yellow crystal.

IR(KBr)cm$^{-1}$: 3069, 1733, 1615, 1482, 1409, 1318, 1216, 935, 798. MS(FAB) 245[M+1]$^+$. $^1$H-NMR(CDCl$_3$): δ 1.98–2.05(2 H, m) 2.43–2.51(2H, m) 2.65–2.73(2H, m) 5.63–5.69(1H, m) 7.55(1H, dd, J=4.5 and 8.0 Hz) 8.83(1H, dd, J=1.9 and 8.0 Hz) 8.88(1H, dd, J=1.9 and 4.5 Hz) 9.07(1H, s) 14.51(1H, s).

Example 144

Synthesis of N-(4-pyridyl)-1-cyclobutyl-1,4-dihydro[1,8]naphthylidin-4-one-3-carboxamide The same reaction was carried out as in Example 4, except for using 1-cyclobutyl-1,4-dihydro[1,8]naphtyridin-4-one-3-carboxylic acid and 4-aminopyridine, instead of (±)-1-(1-methoxycarbonylpyrrolidin-3-yl)-1,4-dihydro[1,8]naphtyridin-4-one-3-carboxylic acid and 2,6-dichloroaniline, respectively, to obtain 150 mg (76%) of the above-identified compound as a slightly yellow crystal.

IR(KBr)cm$^{-1}$: 2979, 1686, 1590, 1525, 1485, 1406, 1318, 1199, 788. MS(FAB) 321[M+1]$^+$. $^1$H-NMR(CDCl$_3$): δ 1.98–2.05(2 H, m) 2.46–2.52(2H, m) 2.66–2.74(2H, m) 5.64–5.70(1H, m) 7.52(1H, dd, J=4.7 and 7.7 Hz) 7.68–7.71 (2H, m) 8.52–8.55(2H, m) 8.81–8.85(2H, m) 9.19(1H, s) 12.34(1H, brs).

Example 145

Synthesis of N-(3,5-dichloropyridin-4-yl)-1-cyclobutyl-1,4-dihydro[1,8]naphthylidin-4-one-3-carboxamide The same reaction was carried out as in Example 10, except for using 1-cyclobutyl-1,4-dihydro[1,8]naphtyridin-4-one-3-carboxylic acid, instead of (S)-1-(1-benzyloxycarbonylpyrrolidin-3-yl)-1,4-dihydro[1,8]naphtyridin-4-one-3-carboxylic acid, to obtain 73 mg (29%) of the above-identified compound as a slightly yellow crystal.

IR(KBr)cm$^{-1}$: 2952, 1686, 1618, 1541, 1483, 1407, 1340, 1231, 786. MS(FAB) 389[M+1]$^+$. $^1$H-NMR(CDCl$_3$): δ 1.97–2.05(2 H, m) 2.46–2.52(2H, m) 2.66–2.70(2H, m) 5.61–5.68(1H, m) 7.52(1H, dd, J=4.5 and 7.9 Hz) 8.57(2H, s) 8.84(1H, dd, J=1.9 and 4.5 Hz) 8.87(1H, dd, J=1.9 and 7.99 Hz) 9.19(1H, s) 12.19(1H, brs).

Example 146

Synthesis of ethyl 3-cyclopentylamino-2-(2-chloronicotinoyl)acrylate

The same reaction was carried out as in Example 1, except for using cyclopentylamine, instead of (±)-3-amino-1-methoxycarbonylpyrrolidine, to obtain 1.58 g (93%) of the above-identified compound as a slightly yellow crystal.

IR(KBr)cm$^{-1}$: 3159, 2970, 1680, 1629, 1550, 1388, 1322, 1254, 846. MS(FAB) 323[M+1]$^+$. $^1$H-NMR(CDCl$_3$): δ 0.78 and 0.92(total3H, t, J=7.1 Hz) 1.68–1.88(6H, m) 2.04–2.15 (2H, m) 3.87–3.99(1H, m) 3.90 and 3.96(total2H, q, J=7.1 Hz) 7.22–7.27(1H, m) 7.52 and 7.56(total1H, dd, J=1.8 and 7.3 Hz) 8.21 and 8.37(total1H, d, J=14.2 Hz) 8.37(1H, dd, J=1.8 and 4.8 Hz) 9.68 and 11.13(total1H, brs).

Example 147

Synthesis of ethyl 1-cyclopentyl-1,4-dihydro[1,8]naphthylidin-4-one-3-carboxylate The same reaction was carried out as in Example 2, except for using ethyl 3-cyclopentylamino-2-(2-chloronicotinoyl) acrylate, instead of (±)-ethyl 3-(1-methoxycarbonylpyrrolidin-3-ylamino)-2-(2-chloronicotinoyl)acrylate, to obtain 1.19 g (87%) of the above-identified compound as a slightly yellow crystal.

IR(KBr)cm$^{-1}$: 2947, 1695, 1640, 1607, 1415, 1348, 1223, 1145, 787. MS(FAB) 287[M+1]$^+$. $^1$H-NMR(CDCl$_3$): δ 1.43 (3H, t, J=7.1 Hz) 1.82–1.92(4H, m) 1.95–1.99(2H, m) 2.27–2.32(2H, m) 4.42(2H, q, J=7.1 Hz) 5.86–5.99(1H, m) 7.40 (1H, dd, J=4.5 and 7.9 Hz) 8.73(1H, dd, J=1.9 and 4.5 Hz) 8.75(1H, s) 8.80(1H, dd, J=1.9 and 7.9 Hz).

Example 148

Synthesis of 1-cyclopentyl-1,4-dihydro[1,8]naphthylidin-4-one-3-carboxylic acid

The same reaction was carried out as in Example 3, except for using ethyl 1-cyclopentyl-1,4-dihydro[1,8]naphtyridin-4-one-3-carboxylate, instead of (±)-1-(1-methoxycarbonylpyrrolidin-3-yl)-1,4-dihydro[1,8]naphtyridin-4-one-3-carboxylate, to obtain 895 mg (88%) of the above-identified compound as a slightly yellow crystal.

IR(KBr)cm$^{-1}$: 2960, 1729, 1621, 1472, 1406, 1222, 921, 793. MS(FAB) 259[M+1]$^+$. $^1$H-NMR(CDCl$_3$): δ 1.85–1.92 (4H, m) 2.00–2.03(2H, m) 2.33–2.38(2H, m) 5.87–6.03(1H, m) 7.56(1H, dd, J=4.5 and 8.0 Hz) 8.85(1H, dd, J=1.9 and 8.0 Hz) 8.90(1H, dd, J=1.9 and 4.5 Hz) 9.02(1H, s) 14.54 (1H, s).

Example 149

Synthesis of N-(4-pyridyl)-1-cyclopentyl-1,4-dihydro[1,8]naphthylidin-4-one-3-carboxamide The same reaction was carried out as in Example 4, except for using 1-cyclopentyl-1,4-dihydro[1,8]naphtyridin-4-one-3-carboxylic acid and 4-aminopyridine, instead of (±)-1-(1-methoxycarbonylpyrrolidin-3-yl)-1,4-dihydro[1,8]naphtyridin-4-one-3-carboxylic acid and 2,6-dichloroaniline, respectively, to obtain 190 mg (98%) of the above-identified compound as a slightly yellow crystal.

IR(KBr)cm$^{-1}$: 3230, 1684, 1614, 1571, 1526, 1484, 1410, 1338, 1198, 788. MS(FAB) 335[M+1]$^+$. $^1$H-NMR(CDCl$_3$): δ 1.87–1.96(4H, m) 2.00–2.05(2H, m) 2.33–2.40(2H, m) 5.99–6.04(1 H, m) 7.50–7.54(1H, m) 7.68–7.71(2H, m) 8.52–8.54(2H, m) 8.84–8.87(2H, m) 9.14(1H, s) 12.35(1H, brs).

Example 150

Synthesis of N-(3,5-dichloropyridin-4-yl)-1-cyclopentyl-1,4-dihydro[1,8]naphthylidin-4-one-3-carboxamide The same reaction was carried out as in Example 10, except for using 1-cyclopentyl-1,4-dihydro[1,8]naphtyridin-4-one-3-carboxylic acid, instead of (S)-1-(1-benzyloxycarbonylpyrrolidin-3-yl)-1,4-dihydro[1,8]naphtyridin-4-one-3-carboxylic acid, to obtain 78 mg (33%) of the above-identified compound as a slightly yellow crystal.

IR(KBr)cm$^{-1}$: 2947, 1686, 1618, 1542, 1484, 1412, 1218, 791. MS(FAB) 403[M+1]$^+$. $^1$H-NMR(CDCl$_3$): δ 1.84–1.89 (2H, m) 1.92–2.02(4H, m) 2.32–2.38(2H, m) 5.96–6.02(1H, m) 7.52(1H, dd, J=4.5 and 8.0 Hz) 8.56(2H, s) 8.85(1H, dd, J=1.9 and 4.5 Hz) 8.89(1H, dd, J=1.9 and 8.0 Hz) 9.13(1H, s) 12.19(1H, brs).

Example 151

Synthesis of ethyl 3-cyclohexylamino-2-(2-chloronicotinoyl)acrylate

The same reaction was carried out as in Example 1, except for using cyclohexylamine, instead of (±)-3-amino-1- methoxycarbonylpyrrolidine, to obtain 1.55 g (87%) of the above-identified compound as a colorless crystal.

IR(KBr)cm$^{-1}$: 3217, 2934, 1690, 1618, 1552, 1391, 1316, 1268, 1127, 815. MS(FAB) 337]M+1]$^+$. $^1$H-NMR(CDCl$_3$): δ 0.78 and 0.92(total3H, t, J=7.1 Hz) 1.22–1.69(6H, m) 1.83–1.87(2 H, m) 2.03–2.06(2H, m) 3.32–3.42 (1H, m) 3.91 and 3.96(total2H, q, J=7.1 Hz) 7.23–7.27(1H, m) 7.53 and 7.56(total1 H, dd, J=1.9 and 7.6 Hz) 8.22 and 8.34 (total1H, d, J=14.2 Hz) 8.37(total1H, dd, J=1.9 and 4.8 Hz) 9.72 and 11.13(total1H, brs).

Example 152

Synthesis of ethyl 1-cyclohexyl-1,4-dihydro[1,8]naphthylidin-4-one-3-carboxylate The same reaction was carried out as in Example 2, except for using ethyl 3-cyclohexylamino-2-(2-chloronicotinoyl) acrylate, instead of (±)-ethyl 3-(1-methoxycarbonylpyrrolidin-3-ylamino)-2-(2-chloronicotinoyl)acrylate, to obtain 1.28 g (96%) of the above-identified compound as a slightly yellow crystal.

IR(KBr)cm$^{-1}$: 2930, 1687, 1640, 1608, 1487, 1418, 1328, 1205, 791. MS(FAB) 301[M+1]$^+$. $^1$H-NMR(CDCl$_3$): δ 1.25–1.84(6 H, m) 1.43(3H, t, J=7.1 Hz) 1.97–2.08(4H, m) 4.42(2H, q, J=7.1 Hz) 5.47–5.57(1H, m) 7.40(1H, dd, J=4.5 and 7.9 Hz) 8.73(1H, dd, J=1.9 and 4.5 Hz) 8.75(1H, s) 8.80(1H, dd, J=1.9 and 7.9 Hz).

Example 153

Synthesis of 1-cyclohexyl-1,4-dihydro]1,8]naphthylidin-4-one-3-carboxylic acid

The same reaction was carried out as in Example 3, except for using ethyl 1-cyclohexyl-1,4-dihydro[1,8]naphthyridin-4-one-3-carboxylate, instead of (±)-1-(1-methoxycarbonylpyrrolidin-3-yl)-1,4-dihydro[1,8]naphthylidin-4-one-3-carboxylate, to obtain 1.05 g (93%) of the above-identified compound as a slightly yellow crystal.

IR(KBr)cm$^{-1}$: 2932, 1716, 1623, 1475, 1412, 1302, 1214, 917, 785. MS(FAB) 272[M+1]$^+$. $^1$H-NMR(CDCl$_3$): δ 1.25–1.88(6 H, m) 2.01–2.10(4H, m) 5.62–5.69(1H, m) 7.57(1H, dd, J=4.5 and 8.0 Hz) 8.85(1H, dd, J=2.0 and 8.0 Hz) 8.90(1H, dd, J=2.0 and 4.5 Hz) 9.02(1H, s) 14.60(1H, s).

Example 154

Synthesis of N-(4-pyridyl)-1-cyclohexyl-1,4-dihydro[1,8]naphthylidin-4-one-3-carboxamide The same reaction was carried out as in Example 4, except for using 1-cyclohexyl-1,4-dihydro[1,8]naphthyridin-4-one-3-carboxylic acid and 4-aminopyridine, instead of (±)-1-(1-methoxycarbonylpyrrolidin-3-yl)-1,4-dihydro[1,8]naphtyridin-4-one-3-carboxylic acid and 2,6-dichloroaniline, respectively, to obtain 119 mg (62%) of the above-identified compound as a yellow crystal.

IR(KBr)cm$^{-1}$: 2931, 1692, 1604, 1530, 1413, 1294, 1198, 786. MS (FAB) 349[M+1]$^+$. $^1$H-NMR(CDCl$_3$): δ 1.25–1.89 (6H, m) 2.01–2.11(4H, m) 5.60–5.67(1H, m) 7.51–7.55(1H, m) 7.68–7.71(2H, m) 8.52–8.55(2H, m) 8.84–8.87(2H, m) 9.13(1H, s) 12.38(1H, brs).

Example 155

Synthesis of N-(3,5-dichloropyridin-4-yl)-1-cyclohexyl-1,4-dihydro[1,8]naphthylidin-4-one-3-carboxamide The same reaction was carried out as in Example 10, except for using 1-cyclohexyl-1,4-dihydro[1,8]naphthyridin-4-one-3-carboxylic acid, instead of (S)-1-(1-benzyloxycarbonylpyrrolidin-3-yl)-1,4-dihydro[1,8]naphtyridin-4-one-3-carboxylic acid, to obtain 76 mg (33%) of the above-identified compound as a slightly yellow crystal.

IR(KBr)cm$^{-1}$: 2860, 1693, 1618, 1544, 1489, 1411, 1188, 883, 795. MS(FAB) 416[M+1]$^+$. $^1$H-NMR(CDCl$_3$): δ 1.30–1.85(6 H, m) 1.99–2.11(4H, m) 5.62–5.67(1H, m) 7.53(1H, dd, J=4.5 and 8.0 Hz) 8.57(2H, s) 8.56(1H, dd, J=1.9 and 4.5 Hz) 8.90(1H, dd, J=1.9 and 8.0 Hz) 9.13(1H, s) 12.26(1H, brs).

Example 156

Synthesis of N-(3-pyridyl)-1-cyclopropyl-1,4-dihydro[1,8]naphthylidin-4-one-3-carboxamide The same reaction was carried out as in Example 4, except for using 1-cyclopropyl-1,4-dihydro[1,8]naphthyridin-4-one-3-carboxylic acid and 3-aminopyridine, instead of (±)-1-(1-methoxycarbonylpyrrolidine-3-yl)-1,4-dihydro[1,8]naphtyridin-4-one-3-carboxylic acid and 2,6-dichloroaniline, respectively, to obtain 71 mg (67%) of the above-identified compound as a slightly yellow crystal.

IR(KBr)cm$^{-1}$: 3060, 1669, 1615, 1548, 1483, 1428, 1343, 778. MS(FAB) 307[M+1]$^+$. $^1$H-NMR(CDCl$_3$): δ 1.13–1.17 (2H,m) 1.35–1.38(2H, m) 3.84–3.87(1H, m) 7.28–7.32(1H, m) 7.54(1H, dd, J=4.5 and 8.0 Hz) 8.27–8.30(1H, m) 8.35–8.37(1H, m) 8.83(1H, dd, J=1.9 and 8.0 Hz) 8.88–8.89 (1H, m) 8.91(1H, dd, J=1.9 and 4.5 Hz) 9.10(1H, s) 12.14 (1H, brs).

Example 157

Synthesis of N-(3-methylpyridin-4-yl)-1-cyclopropyl-1,4-dihydro[1,8]naphthylidin-4-one-3-carboxamide The same reaction was carried out as in Example 4, except for using 1-cyclopropyl-1,4-dihydro[1,8]naphthyridin-4-one-3-carboxylic acid and 4-amino-3-methylpyridine, instead of (±)-1-(1-methoxycarbonylpyrrolidin-3-yl)-1,4-dihydro[1,8]naphtyridin-4-one-3-carboxylic acid and 2,6-dichloroaniline, respectively, to obtain 100 mg (90%) of the above-identified compound as a slightly yellow crystal.

IR(KBr)cm$^{-1}$: 2972, 1681, 1608, 1571, 1530, 1486, 1429, 1335, 782. MS(FAB) 321[M+1]$^+$. $^1$H-NMR(CDCl$_3$): δ 1.14–1.17 (2H, m) 1.34–1.40(2H, m) 2.47(3H, s) 3.84–3.88 (1H, m) 7.54(1H, dd, J=4.5 and 8.0 Hz) 8.40–8.43(3H, m) 8.85(1H, dd, J=1.9 and 8.0 Hz) 8.92(1H, dd, J=1.9 and 4.5 Hz) 9.11(1H, s) 12.18(1H, brs).

Example 158

Synthesis of trans-4-[3-{[(3,5-dichloro-4-pyridinyl)amino]carbonyl}-4-oxo[1,8]naphthylidin-1(4H)-yl] cyclohexyl 4-(diethylaminomethyl)benzoate The same reaction was carried out as in Example 132, except for using diethylamine, instead of N-methylpiperazine, to obtain 88 mg (55%) of the above-identified compound as a slightly yellow crystal.

IR(KBr)cm$^{-1}$: 2967, 1690, 1615, 1540, 1486, 1273, 1098, 789. MS(FAB) 622[M+1]$^+$. $^1$H-NMR(CDCl$_3$): δ 1.04(6H, t, J=7.1 Hz) 1.88–1.91(2H, m) 2.10–2.22(4H, m) 2.40–2.43 (2H, m) 2.53(4H, t, J=7.1 Hz) 3.62(2H, s) 5.05–5.11(1H, m) 5.68–5.73(1H, m) 7.42–7.45(2H, m) 7.54(1H, dd, J=4.5 and 8.0 Hz) 7.98–8.01(2H, m) 8.57(2H, s) 8.87(1H, dd, J≦1.9 and 4.5 Hz) 8.90(1H, dd, J=1.9 and 8.0 Hz) 9.11(1H, s) 12.15(1H, brs).

Example 159

Synthesis of trans-4-[3-{[(3,5-dichloro-4-pyridinyl) amino]carbonyl}-4-oxo[1,8]naphthylidin-1(4H)-yl] cyclohexyl 4-(diethylaminomethyl)benzoate hydrochloride The same reaction was carried out as in Example 133, except for using trans-4-[3-{[(3,5-dichloro-4-pyridinyl) amino]carbonyl}-4-oxo[1,8]naphthylidin-1(4H)-yl] cyclohexyl 4-(diethylaminomethyl)benzoate, instead of trans-4-[3-{[(3,5-dichloro-4-pyridinyl)amino]carbonyl}-4-oxo[1,8]naphthylidin-1(4H)-yl]cyclohexyl 4-[(4-methylpiperazino)methyl]benzoate, to obtain 72 mg (85%) of the above-identified compound as a slightly yellow crystal.

IR(KBr)cm$^{-1}$: 2949, 2404, 1698, 1618, 1486, 1286, 1120, 800. MS(FAB) 622[M+1]$^{+}$. $^{1}$H-NMR(DMSO-d$_{6}$): δ 1.24 (6H, t, J=7.1 Hz) 1.76–1.86(2H, m) 2.11–2.15(2H, m) 2.24–2.34(4H, m) 3.05–3.11(4H, m) 3.17(2H, s) 5.12–5.21 (1H, m) 5.59–5.65(1H, m) 7.73(1H, dd, J=4.5 and 8.0 Hz) 7.74–7.77(2H, m) 8.05–8.08(2H, m) 8.72–8.74(2H, m) 8.82 (1H, dd. J=1.9 and 8.0 Hz) 9.03(1H, dd, J=1.9 and 4.5 Hz) 9.17(1H, s) 10.01(1H, brs) 12.18(1H, s).

Example 160

Synthesis of trans-4-[3-{[(3,5-dichloro-4-pyridinyl) amino]carbonyl}-4-oxo[1,8]naphthylidin-1(4H)-yl] cyclohexyl 3-(chloromethyl)benzoate The same reaction was carried out as in Example 128, except for using 3-chloromethylbenzoyl chloride, instead of pivaloyl chloride, to obtain 130 mg (19%) of the above-identified compound as a colorless crystal.

IR(neat)cm$^{-1}$: 2955, 1713, 1694, 1614, 1486, 1414, 1199, 791. MS(FAB) 585[M+1]$^{+}$. $^{1}$H-NMR(CDCl$_{3}$): δ 1.88–1.93 (2H, m) 2.09–2.18(2H, m) 2.21–2.28(2H, m) 2.39–2.44(2H, m) 4.64(2H, s) 5.09–5.15(1H, m) 5.68–5.74(1H, m) 7.45–7.49(1H, m) 7.54(1H, dd, J=4.5 and 8.0 Hz) 7.60–7.63 (1H, m) 8.00–8.03 (1H, m) 8.07(1H, s) 8.57(2H, s) 8.87(1H, dd, J=1.9 and 4.5 Hz) 8.91(1H, dd, J=1.9 and 8.0 Hz) 9.11(1H, s) 12.14(1H, brs).

Example 161

Synthesis of trans-4-[3-{[(3,5-dichloro-4-pyridinyl) amino]carbonyl}-4-oxo[1,8]naphthylidin-1(4H)-yl] cyclohexyl 3-(morpholinomethyl benzoate The same reaction was carried out as in Example 132, except for using trans-4-[3-{[(3,5-dichloro-4-pyridinyl) amino]carbonyl}-4-oxo[1,8]naphthylidin-1(4H)-yl] cyclohexyl 3-(chloromethyl)benzoate and morpholine, instead of trans-4-[3-{[(3,5-dichloro-4-pyridinyl)amino] carbonyl}-4-oxo[1,8]naphthylidin-1(4H)-yl]cyclohexyl 4-(chloromethyl)benzoate and N-methylpiperazine, respectively, to obtain 115 mg (88%) of the above-identified compound as a colorless crystal.

IR(KBr)cm$^{-1}$: 2944, 1687, 1615, 1540, 1486, 1279, 1192, 1115, 789. MS(FAB) 636[M+1]$^{+}$. $^{1}$H-NMR(CDCl$_{3}$): δ 1.88–1.95(2 H, m) 2.07–2.16(2H, m) 2.10–2.15(2H, m) 2.38–2.45(6H, m) 3.56(2H, m) 3.70–3.72(4H, m) 5.06–5.13 (1H, m) 5.68–5.75(1H, m) 7.39–7.45(1H, m) 7.54 (1H, dd, J=4.5 and 7.9 Hz) 7.53–7.58(1H, m) 7.94–7.96(1H, m) 8.00(1H, brs) 8.57(2H, s) 8.87(1H, dd, J=1.9 and 4.5 Hz) 8.91(1H, dd, J=1.9 and 7.9 Hz) 9.11(1H, s) 12.14(1H, brs).

Example 162

Synthesis of trans-4-[3-{[(3,5-dichloro-4-pyridinyl) amino]carbonyl}-4-oxo[1,8]naphthylidin-1(4H)-yl] cyclohexyl 3-(morpholinomethyl)benzoate hydrochloride The same reaction was carried out as in Example 133, except for using trans-4-[3-{[(3,5-dichloro-4-pyridinyl) amino]carbonyl}-4-oxo[1,8]naphthylidin-1(4H)-yl] cyclohexyl 3-(morpholinomethyl)benzoate, instead of trans-4-[3-{[(3,5-dichloro-4-pyridinyl)amino]carbonyl}-4-oxo[1,8]naphthylidin-1(4H)-yl]cyclohexyl 4-[(4-methylpiperazino)methyl]benzoate, to obtain 62 mg (65%) of the above-identified compound as a colorless crystal.

IR(KBr)cm$^{-1}$: 2945, 1702, 1615, 1478, 1287, 1205, 1124, 786. MS(FAB) 636[M+1]$^{+}$. $^{1}$H-NMR(DMSO-d$_{6}$): δ 1.76–1.86(2H, m) 2.09–2.12(2H, m) 2.24–2.32(4H, m) 3.09–3.15(2H, m) 3.21–3.26(2H, m) 3.76–4.05(4H, m) 4.44 (2H, brs) 5.13–5.21(1H, m) 5.59–5.66(1H, m) 7.62–7.67 (1H, m) 7.73(1H, dd, J=4.5 and 8.0 Hz) 7.93–7.96(1H, m) 8.05–8.07(1H, m) 8.24(1H, s) 8.73(2H, s) 8.82(1H, dd, J=1.8 and 8.0 Hz) 9.04(1H, dd, J=1.8 and 4.5 Hz) 9.18(1H, s) 11.23(1H, brs) 12.18(1H, s).

Example 163

Synthesis of N-cyclobutyl-1-[trans-4-(t-butyldiphenylsilyloxy)cyclohexyl]-1,4-dihydro[1,8] naphthylidin-4-one-3-carboxamide The same reaction was carried out as in Example 4, except for using 1-[trans-4-(t-butyldiphenylsilyloxy)cyclohexyl]-1,4-dihydro[1,8]naphtyridin-4-one-3-carboxylic acid and cyclobutylamine, instead of (±)-1-(1-methoxycarbonylpyrrolidin-3-yl)-1,4-dihydro[1,8] naphtyridin-4-one-3-carboxylic acid and 2,6-dichloroaniline, respectively, to obtain 106 mg (96%) of the above-identified compound as a colorless crystal.

IR(neat)cm$^{-1}$: 2937, 1668, 1602, 1538, 1488, 1110, 789. MS (FAB) 580[M+1]$^{+}$. $^{1}$H-NMR(CDCl$_{3}$): δ 1.08(9H, s) 1.66–1.81(6H, m) 1.90–2.09(6H, m) 2.37–2.42(2H, m) 3.69–3.77(1H, m) 4.50–4.59(1H, m) 5.52–5.60(1H, m) 7.37–7.47(7H, m) 7.67–7.70(4H, m) 8.76–8.79(2H, m) 8.87 (1H, s) 9.93–9.96(1H, m).

Example 164

Synthesis of N-cyclobutyl-1-(trans-4-hydroxycyclohexyl-1,4-dihydro[1,8]naphthylidin-4-one-3-carboxamide The same reaction was carried out as in Example 113, except for using N-cyclobutyl-1-[trans-4-(t-butyldiphenylsilyloxy)cyclohexyl]-1,4-dihydro[1,8] naphtyridin-4-one-3-carboxamide, instead of N-(4-pyridyl)-1-[trans-4-(t-butyldiphenylsilyloxy)cyclohexyl]-1,4-dihydro[1,8]naphtyridin-4-one-3-carboxamide, to obtain 35 mg (98%) of the above-identified compound as a colorless crystal.

IR(KBr)cm$^{-1}$: 3456, 3245, 2948, 1664, 1604, 1528, 1489, 1364, 1224, 1078, 789. MS(FAB) 342[M+1]$^{+}$. $^{1}$H-NMR (CDCl$_{3}$): δ 1.60–2.25(12H, m) 2.41–2.44(2H, m) 3.79–3.81 (1H, m) 4.57–4.60(1H, m) 5.58–5.64(1H, m) 7.44–7.48(1H, m) 8.79–8.81 (2H, m) 9.00(1H, s) 9.98–10.00(1H, m).

Example 165

Synthesis of N-(t-butyl)-1-[trans-4-(t-butyldiphenylsilyloxy)cyclohexyl]-1,4-dihydro[1,8] naphthylidin-4-one-3-carboxamide The same reaction was carried out as in Example 4, except for using 1-[trans-4-(t-butyldiphenylsilyloxy)cyclohexyl]-1, 4-dihydro[1,8]naphtyridin-4-one-3-carboxylic acid and t-butylamine, instead of (±)-1-(1-methoxycarbonylpyrrolidin-3-yl)-1,4-dihydro[1,8]naphtyridin-4-one-3-carboxylic acid and 2,6-dichloroaniline, respectively, to obtain 80 mg (72%) of the above-identified compound as a slightly yellow crystal.

IR(KBr)cm$^{-1}$: 3256, 3072, 2932, 1672, 1560, 1489, 1413, 1228, 1110, 789, 703. MS(FAB) 582[M+1]$^+$. $^1$H-NMR (CDCl$_3$): δ 1.08(9H, s) 1.46(9H, s) 1.66–1.75(4H, m) 1.91–1.99(4H, m) 3.65–3.74(1H, m) 5.52–5.60(1H, m) 7.37–7.47(7H, m) 7.67–7.70(4H, m) 8.76–8.78(2H, m) 8.89 (1H, s) 9.79(1H, brs).

Example 166

Synthesis of N-(t-butyl)-1-(trans-4-hydroxycyclohexyl)-1,4-dihydro[1,8]naphthylidin-4-one-3-carboxamide The same reaction was carried out as in Example 113, except for using N-(t-butyl)-1-[trans-4-(t-butyldiphenylsilyloxy)cyclohexyl]-1,4-dihydro[1,8]naphtyridin-4-one-3-carboxamide, instead of N-(4-pyridyl)-1-[trans-4-(t-butyldiphenylsilyloxy)cyclohexyl]-1,4-dihydro[1,8]naphtyridin-4-one-3-carboxamide, to obtain 34 mg (97%) of the above-identified compound as a slightly yellow crystal.

IR(KBr)cm$^{-1}$: 3510, 3392, 2936, 1659, 1602, 1495, 1412, 1232, 1085, 788. MS(FAB) 344[M+1]$^+$. $^1$H-NMR(CDCl$_3$): δ 1.50(9H, s) 1.65–1.70(2H, m) 1.92–1.96(2H, m) 2.04–2.10 (2H, m) 2.18–2.22(2H, m) 3.75–3.82(1H, m) 5.58–5.67(1H, m) 7.45 (1H, dd, J=5.2 and 7.2 Hz) 8.79–8.81(2H, m) 9.03(1H, s) 9.84(1H, brs).

Example 167

Synthesis of N-cyclopentyl-1-[trans-4-(t-butyldiphenylsilyloxy)cyclohexyl]-1,4-dihydro[1,8]naphthylidin-4-one-3-carboxamide The same reaction was carried out as in Example 4, except for using 1-[trans-4-(t-butyldiphenylsilyloxy)cyclohexyl]-1,4-dihydro[1,8]naphtyridin-4-one-3-carboxylic acid and cyclopentylamine, instead of (±)-1-(1-methoxycarbonylpyrrolidin-3-yl)-1,4-dihydro[1,8]naphtyridin-4-one-3-carboxylic acid and 2,6-dichloroaniline, respectively, to obtain 98 mg (87%) of the above-identified compound as a colorless crystal.

IR(KBr)cm$^{-1}$: 3247, 3070, 2940, 1667, 1542, 1489, 1413, 1227, 1110, 703. MS(FAB) 594[M+1]$^+$. $^1$H-NMR(CDCl$_3$): δ 1.08(9H, s) 1.55–1.76(10H, m) 1.93–2.04(6H, m) 3.69–3.78(1H, m) 4.35–4.42(1H, m) 5.52–5.60(1H, m) 7.37–7.47(7H, m) 7.67–7.70(4H, m) 8.75–8.78(2H, m) 8.89 (1H, s) 9.80–9.83(1H, m).

Example 168

Synthesis of N-cyclopentyl-1-(trans-4-hydroxycyclohexyl)-1,4-dihydro[1,8]naphthylidin-4-one-3-carboxamide The same reaction was carried out as in Example 113, except for using N-cyclopentyl-1-[trans-4-(t-butyldiphenylsilyloxy)cyclohexyl]-1,4-dihydro[1,8]naphtyridin-4-one-3-carboxamide, instead of N-(4-pyridyl)-1-[trans-4-(t-butyldiphenylsilyloxy)cyclohexyl]-1,4-dihydro[1,8]naphtyridin-4-one-3-carboxamide, to obtain 47 mg (98%) of the above-identified compound as a colorless crystal.

IR(KBr)cm$^{-1}$: 3236, 2952, 1668, 1605, 1539, 1489, 1412, 1068, 790. MS(FAB) 356[M+1]$^+$. $^1$H-NMR(CDCl$_3$): δ 1.59–1.71(6 H, m) 1.73–1.80(2H, m) 1.89–2.02(2H, m) 2.03–2.10(4H, m) 2.19–2.22(2H, m) 3.77–3.84(1H, m) 4.38–4.44(1H, m) 5.56–5.63(1H, m) 7.43–7.47(1H, m) 8.78–8.81(2H, m) 9.02(1H, s) 9.85–9.88(1H, m).

Example 169

Synthesis of N-cyclopropyl-1-[trans-4-(t-butyldiphenylsilyloxy)cyclohexyl]-1,4-dihydro[1,8]naphthylidin-4-one-3-carboxamide The same reaction was carried out as in Example 4, except for using 1-[trans-4-(t-butyldiphenylsilyloxy)cyclohexyl]-1,4-dihydro[1,8]naphtyridin-4-one-3-carboxylic acid and cyclopropylamine, instead of (±)-1-(1-methoxycarbonylpyrrolidin-3-yl)-1,4-dihydro[1,8]naphtyridin-4-one-3-carboxylic acid and 2,6-dichloroaniline, respectively, to obtain 93 mg (87%) of the above-identified compound as a colorless crystal.

IR(KBr)cm$^{-1}$: 3244, 3071, 2932, 1672, 1602, 1540, 1488, 1413, 1110, 703. MS(FAB) 566[M+1]$^+$. $^1$H-NMR(CDCl$_3$): δ 0.62–0.65(2H, m) 0.80–0.84(2H, m) 1.08(9H, s) 1.55–1.78 (4H, m) 1.92–2.08(4H, m) 2.93–2.98(1H, m) 3.70–3.78(1H, m) 5.52–5.59(1H, m) 7.38–7.47(7H, m) 7.68–7.71(4H, m) 8.73–8.79(2H, m) 8.89(1H, s) 9.79(1H, brs).

Example 170

Synthesis of N-cyclopropyl-1-(trans-4-hydroxycyclohexyl)-1,4-dihydro[1,8]naphthylidin-4-one-3-carboxamide The same reaction was carried out as in Example 113, except for using N-cyclopropyl-1-[trans-4-(t-butyldiphenylsilyloxy)cyclohexyl]-1,4-dihydro[1,8]naphtyridin-4-one-3-carboxamide, instead of N-(4-pyridyl)-1-[trans-4-(t-butyldiphenylsilyloxy)cyclohexyl]-1,4-dihydro[1,8]naphtyridin-4-one-3-carboxamide, to obtain 45 mg (98%) of the above-identified compound as a colorless crystal.

IR(KBr)cm$^{-1}$: 3443, 2956, 1672, 1608, 1537, 1228, 1078, 793. MS(FAB) 328[M+1]$^+$. $^1$H-NMR(CDCl$_3$): δ 0.65–0.68 (2H, m) 0.83–0.87(2H, m) 1.64–1.70(2H, m) 1.92–1.96(2H, m) 2.07–2.11(2H, m) 2.20–2.23(2H, m) 2.97–3.00(1H, m) 3.79–3.85(1 H, m) 5.58–5.65(1H, m) 7.45(1H, dd, J=4.4 and 7.9 Hz) 8.76–8.81(2H, m) 9.03(1H, s) 9.83(1H, brs).

Example 171

Synthesis of N-(3-pyridyl)-1-[trans-4-(t-butyldiphenylsilyloxy)cyclohexyl]-1,4-dihydro[1,8]naphthylidin-4-one-3-carboxamide The same reaction was carried out as in Example 4, except for using 1-[trans-4-(t-butyldiphenylsilyloxy)cyclohexyl]-1,4-dihydro[1,8]naphtyridin-4-one-3-carboxylic acid and 3-aminopyridine, instead of (±)-1-(1-methoxycarbonylpyrrolidin-3-yl)-1,4-dihydro[1,8]naphtyridin-4-one-3-carboxylic acid and 2,6-dichloroaniline, respectively, to obtain 93 mg (82%) of the above-identfied compound as a colorless crystal.

IR(neat)cm$^{-1}$: 2934, 1682, 1603, 1538, 1488, 1415, 1110, 704. MS(FAB) 603[M+1]$^+$. $^1$H-NMR(CDCl$_3$): δ 1.09(9H, m) 1.69–1.79(4H, m) 1.97–2.08(4H, m) 3.72–3.78(1H, m) 5.58–5.68 (1H, m) 7.38–7.52(8H, m) 7.68–7.71(41H, m) 8.23–8.26(1H, m) 8.33–8.35(1H, m) 8.82(1H, s) 8.83–8.85 (1H, m) 8.87–8.88(1H, m) 8.96(1H, s) 12.17(1H, brs).

Example 172

Synthesis of N-(3-pyridyl)-1-(trans-4-hydroxycyclohexyl)-1,4-dihydro[1,8]naphthylidin-4-one-3-carboxamide The same reaction was carried out as in Example 113, except for using N-(3-pyridyl)-1-[trans- 4-(t-butyldiphenylsilyloxy)cyclohexyl]-1,4-dihydro[1,8] naphtyridin-4-one-3-carboxamide, instead of N-(4-pyridyl)-1-[trans-4-(t-butyldiphenylsilyloxy)cyclohexyl]-1,4-dihydro[1,8]naphtyridin-4-one-3-carboxamide, to obtain 53 mg (98%) of the above-identified compound as a slightly yellow cryszal.

IR(KBr)cm$^{-1}$: 2934, 1687, 1605, 1538, 1491, 1422, 1080, 786. MS(FAB) 365[M+1]$^+$. $^1$H-NMR(CDCl$_3$): δ 1.63–1.74 (2H, m) 1.94–1.99(2H, m) 2.12–2.16(2H, m) 2.21–2.26(2H, m) 3.80–3.88(1H, m) 5.62–5.69(1H, m) 7.30(1H, dd, J=4.7 and 8.2 Hz) 7.53(1H, dd, J=4.7 and 7.7 Hz) 8.26–8.30(1H, m) 8.36(1H, dd, J=1.4 and 4.7 Hz) 8.85–8.91(3H, m) 9.10(1H, s) 12.21(1 H, brs).

Example 173

Synthesis of N-(3-methylpyridin-4-yl)-1-[trans-4-(t-butyldiphenylsilyloxy)cyclohexyl]-1,4-dihydro[1,8]naphthylidin-4-one-3-carboxamide The same reaction was carried out as in Example 4, except for using 1-[trans-4-(t-butyldiphenylsilyloxy)cyclohexyl]-1,4-dihydro[1,8]naphtyridin-4-one-3-carboxylic acid and 4-amino-3-methylpyridine, instead of (±)-1-(1-methoxycarbonylpyrrolidin-3-yl)-1,4-dihydro[1,8] naphtyridin-4-one-3-carboxylic acid and 2,6-dichloroaniline, respectively, to obtain 108 mg (92%) of the above-identified compound as a colorless crystal.

IR(KBr)cm$^{-1}$: 3069, 2941, 2857, 1688, 1603, 1527, 1490, 1414, 1196, 1099, 702. MS(FAB) 617[M+1]$^+$. $^1$H-NMR (CDCl$_3$): δ 1.09(9H, s) 1.70–1.79(4H, m) 1.98–2.09(4H, m) 2.46(3H, s) 3.73–3.80(1H, m) 5.58–5.68(1H, m) 7.27–7.47 (7H, m) 7.50(1H, dd, J=4.5 and 8.1 Hz) 7.69–7.72(4H, m) 8.39–8.41(2H, m) 8.83–8.88(2H, m) 8.98(1H, s) 12.21(1H, brs).

Example 174

Synthesis of N-(3-methylpyridin-4-yl)-1-(trans-4-hydroxycyclohexyl)-1,4-dihydro[1,8]naphthylidin-4-one-3-carboxamide The same reaction was carried out as in Example 113, except for using N-(3-methylpyridin-4-yl)-1-[trans-4-(t-butyldiphenylsilyloxy)cyclohexyl]-1,4-dihydro[1,8] naphtyridin-4-one-3-carboxamide, instead of N-(4-pyridyl)-1-[trans-4-(t-butyldiphenylsilyloxy)cyclohexyl]-1,4-dihydro[1,8]naphtyridin-4-one-3-carboxamide to obtain 52 mg (95%) of the above-identified compound as a colorless crystal.

IR(KBr)cm$^{-1}$: 2940, 1692, 1605, 1536, 1491, 1294, 1199, 1078, 788. MS(FAB) 379[M+1]$^+$. $^1$H-NMR(CDCl$_3$): δ 1.56–1.71 (2 H, m) 1.95–2.05(2H, m) 2.13–2.17(2H, m) 2.23–2.26(2H, m) 2.48(3H, s) 3.82–3.90(1H, m) 5.63–5.72 (1H, m) 7.53(1H, dd, J=4.5 and 8.1 Hz) 8.40–8.43(3H, m) 8.85–8.87(1H, m) 8.89(1H, dd, J=1.8 and 8.1 Hz) 9.11(1H, s) 12.25(1H, brs).

Example 175

Synthesis of N-(3-methylisothiazol-5-yl)-1-[trans-4-(t-butyldiphenylsilyloxy)cyclohexyl]-1,4-dihydro[1,8]naphthylidin-4-one-3-carboxamide The same reaction was carried out as in Example 4, except for using 1-[trans- 4-(t-butyldiphenylsilyloxy)cyclohexyl]-1,4-dihydro[1,8]naphtyridin-4-one-3-carboxylic acid and 5-amino-3-methylisothiazole hydrochloride, instead of (±)-1-(1-methoxycarbonylpyrrolidin-3-yl)-1,4-dihydro[1,8] naphtyridin-4-one-3-carboxylic acid and 2,6-dichloroaniline, respectively, to obtain 64 mg (54%) of the above-identified compound as a slightly orange crystal.

IR(KBr)cm$^{-1}$: 3070, 2932, 2857, 1668, 1605, 1545, 1489, 1416, 1112, 789. MS(FAB) 623[M+1]$^+$. $^1$H-NMR(CDCl$_3$): δ 1.09(9H, s) 1.65–1.80(4H, m) 1.98–2.07(4H, m) 2.43(3H, s) 3.68–3.78(1H, m) 5.58–5.65(1H, m) 6.74(1H, s) 7.38–7.48(6H, m) 7.51 (1H, dd, J=4.5 and 8.0 Hz) 7.68–7.71 (4H, m) 8.80–8.85(2H, m) 8.95(1H, s) 12.87(1H, brs).

Example 176

Synthesis of N-(3-methylisothiazol-5-yl)-1-(trans-4-hydroxycyclohexyl)-1,4-dihydro[1,8]naphthylidin-4-one-3-carboxamide The same reaction was carried out as in Example 113, except for using N-(3-methylisothiazole-5-yl)-1-[trans-4-(t-butyldiphenylsilyloxy)cyclohexyl]-1,4-dihydro[1,8] naphtyridin-4-one-3-carboxamide, instead of N-(4-pyridyl)-1-[trans-4-(t-butyldiphenylsilyloxy)cyclohexyl]-1,4-dihydro[1,8]naphtyridin-4-one-3-carboxamide, to obtain 27 mg (87%) of the above-identified compound as a colorless crystal.

IR(KBr)cm$^{-1}$: 2940, 1672, 1605, 1549, 1489, 1416, 1080, 787. MS(FAB) 385[M+1]$^+$. $^1$H-NMR(CDCl$_3$): δ 1.62–1.72 (2H, m) 1.88–1.98(2H, m) 2.11–2.17(2H, m) 2.20–2.28(2H, m) 2.45(3H, s) 3.78–3.84(1H, m) 5.62–5.70(1H, m) 6.77 (1H, s) 7.54(1H, dd, J=4.6 and 8.0 Hz) 8.84–8.88(2H, m) 9.09(1H, s) 12.91(1H, brs).

Example 177

Synthesis of N-(3-methylisoxazol-5-yl)-1-[trans-4-(t-butyldiphenylsilyloxy)cyclohexyl]-1,4-dihydro[1,8]naphthylidin-4-one-3-carboxamide The same reaction was carried out as in Example 10, except for using 1-[trans-4-(t-butyldiphenylsilyloxy) cyclohexyl]-1,4-dihydro[1,8]naphtyridin-4-one-3-carboxylic acid and 5-amino-3-methylisoxazole, instead of (S)-1-(1-benzyloxycarbonylpyrrolidin-3-yl)-1,4-dihydro[1, 8]naphtyridin-4-one-3-carboxylic acid and 4-amino-3,5-dichloropyridine, respectively, to obtain 115 mg (quant.) of the above-identified compound as a colorless crystal.

IR(KBr)cm$^-$: 3070, 2932, 2860, 1692, 1622, 1542, 1414, 1104, 701. MS(FAB) 607[M+1]$^+$. $^1$H-NMR(CDCl$_3$): δ 1.09 (9H, s) 1.67–1.82(4H, m) 1.96–2.08(4H, m) 3.70–3.78(1H, m) 5.56–5.64(1H, m) 6.26(1H, s) 7.38–7.52(7H, m) 7.68–7.71(4H, m) 8.82–8.85(2H, m) 8.90(1H, s) 12.85(1H, brs).

Example 178

Synthesis of N-(3-methylisoxazol-5-yl)-1-(trans-4-hydroxycyclohexyl)-1,4-dihydro[1,8]naphthylidin-4-one-3-carboxamide The same reaction was carried out as in Example 113, except for using N-(3-methylisoxazol-5-yl)-1-[trans-4-(t-butyldiphenylsilyloxy)cyclohexyl]- 1,4-dihydro[1,8] naphtyridin-4-one-3-carboxamide, instead of N-(4-pyridyl)-1-[trans-4-(t-butyldiphenylsilyloxy)cyclohexyl]-1,4-dihydro[1,8]naphtyridin-4-one-3-carboxamide to obtain 65 mg (93%) of the above-identified compound as a colorless crystal.

IR(KBr)cm$^{-1}$: 3466, 2930, 1686, 1622, 1538, 1485, 1411, 1078, 794. MS(FAB) 369[M+1]$^+$. $^1$H-NMR(CDCl$_3$): δ 1.62–1.73(2 H, m) 1.90–2.00(2H, m) 2.12–2.18(2H, m) 2.22–2.28(2H, m) 2.31(3H, m) 3.81–3.88(1H, m) 5.62–5.70 (1H, m) 6.31(1H, s) 7.54(1H, dd, J=4.7 and 7.7 Hz) 8.85–8.88(2H, m) 9.03(1H, s) 12.90(1H, brs).

Example 179

Synthesis of N-(3,4-dimethylisoxazol-5-yl)-[trans-4-(t-butyldiphenylsilyloxy)cyclohexyl]-1,4-dihydro[1,8]naphthylidin-4-one-3-carboxamide The same reaction was carried out as in Example 10, except for using 1-[trans-4-(t-butyldiphenylsilyloxy) cyclohexyl]-1,4-dihydro[1,8]naphtyridin-4-one-3-carboxylic acid and 5-amino-3,4-dimethylisoxazol, instead of (S)-1-(1-benzyloxycarbonylpyrrolidin-3-yl)-1,4-dihydro[1,8]naphtyridin-4-one-3-carboxylic acid and 4-amino-3,5-dichloropyridine, respectively, to obtain 81 mg (69%) of the above-identified compound as a slightly yellow crystal.

IR(neat)cm$^{-1}$: 2934, 1694, 1614, 1532, 1486, 1110, 703. MS (FAB) 621[M+1]$^+$. $^1$H-NMR(CDCl$_3$): δ 1.08(9H, S) 1.69–1.70(4H, m) 1.93–2.08(4H, m) 1.96(3H, s) 2.23(3H, s) 3.70–3.77(1H, m) 5.56–5.65(1H, m) 7.38–7.53(7H, m) 7.68–7.71(4H, m) 8.82–8.84(2H, m) 8.91(1H, s) 12.23(1H, brs).

Example 180

Synthesis of N-(3,4-dimethylisoxazol-5-yl)-1-(trans-4-hydroxycyclohexyl)-1,4-dihydro[1,8]naphthylidin-4-one-3-carboxamide The same reaction was carried out as in Example 113, except for using N-(3,4-dimethylisoxazol-5-yl)-1-[trans-4-(t-butyldiphenylsilyloxy)cyclohexyl]-1,4-dihydro[1,8]naphtyridin-4-one-3-carboxamide, instead of N-(4-pyridyl)-1-[trans-4-(t-butyldiphenylsilyloxy)cyclohexyl]-1,4-dihydro[1,8]naphtyridin-4-one-3-carboxamide to obtain 45 mg (quant.) of the above-identified compound as a slightly yellow crystal.

IR(KBr)cm$^-$: 2934, 1688, 1605, 1537, 1488, 1415, 1353, 1199, 1072, 785. MS(FAB) 383[M+1]$^+$. $^1$H-NMR(CDCl$_3$): δ 1.60–1.75(2H, m) 1.90–2.01(2H, m) 1.99(3H, s) 2.10–2.16 (2H, m) 2.20–2.28(2H, m) 2.24(3H, s) 3.80–3.85(1H, m) 5.62–5.70 (1H, m) 7.51–7.55(1H, m) 8.85–8.88(2H, m) 9.05(1H, s) 12.25(1H, brs).

Example 181

Synthesis of N-(1,3-dimethylpyrazol-5-yl)-1-[trans-4-(t-butyldiphenylsilyloxy)cyclohexyl]-1,4-dihydro]1,8]naphthylidin-4-one-3-carboxamide The same reaction was carried out as in Example 10, except for using 1-[trans-4-(t-butyldiphenylsilyloxy) cyclohexyl]-1,4-dihydro[1,8]naphtyridin-4-one-3-carboxylic acid and 5-amino-1,3-dimethylpyrazole, instead of (S)-1-(1-benzyloxycarbonylpyrrolidin-3-yl)-1,4-dihydro[1,8]naphtyridin-4-one-3-carboxylic acid and 4-amino-3,5-dichloropyridine, respectively, to obtain 24 mg (20%) of the above-identified compound as a colorless crystal.

IR(KBr)cm$^{-1}$: 3070, 2931, 1687, 1583, 1414, 1103, 777. MS (FAB) 620[M+1]$^+$. $^1$H-NMR(CDCl$_3$): δ 1.56(9H, s) 1.58–1.81(4H, m) 1.96–2.10(4H, m) 2.26(3H, s) 3.70–3.78 (1H, m) 3.83(3H, s) 5.57–5.68(1H, m) 6.35(1H, s) 7.39–7.50 (7H, m) 7.69–7.71(4H, m) 8.83–8.85(1H, m) 8.95(1H, s) 12.38(1H, br s).

Example 182

Synthesis of N-(1,3-dimethylpyrazol-5-yl)-1-(trans-4-hydroxycyclohexyl)-1,4-dihydro[1,8]naphthylidin-4-one-3-carboxamide The same reaction was carried out as in Example 113, except for using N-(1,3-dimethylpyrazol-5-yl)-1-[trans-4-(t-butyldiphenylsilyloxy)cyclohexyl]-1,4-dihydro[1,8] naphtyridin-4-one-3-carboxamide, instead of N-(4-pyridyl)-1-[trans-4-(t-butyldiphenylsilyloxy)cyclohexyl]-1,4-dihydro[1,8]naphtyridin-4-one-3-carboxamide, to obtain 11 mg (92%) of the above-identified compound as a colorless crystal.

IR(KBr)cm$^{-1}$: 2932, 1667, 1572, 1415, 1438, 1076, 787. MS (FAB) 382[M+1]$^+$. $^1$H-NMR(CDCl$_3$): δ 1.60–1.74(2H, m) 1.92–2.01(2H, m) 2.10–2.18(2H, m) 2.21–2.30(2H, m) 2.27(3H, s) 3.81–3.90(1H, m) 3.86(3H, s) 5.62–5.72(1H, m) 6.39(1H, s) 7.54(1H, dd, J=4.9 and 7.5 Hz) 8.84–8.88(2H, m) 9.09(1H, s) 12.40(1H, brs).

Example 183

Synthesis of N-(1,3,5-trimethylpyrazol-4-yl)-1-[trans-4-(t-butyldiphenylsilyloxy)cyclohexyl]-1,4-dihydro[1,8]naphthylidin-4-one-3-carboxamide The same reaction was carried out as in Example 10, except for using 1-[trans- 4-(t-butyldiphenylsilyloxy) cyclohexyl]-1,4-dihydro[1,8]naphtyridin-4-one-3-carboxylic acid and 4-amino-1,3,5-trimethylpyrazole, instead of (S)-1-(1-benzyloxycarbonylpyrrolidin-3-yl)-1,4-dihydro[1,8]naphtyridin-4-one-3-carboxylic acid and 4-amino-3,5-dichloropyridine, respectively, to obtain 140 mg (quant.) of the above-identified compound as a colorless crystal.

IR(KBr)cm$^{-1}$: 3073, 2925, 1668, 1602, 1562, 1489, 1413, 1079, 701. MS(FAB) 634[M+1]$^+$. $^1$H-NMR(CDCl$_3$): δ 1.08 (9H, s) 1.65–1.80(4H, m) 1.91–2.08(4H, m) 2.17(3H, s) 2.18(3H, s) 3.70–3.85(1H, m) 3.73(3H, s) 5.55–5.65(1H, m) 7.38–7.48(7H, m) 7.67–7.71(4H, m) 8.81–8.85(2H, m) 8.94 (1H, s) 11.02(1H, brs).

Example 184

Synthesis of N-(1,3,5-trimethylpyrazol-4-yl)-1-(trans-4-hydroxycyclohexyl)-1,4-dihydro[1,8] naphthylidin-4-one-3-carboxamide The same reaction was carried out as in Example 113, except for using N-(1,3,5-trimethylpyrazol-4-yl)-1-[trans-4-(t-butyldiphenylsilyloxy)cyclohexyl]-1,4-dihydro[1,8] naphtyridin-4-one-3-carboxamide, instead of N-(4-pyridyl)-1-[trans-4-(t-butyldiphenylsilyloxy)cyclohexyl]-1,4-dihydro[1,8]naphtyridin-4-one-3-carboxamide, to obtain 58 mg (77%) of the above-identified compound as a colorless crystal.

IR(KBr)cm$^{-1}$: 3388, 2942, 1672, 1603, 1526, 1485, 1411, 1302, 1200, 1082, 786. MS(FAB) 396[M+1]$^+$. $^1$H-NMR (CDCl$_3$): δ 1.59–2.04(4H, m) 2.09–2.33(4H, m) 2.21(3H, s) 3.49(3H, s) 3.74(3H, s) 3.76–3.88(1H, m) 5.61–5.70(1H, m) 7.50(1H, dd, J=4.5 and 7.9 Hz) 8.83–8.88(2H, m) 9.08(1H, s) 11.02(1H, brs).

Example 185

Synthesis of tert-butyl N-(4-hydroxy-4-methylcyclohexyl)carbamate

To a 6 ml anhydrous tetrahydrofuran solution of 303 mg (1.42 mmol) of tert-butyl N-(4-oxocyclohexyl)carbamate, 2.7 ml of methyl lithium (1.1M in hexane, 2.98 mmol) was dropwise added at −78° C. under an argon atmosphere and stirred for 1.5 hours, after adding 20 ml of water thereto to return room temperature, followed by extracting with 30 ml of methylene chloride after drying over anhydrous sodium sulfate, the solvent was distilled off and the residue was purified by a silica gel column chromatography (hexane/ethyl acetate=1/1) to obtain 150 mg (46%) of non-polar side diastereomer as a colorless crystal and 54 mg (17%) of polar side diastereomer as a colorless crystal.

Non-polar side diastereomer $^1$H-NMR(CDCl$_3$): δ 1.23(3H, s) 1.44(9H, s) 1.45–1.57 (4H, m) 1.62–1.69(2H, m) 1.76–1.85(2H, m) 3.33–3.46(1H, br) 4.34–4.48(1H, br).

Polar Side Diastereomer $^1$H-NMR(CDCl$_3$): δ 1.25(3H, s) 1.28–1.41(2H, m) 1.44 (9H, s) 1.47–1.57(2H, m) 1.60–1.68(2H, m) 1.89–1.99(2H, m) 3.50–3.63(1H, br) 4.37–4.51(1H, br).

Example 186

Synthesis of 4-amino-1-methyl-1-cyclohexanol trifluoroacetic acid salt

To a 1 ml methylene chloride solution of 70 mg (0.31 mmol) of the compound (i.e., non-polar side diastereomer), obtained in Example 185, 353 μl (4.58 mmol) of trifluoroacetic acid was added and was stirred at room temperature for 1 hour, followed by distilling off the solvent. The residue was washed with diethyl ether, to obtain 76 mg (quant.) of the above-identified compound as a colorless crystal.

MS(FAB) 130[M(free)+H]$^+$. $^1$H-NMH(DMSO-d$_6$): δ 1.09(3H, s) 1.25–1.36(2H, m) 1.51–1.69(6H, m) 2.83–2.96 (1H, br) 4.06–4.19(1H, br) 7.62–7.77(2H, br).

Example 187

Synthesis of ethyl 3-[(4-hydroxy-4-methylcyclohexyl)amino]-2-(2-chloronicotinoyl) acrylate The same reaction was carried out as in Example 1, except for using 4-amino-1-methyl-1-cyclohexanol trifluoroacetic acid salt obtained in Example 186, instead of (±)-3-amino-1-methoxycarbonylpyrrolidine, to obtain 2.55 g (85%) of the above-identified compound as a slightly brown crystal.

IR(KBr)cm$^{-1}$: 3470, 3205, 2935, 1676, 1619, 1560, 1391, 1270. MS(FAB) 367[M+H]$^+$. $^1$H-NMR(CDCl$_3$): δ 0.78 and 0.91(total 3H, d, J=7.1 Hz) 1.20–2.62(11H, m) 3.84–4.02 (3H, m) 7.22–7.30 (1H, m) 7.50–7.59(1H, m) 8.20–8.41(2H, m) 9.58–9.80(0.2H, m) 11.03–11.28(0.8H, m).

Example 188

Synthesis of ethyl 1-(4-hydroxy-4-methylcyclohexyl)-1,4-dihydro[1,8]naphthylidin-4-one-3-carboxylate The same reaction was carried out as in Example 2, except for using ethyl 3-[(4-hydroxy-4-methylcyclohexyl)amino]-2-(2-chloronicotinoyl)acrylate obtained in Example 187, instead of (±)-ethyl 3-(1-methoxycarbonylpyrrolidin-3-ylamino)-2-(2-chloronicotinoyl)acrylate, to obtain 1.22 g (54%) of the above-identified compound as a colorless foaming substance.

IR(KBr)cm$^{-1}$: 3432, 2938, 1700, 1634, 1608, 1414, 1215. MS (FAB) 331[M+H]$^+$. $^1$H-NMR(CDCl$_3$): δ 1.35(3H, s) 1.42(3H, t, J=7.1 Hz) 1.71–1.81(2H, m) 1.85–1.95(4H, m) 2.15–2.29(2H, m) 4.41(2H, q, J=7.1 Hz) 5.45–5.55(1H, m) 7.40(1H, dd, J=4.5 and 8.0 Hz) 8.71(1H, dd, J=2.0 and 4.5 Hz) 8.81(1H, dd, J=2.0 and 8.0 Hz) 8.81(1H, s).

Example 189

Synthesis of ethyl 1-[4-(tert-butyldimethylsilyl)oxy-4-methylcyclohexyl]-1,4-dihydro[1,8]naphthylidin-4-one-3-carboxylate To a 6 ml anhydrous methylene chloride solution of 400 mg (1.21 mmol) of the compound obtained in Example 188, 211 μl (1.82 mmol) of 2,6-lutidine and 334 μl (1.45 mmol) of tert-butyldimethylsilyl trifluoromethane sulfonate were dropwise added at 0° C. under an argon atmosphere and stirred at room temperature for 2 hours, followed by further adding 211 μl (1.82 mmol) of 2,6-lutidine and 334 μl (1.45 mmol) of tert-butyldimethylsilyl trifluoromethane sulfonate and stirring for 1.5 hours. Then, 15 ml of water was added and the reaction mixture was extracted with methylene chloride (20 ml×2). After drying over anhydrous sodium sulfate, the solvent was distilled off and the residue was purified with silica gel chromatography (hexane/ethyl acetate=1/1), to obtain 160 mg (30%) of the above-identified compound as a colorless crystal.

IR(KBr)cm$^{-1}$: 2929, 2855, 1728, 1634, 1415, 1210, 1092. MS (FAB) 445[M+H]$^+$. $^1$H-NMR(CDCl$_3$): δ 0.16(6H, s) 1.0(9H, s) 1.34(3H, s) 1.41(3H, t, J=7.1 Hz) 1.57–1.68(2H, m) 1.75–1.94(4H, m) 2.15–2.29(2H, m) 4.39(2H, q, J=7.1 Hz) 5.46–5.53(1H, m) 7.39(1H, dd, J=4.5 and 7.9 Hz) 8.71(1H, dd, J=1.9 and 4.5 Hz) 8.77(1H, s) 8.81(1H, dd, J=1.9 and 7.9 Hz).

Example 190

Synthesis of 1-[4-(tert-butyldimethylsilyl)oxy-4-methylcyclohexyl]-1,4-dihydro[1,8]naphthylidin-4-one-3-carboxylic acid The same reaction was carried out as in Example 3, except for using ethyl 1-[4-(tert-butyldimethylsilyl)oxy-4-methylcyclohexyl]-1,4-dihydro[1,8]naphtyridin-4-one-3-carboxylate obtained in Example 189, instead of (±)-ethyl 1-(1-methoxycarbonylpyrrolidin-3-yl)-1,4-dihydro[1,8]naphthyridin-4-one-3-carboxylate, to obtain 115 mg (95%) of the above-identified compound as a colorless crystal.

IR(KBr)cm$^{-1}$: 2935, 1728, 1615, 1471. MS(FAB) 417 [M+H]$^+$. $^1$H-NMR(CDCl$_3$): δ 0.15(6H, s) 1.00(9H, s) 1.35 (3H, s) 1.57–1.70(2H, m) 1.80–1.97(4H, m) 2.22–2.38(2H, m) 5.51–5.65(1H, m) 7.55(1H, dd, J=4.5 and 8.0 Hz) 8.82–8.89(2H, m) 9.06(1H, s) 14.4(1H, s).

Example 191

Synthesis of N-(3,5-dichloropyridin-4-yl)-1-[4-(tert-butyldimethylsilyl)oxy-4-methylcyclohexyl]-1,4-dihydro[1,8]naphthylidin-4-one-3-carboxamide The same reaction was carried out as in Example 10, except for using 1-[4-(tert-butyldimethylsilyl)oxy-4-methylcyclohexyl]-1,4-dihydro[1,8]naphtyridin-4-one-3-carboxylic acid obtained in Example 190, instead of (S)-1-(1-benzyloxycarbonylpyrrolidin-3-yl)-1,4-dihydro[1,8] naphtyridin-4-one-3-carboxylic acid, to obtain 124 mg (88%) of the above-identified compound as a slightly yellow crystal.

IR(KBr)cm$^{-1}$: 2926, 1694, 1616, 1538, 1485, 1410. MS(FAB) 561[M+H]$^+$. $^1$H-NMR(CDCl$_3$): δ 0.14(6H, s) 0.97(9H, s) 1.35(3H, s) 1.57–1.71(2H, m) 1.84–1.96(4H, m) 2.26–2.42(2H, m) 5.45–5.60(1H, m) 7.50(1H, dd, J=4.5 and 8.0 Hz) 8.55(2H, s) 8.84(1 H, dd, J=2.0 and 4.5 Hz) 8.89(1H, dd, J=2.0 and 8.0 Hz) 9.15(1 H, s) 12.17(1H, s).

Example 192

Synthesis of N-(3,5-dichloropyridin-4-yl)-1-(4-hydroxy-4-methylcyclohexyl)-1,4-dihydro[1,8]naphthylidin-4-one-3-carboxamide To a 2 ml N,N-dimethylformamide solution of 118 mg (0.21 mmol) of the compound obtained in Example 191, 1.68 ml of tetrabutylammonium fluoride (1M in THF, 1.68 mmol) was added under an argon atmosphere and stirred at 70° C. for 6 hours. Thereafter, 20 ml of ethyl acetate was added thereto, followed by successively washing with 8 ml of water and 5 ml of saturated saline.

Then, after drying over anhydrous sodium sulfate, the solvent was distilled off and the residue was purified by silica gel chromatography (hexane/ethyl acetate=1/1.5), to obtain 76 mg (81%) of the above-identifLed compound as a slightly yellow crystal.

IR(KBr)cm$^{-1}$: 3501, 3460, 2938, 1675, 1616, 1538, 1484, 1414. MS(FAB) 447[M+H]$^+$. $^1$H-NMR(CDCl$_3$): δ 1.35(3H, s) 1.71–1.82(2H, m) 1.86–1.96(4H, m) 2.25–2.39(2H, m) 5.56–5.66(1H, m) 7.52(1H, dd, J=4.5 and 8.0 Hz) 8.56(2H, s) 8.85(1H, dd, J=2.0 and 4.5 Hz) 8.89(1H, dd, J=2.0 and 8.0 Hz) 9.20(1H, s) 12.23 (1H, s).

Example 193

Synthesis of N-(4-pyridinyl)-1-[4-(tert-butyldimethylsilyl)oxy-4-methylcyclohexyl]-1,4-dihydro[1,8]naphthylidin-4-one-3-carboxamide The same reaction was carried out as in Example 4, except for using 1-[4-(tert-butyldimethylsilyl)oxy-4-methylcyclohexyl]-1,4-dihydro[1,8]naphtyridin-4-one-3-carboxylic acid obtained in Example 190 and 4-aminopyridine, instead of (±)-1-(1-methoxycarbonylpyrrolidin-3-yl)-1,4-dihydro[1,8]naphtyridin-4-one-3-carboxylic acid and 2,6-dichloroaniline, respectively, to obtain 94 mg (79%) of the above-identified compound as a colorless crystal.

IR(KBr)cm$^{-1}$: 3438, 2933, 1694, 1604, 1530, 1491. MS(FAB) 493[M+H]$^+$. $^1$H-NMR(CDCl$_3$): δ 0.15–0.18(6H, m) 1.01–1.04(9H, m) 1.35–1.37(3H, m) 1.59–1.70(2H, m) 1.79–1.96(4H, m) 2.25–2.40(2H, m) 5.50–5.62(1H, m) 7.48–7.55(1H, m) 7.68–7.74(2H, m) 8.50–8.56(2H, m) 8.82–8.89(2H, m) 9.17–9.19(1H, m) 12.32(1 H, brs).

Example 194

Synthesis of N-(4-pyridinyl)-1-(4-hydroxy-4-methylcyclohexyl)-1,4-dihydro[1,8]naphthylidin-4-one-3-carboxamide The same reaction was carried out as in Example 192, except for using N-(4-pyridinyl)-1-[4-(tert-butyldimethylsilyl)oxy-4-methylcyclohexyl]-1,4-dihydro[1,8]naphthyridin-4-one-3-carboxamide obtained in Example 193, instead of N-(3,5-dichloropyridin-4-yl)-1-[4-(tert-butyldimethylsilyl)oxy-4-methylcyclohexyl]-1,4-dihydro[1,8]naphthyridin-4-one-3-carboxamide, to obtain 20 mg (30%) of the above-identified compound as a colorless crystal.

IR(KBr)cm$^{-1}$: 3286, 2935, 1687, 1604, 1570, 1531, 1490, 1417. MS(FAB) 379[M+H]$^+$. $^1$H-NMR(CDCl$_3$): δ 1.36(3H, s) 1.71–1.85(2H, m) 1.88–1.96(4H, m) 2.25–2.39(2H, m) 5.56–5.66(1H, m) 7.53(1H, dd, J=4.5 and 8.0 Hz) 7.70(2H, d, J=6.3 Hz) 8.53(2H, d, J=6.3 Hz) 8.82–8.92(2H, m) 9.21(1H, s) 12.37(1H, brs).

Example 195

Synthesis of 1-(trans-4-hydroxycyclohexyl)-1,4-dihydro[1,8]naphthylidin-4-one-3-carboxylic acid The same reaction was carried out as in Example 3, except for using ethyl 1-(trans-4-hydroxycyclohexyl)-1,4-dihydro[1,8]naphtyridin-4-one-3-carboxylate, instead of (±)-ethyl 1-(1-methoxycarbonylpyrrolidin-3-yl)-1,4-dihydro[1,8]naphtyridin-4-one-3-carboxylate, to obtain 300 mg (98%) of the above-identified compound as a colorless crystal.

IR(KBr)cm$^{-1}$: 3464, 2924, 2861, 1712, 1616, 1472, 1419. MS (FAB) 289[M+H]$^+$. $^1$H-NMR(CDCl$_3$): δ 1.60–1.74(2H, m) 1.86–2.00(2H, m) 2.09–2.17(2H, m) 2.21–2.28(2H, m) 3.78–3.88(1H, m) 5.62–5.73(1H,m) 7.57(1H, dd, J=4.5 and 8.0 Hz) 8.85(1H, dd, J=2.0 and 8.0 Hz) 8.90(1H, dd, J=2.0 and 4.5 Hz) 8.97(1H, s) 14.49(1H, brs).

Example 196

Synthesis of 1-(trans-4-acetoxycyclohexyl)-1,4-dihydro[1,8]naphthylidin-4-one-3-carboxylic acid To a 6 ml anhydrous methylene chloride suspension of 100 mg (0.35 mmol) of the compound obtained in Example 195, 61.7 μl (0.87 mmol) of acetyl chloride was added under an argon atmosphere and was stirred at 45° C. while stirring, 61.7 μl (0.87 mmol) of acetyl chloride was further added twice with one hour interval and, then, stirred at the same temperature for 15 hours, followed by adding 20 ml of methylene chloride and by washing with 10 ml of water. Thereafter, the reaction mixture was dried over anhydrous sodium sulfate and, then, the solvent was distilled off, to obtain 123 mg (quant.) of the above-identified compound as a colorless crystal.

IR(KBr)cm$^{-1}$: 3062, 2942, 1731, 1619, 1480, 1234. MS(FAB) 331[M+H]$^+$. $^1$H-NMR(CDCl$_3$): δ 1.65–1.79(2H, m) 1.90–2.07(2H, m) 2.08(3H, s) 2.12–2.21(2H, m) 2.25–2.32(2H, m) 4.76–4.86(1 H, m) 5.57–5.69(1H, m) 7.57(1H, dd, J=4.5 and 8.0 Hz) 8.85(1H, dd, J=2.0 and 8.0 Hz) 8.90(1H, dd, J=2.0 and 4.5 Hz) 8.97(1H, s) 14.42(1H, brs).

Example 197

Synthesis of trans-4-[3-{[(3,5-dichloropyridin-4-yl)amino]carbonyl}-1,4-dihydro[1,8]naphthylidin-1-yl]cyclohexyl acetate The same reaction was carried out as in Example 10, except for using 1-(trans-4-acetoxycyclohexyl)-1,4-dihydro[1,8]naphthylidin-4-one-3-carboxylic acid, instead of (S)-1-(1-benzyloxycarbonylpyrrolidin-3-yl)-1,4-dihydro[1,8]naphthyridin-4-one-3-carboxylic acid to obtain 88 mg (54%) of the above-identified compound as a slightly yellow crystal.

IR(KBr)cm$^{-1}$: 3435, 2949, 1732, 1694, 1615, 1489, 1414. MS (FAB) 475[M+H]$^+$. $^1$H-NMR(CDCl$_3$): δ 1.66–1.81(2H, m) 1.98–2.11(2H, m) 2.08(3H, s) 2.14–2.21(2H, m) 2.24–2.32(2H, m) 4.79–4.90(1H, m) 5.57–5.69(1H,m) 7.53 (1H, dd, J=4.5 and 8.0 Hz) 8.56(2H, s) 8.85(1H, dd, J=1.8 and 4.5 Hz) 8.89(1H, dd, J=1.8 and 8.0 Hz) 9.06(1H, s) 12.14(1H, brs).

What is claimed is:

1. A 1-cycloalkyl-1,8-naphthyridin-4-one derivative having the formula (I'):

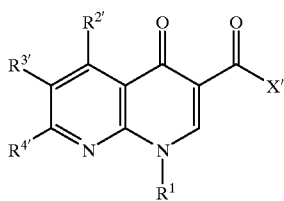

(I')

wherein R¹ indicates a substituted or unsubstituted cycloalkyl group or a substituted or unsubstituted heterocycloalkyl group, R²', R³', and R⁴' independently indicate a hydrogen atom, a substituted or unsubstituted lower alkyl group, X' indicates a group NR⁵R⁶, wherein R⁵ and R⁶ independently indicate a hydrogen atom, a substituted or unsubstituted lower alkyl group, a substituted or unsubstituted cycloalkyl group, a substituted or unsubstituted aryl group, or a substituted or unsubstituted heteroaryl group, provided that R⁵ and R⁶ do not indicate a substituted or unsubstituted lower alkyl group at the same time, or a salt or solvate thereof.

2. A 1-cycloalkyl-1,8-naphthylidin-4-one derivative or a salt or solvate thereof as claimed in claim 1, wherein all of R²', R³', and R⁴' in the formula (I') are hydrogen atoms.

3. A 1-cycloalkyl-1,8-naphthylidin-4-one derivative or a salt or solvate thereof as claimed in claim 1, wherein R¹ in the formula (I') is a substituted or unsubstituted cyclohexyl group, a substituted or unsubstituted cyclopentyl group, a substituted or unsubstituted cyclobutyl group, or a substituted or unsubstituted cyclopropyl group.

4. A 1-cycloalkyl-1,8-naphthylidin-4-one derivative or a salt or solvate thereof as claimed in claim 1, wherein R¹ in the formula (I') is a substituted or unsubstituted 5- or 6-membered heterocycloalkyl group containing one oxygen or sulfur atom.

5. A 1-cycloalkyl-1,8-naphthylidin-4-one derivative or a salt, or solvate thereof as claimed in claim 1, wherein R¹ in the formula (I') is a substituted or unsubstituted 5- or 6-membered heterocycloalkyl group containing at least two same or different hetero atoms selected from an oxygen atom or a sulfur atom and a nitrogen atom.

6. A 1-cycloalkyl-1,8-naphthylidin-4-one derivative or a salt or solvate thereof as claimed in claim 1, wherein R¹ in the formula (I') is a substituted or unsubstituted azetidinyl group, a substituted or unsubstituted pyrrolidinyl group, a substituted or unsubstituted piperidyl group, or a substituted or unsubstituted tetrahydrofuryl group.

7. A 1-cycloalkyl-1,8-naphthylidin-4-one derivative or a salt or solvate thereof as claimed in claim 1, wherein either one of R⁵ or R⁶ in the formula (I') is a hydrogen atom.

8. A 1-cycloalkyl-1,8-naphthylidin-4-one derivative or a salt or solvate thereof as claimed in claim 1, wherein either one of R⁵ or R⁶ in the formula (I') is a substituted or unsubstituted phenyl group and the other is a hydrogen atom.

9. A 1-cycloalkyl-1,8-naphthylidin-4-one derivative or a salt or solvate thereof as claimed in claim 1, wherein either one of R⁵ or R⁶ in the formula (I') is a substituted or unsubstituted pyridyl group and the other is a hydrogen atom.

10. A 1-cycloalkyl-1,8-naphthylidin-4-one derivative or a salt or solvate thereof as claimed in claim 1, wherein either one of R⁵ or R⁶ in the formula (I') is a 4-pyridyl group and the other is a hydrogen atom.

11. A 1-cycloalkyl-1,8-naphthylidin-4-one derivative or a salt or solvate thereof as claimed in claim 1, wherein either one of R⁵ or R⁶ in the formula (I') is a 3,5-dichloropyridine-4-yl group and the other is a hydrogen atom.

12. A pharmaceutical composition comprising, as an effective component, a 1-cycloalkyl-1,8-naphthylidin-4-one derivative having the formula (I'):

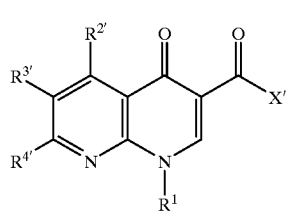

(I')

wherein R¹ indicates a substituted or unsubstituted cycloalkyl group or a substituted or unsubstituted heterocycloalkyl group, R²', R³', and R⁴' independently indicate a hydrogen atom, a substituted or unsubstituted lower alkyl group, X' indicates a group NR⁵R⁶, wherein R⁵ and R⁶ independently indicate a hydrogen atom, a substituted or unsubstituted lower alkyl group, a substituted or unsubstituted cycloalkyl group, a substituted or unsubstituted aryl group, or a substituted or unsubstituted heteroaryl group, provided that R⁵ and R⁶ do not indicate a substituted or unsubstituted lower alkyl group at the same time, or a pharmaceutical acceptable salt or solvate thereof.

13. A method for preventing or treating a cytokine related disease comprising administering an effective amount of a compound according to claim 1 to a patient in need of such treatment.

14. A pharmaceutical composition comprising an effective amount of a 1-cycloalkyl-1,8-naphthylidin-4-one derivative having the formula (I-1):

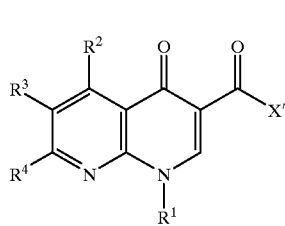

(I-1)

wherein R¹ indicates a substituted or unsubstituted cycloalkyl group or a substituted or unsubstituted heterocycloalkyl group, R², R³, and R⁴ independently indicate a hydrogen atom, a substituted or unsubstituted lower alkyl group, or a halogen atom, X' indicates a group NR⁵R⁶, wherein R⁵ and R⁶ independently indicate a hydrogen atom, a substituted or unsubstituted lower alkyl group, a substituted or unsubstituted cycloalkyl group, a substituted or unsubstituted aryl group, or a substituted or unsubstituted heteroaryl group, provided that R⁵ and R⁶ do not indicate a unsubstituted lower alkyl group at the same time, or a pharmaceutically acceptable salt or solvate thereof.

15. A method for preventing or treating a cytokine related disease comprising administering an effective amount of a composition according to claim 14 to a patient in need of such treatment.

16. A pharmaceutical composition comprising an effective amount of a 1-cycloalkyl-1,8-naphthylidin-4-one derivative or a pharmaceutically acceptable salt, or solvate as claimed in claim 14, wherein all of $R^2$, $R^3$ and $R^4$ in the formula (I-1) are hydrogen atoms.

17. A pharmaceutical composition comprising an effective amount of a 1-cycloalkyl-1,8-naphthylidin-4-one derivative or a pharmaceutically acceptable salt or solvate thereof as claimed in claim 14, wherein $R^1$ in the formula (I-1) is a substituted or unsubstituted cyclohexyl group, a substituted or unsubstituted cyclopentyl group, a substituted or unsubstituted cyclobutyl group or a substituted or unsubstituted cyclopropyl group.

18. A pharmaceutical composition comprising an effective amount of a 1-cycloalkyl-1,8-naphthylidin-4-one derivative or a pharmaceutically acceptable salt or solvate thereof as claimed in claim 14, wherein $R^1$ in the formula (I-1) is a substituted or unsubstituted 5- or 6-membered heterocycloalkyl group containing one oxygen or sulfur atom.

19. A pharmaceutical composition comprising, as an effective component, a 1-cycloalkyl-1,8-naphthylidin-4-one derivative or a pharmaceutically acceptable salt or solvate thereof as claimed in claim 14, wherein $R^1$ in the formula (I-1) is a substituted or unsubstituted 5- or 6-membered heterocycloalkyl group containing at least two same or different hetero atoms selected from an oxygen atom, a sulfur atom and a nitrogen atom.

20. A pharmaceutical composition comprising an effective amount of a 1-cycloalkyl-1,8-naphthylidin-4-one derivative or a pharmaceutically acceptable salt or solvate thereof as claimed in claim 14, wherein $R^1$ in the formula (I-1) is a substituted or unsubstituted azetidinyl group, a substituted or unsubstituted pyrrolidinyl group, a substituted or unsubstituted piperidyl group or a substituted or unsubstituted tetrahydrofuryl group.

21. A pharmaceutical composition comprising an effective amount of a 1-cycloalkyl-1,8-naphthylidin-4-one derivative or a pharmaceutically acceptable salt or solvate thereof as claimed in claim 14, wherein either one of $R^5$ or $R^6$ in the formula (I-1) is a hydrogen atom.

22. A pharmaceutical composition comprising an effective amount of a 1-cycloalkyl-1,8-naphthylidin-4-one derivative or a pharmaceutically acceptable salt or solvate thereof as claimed in claim 14, wherein either one of $R^5$ or $R^6$ in the formula (I-1) is a substituted or unsubstituted phenyl group and the other is a hydrogen atom.

23. A pharmaceutical composition comprising an effective amount of a 1-cycloalkyl-1,8-naphthylidin-4-one derivative or a pharmaceutically acceptable salt or solvate thereof as claimed in claim 14, wherein either one of $R^5$ or $R^6$ in the formula (I-1) is a substituted or unsubstituted pyridyl group and the other is a hydrogen group.

24. A pharmaceutical composition comprising an effective amount of a 1-cycloalkyl-1,8-naphthylidin-4-one derivative or a pharmaceutically acceptable salt or solvate thereof as claimed in claim 14, wherein either one of $R^5$ or $R^6$ in the formula (I-1) is a 4-pyridyl group and the other is a hydrogen atom.

25. A pharmaceutical composition comprising an effective amount of a 1-cycloalkyl-1,8-naphthylidin-4-one derivative or a pharmaceutically acceptable salt or solvate thereof as claimed in claim 14, wherein either one of $R^5$ or $R^6$ in the formula (I-1) is a 3,5-dichloropyridin-4-yl group and the other is a hydrogen atom.

26. A method for preventing or treating a cytokine related disease comprising administering, to a patient in need of such treatment, an effective amount of a compound having the formula (I):

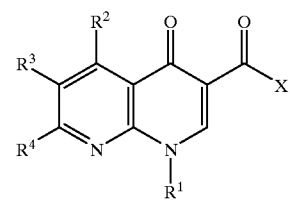

(I)

wherein $R^1$ indicates a substituted or unsubstituted cycloalkyl group or a substituted or unsubstituted heterocycloalkyl group, $R^2$, $R^3$, and $R^4$ independently indicate a hydrogen atom, a substituted or unsubstituted lower alkyl group, or a halogen atom, X indicates a group $NR^5R^6$ or a group $OR^7$, wherein $R^5$ and $R^6$ independently indicate a hydrogen atom, a substituted or unsubstituted lower alkyl group, a substituted or unsubstituted cycloalkyl group, a substituted or unsubstituted aryl group, or a substituted or unsubstituted heteroaryl group, and $R^7$ indicates a hydrogen atom, a substituted or unsubstituted lower alkyl group, a substituted or unsubstituted cycloalkyl group or a pharmaceutically acceptable salt or solvate thereof.

27. A method for inhibiting a type IV phosphodiesterase comprising administering, to a patient in need of such inhibition, an effective amount of a compound having the formula (I):

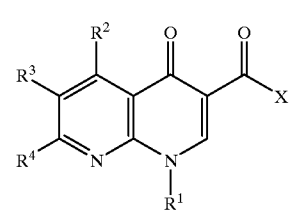

(I)

wherein $R^1$ indicates a substituted or unsubstituted cycloalkyl group or a substituted or unsubstituted heterocycloalkyl group, $R^2$, $R^3$, and $R^4$ independently indicate a hydrogen atom, a substituted or unsubstituted lower alkyl group, or a halogen atom, X indicates a group $NR^5R^6$ or a group $OR^7$, wherein $R^5$ and $R^6$ independently indicate a hydrogen atom, a substituted or unsubstituted lower alkyl group, a substituted or unsubstituted cycloalkyl group, a substituted or unsubstituted aryl group, or a substituted or unsubstituted heteroaryl group, and $R^7$ indicates a hydrogen atom, a substituted or unsubstituted lower alkyl group, a substituted or unsubstituted cycloalkyl group or a pharmaceutically acceptable salt or solvate thereof.

28. A method for inhibiting a type IV phosphodiesterase comprising administering an effective amount of a composition according to claim 14 to a patient in need of such inhibition.

29. A method for inhibiting a type IV phosphodiesterase comprising administering an effective amount of a compound according to claim 1 to a patient in need of such inhibition.

30. A method for inhibiting production of TNF-α comprising administering, to a patient in need of such inhibition, an effective amount of a compound having the formula (I):

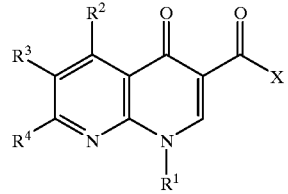

(I)

wherein $R^1$ indicates a substituted or unsubstituted cycloalkyl group or a substituted or unsubstituted heterocycloalkyl group, $R^2$, $R^3$, and $R^4$ independently indicate a hydrogen atom, a substituted or unsubstituted lower alkyl group, or a halogen atom, X indicates a group $NR^5R^6$ or a group $OR^7$, wherein $R^5$ and $R^6$ independently indicate a hydrogen atom, a substituted or unsubstituted lower alkyl group, a substituted or unsubstituted cycloalkyl group, a substituted or unsubstituted aryl group, or a substituted or unsubstituted heteroaryl group, and $R^7$ indicates a hydrogen atom, a substituted or unsubstituted lower alkyl group, or a substituted or unsubstituted cycloalkyl group or a pharmaceutically acceptable salt or solvate thereof.

31. A method for inhibiting production of TNF-α comprising administering an effective amount of composition compound according to claim 14 to a patient in need of such inhibition.

32. A method for inhibiting production of TNF-α comprising administering an effective amount of a compound according to claim 1 to a patient in need of such inhibition.

33. A 1-cycloalkyl-1,8-naphthylidin-4-one derivative having the formula (I-1):

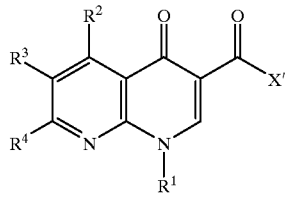

(I-1)

wherein $R^1$ indicates a substituted or unsubstituted cycloalkyl group or a substituted or unsubstituted heterocycloalkyl group, $R^2$, $R^3$, and $R^4$ independently indicate a hydrogen atom, a substituted or unsubstituted lower alkyl group, or a halogen atom, X' indicates a group $NR^5R^6$, wherein $R^5$ and $R^6$ independently indicate a hydrogen atom, a substituted or unsubstituted lower alkyl group, a substituted or unsubstituted cycloalkyl group, a substituted or unsubstituted aryl group, or a substituted or unsubstituted heteroaryl group, provided that $R^5$ and $R^6$ do not indicate a substituted or unsubstituted lower alkyl group at the same time, or a salt or solvate thereof.

34. A pharmaceutical composition of matter comprising an effective amount of a compound according to claim 33.

35. A pharmaceutical composition of matter comprising an effective amount of a compound according to claim 1.

* * * * *